US010794915B2

(12) United States Patent
Marriott et al.

(10) Patent No.: US 10,794,915 B2
(45) Date of Patent: Oct. 6, 2020

(54) GENETICALLY ENCODED SENSORS FOR IMAGING PROTEINS AND THEIR COMPLEXES

(71) Applicants: The Regents of the University of California, Oakland, CA (US); President and Board of Trustees of Santa Clara College, Santa Clara, CA (US)

(72) Inventors: Gerard Marriott, Palo Alto, CA (US); Alexander Chris Hoepker, Oakland, CA (US); Yuling Yan, Oakland, CA (US)

(73) Assignees: THE REGENTS OF THE UNIVERSITY OF CALIFORNIA, Oakland, CA (US); PRESIDENT AND BOARD OF TRUSTEES OF SANTA CLARA COLLEGE, Santa Clara, CA (US)

( * ) Notice: Subject to any disclaimer, the term of this patent is extended or adjusted under 35 U.S.C. 154(b) by 273 days.

(21) Appl. No.: 14/946,461

(22) Filed: Nov. 19, 2015

(65) Prior Publication Data
US 2016/0146827 A1 May 26, 2016

Related U.S. Application Data

(63) Continuation-in-part of application No. PCT/US2014/038644, filed on May 19, 2014.

(60) Provisional application No. 61/825,434, filed on May 20, 2013.

(51) Int. Cl.
| | |
|---|---|
| *G01N 33/58* | (2006.01) |
| *C07K 14/415* | (2006.01) |
| *C07K 14/195* | (2006.01) |
| *C07K 14/28* | (2006.01) |
| *C07K 17/02* | (2006.01) |

(52) U.S. Cl.
CPC ......... *G01N 33/582* (2013.01); *C07K 14/195* (2013.01); *C07K 14/28* (2013.01); *C07K 14/415* (2013.01); *C07K 17/02* (2013.01); *C07K 2319/00* (2013.01); *C07K 2319/21* (2013.01); *C07K 2319/50* (2013.01)

(58) Field of Classification Search
None
See application file for complete search history.

(56) References Cited

U.S. PATENT DOCUMENTS

| 2003/0013132 A1 | 1/2003 | Contag et al. | |
|---|---|---|---|
| 2006/0099646 A1* | 5/2006 | Heding | G01N 33/542 435/7.1 |
| 2012/0142015 A1 | 6/2012 | Rasenick et al. | |

FOREIGN PATENT DOCUMENTS

| EP | 2 999 700 A2 | 3/2016 |
|---|---|---|
| WO | WO 2014/189854 A2 | 11/2014 |
| WO | WO 2014/189854 A9 | 2/2015 |

OTHER PUBLICATIONS

Berezin et al., "Fluorescence Lifetime Measurements and Biological Imaging", Chem Rev. May 12, 2010; 110(5): 2641-2684. doi: 10.1021/cr900343z. 2641-2684.*
Periasanny et al., "FRET Imaging of PIT-1 Protein Interactions in Living Cells", J. Biomed. Optics, Apr. 1998, 3(2): 154-160.*
Chen et al., "Fusion Protein Linkers: Property, Design and Functionality", Adv. Drug Deliv. Rev., 2013, Oct. 2013 (published on-line Sep. 29, 2012), 65(10):1357-1369.*
Axelrod, D., Chapter 12, Fluorescence Polarization Microscopy, Methods in Cell Biology, vol. 30, pp. 333-352, 1989.
Baird, G.S., et al., Circular permutation and receptor insertion within green fluorescent proteins, Proc. Natl. Acad. Sci. USA, vol. 96, pp. 11241-11246, 1999.
Cao, Z., et al., Nuclease resistance of telomere-like oligonucleotides monitored in live cells by fluorescence anisotropy imaging, Anal. Chem., vol. 78, No. 5, pp. 1478-1484, 2006.
Chapman, S., et al., The photoreversible fluorescent protein iLOV outperforms GFP as a reporter of plant virus infection, Proc. Natl. Acad. Sci. USA, vol. 105, pp. 20038-20043, 2008.
Chatwell, L., et al. Structure of lumazine protein, an optical transponder of luminescent bacteria, J. Mol. Biol., vol. 382, No. 1, pp. 44-55, 2008.
Chen, L., Reconstruction of the Fluorescent Protein iLOV2Prokaryotic Expression and Crystal Screening, Master's Thesis Executive Summary, Jilin University, pp. 1-3, 2013; Version submitted herewith downloaded on May 5, 2014.
Crosson, S., et al., Structure of a flavin-binding plant photoreceptor domain: insights into light-mediated signal transduction, Proc. Natl. Acad. Sci. USA, vol. 98, p. 2995, 2001.
Dix, J.A., et al., Mapping of fluorescence anisotropy in living cells by ratio imaging, Application to cytoplasmic viscosity, Biophys. J., vol. 57, No. 2, pp. 231-240, 1990.
Giepmans, B.N.G., et al., The fluorescent toolbox for assessing protein location and function, Science, vol. 312, pp. 217-224, 2006.
Heidecker, M., et al., Proximity relationships and structural dynamics of the phalloidin binding site of actin filaments in solution and on single actin filaments on heavy meromyosin, Biochemistry, vol. 34, No. 35, pp. 11017-11025, 1995.
Jameson, D.M., et al., Fluorescence Polarization/Anisotropy in Diagnostics and Imaging, Chem. Rev., vol. 110, pp. 2685-2708, 2010.
Jares-Erijman, E.A., et al., Imaging molecular interactions in living cells by FRET microscopy, Curr. Opin. Chem. Biol., vol. 10, p. 409, 2006.
Palmer, E., Using new fluorescent proteins to image bacterial biofilms under anaerobic conditions, The 6th Annual Univeristy of Notre Dame Undergraduate Scholars Conference and College of Science Joint Annual Meeting (COS-JAM), pp. 1-3, May 3, 2013.

(Continued)

Primary Examiner — Suzanne M Noakes
(74) Attorney, Agent, or Firm — Knobbe, Martens, Olson & Bear, LLP

(57) ABSTRACT

Isolated truncated and mutated sensor proteins derived from flavoproteins that are 12-20 KDa or less, genetically encoded for detection and imaging of protein complexes having long fluorescent lifetimes that can be 4.0 ns or greater.

15 Claims, 57 Drawing Sheets

Specification includes a Sequence Listing.

(56) References Cited

OTHER PUBLICATIONS

Kim, S.Y., et al., Purification and Characterization of the Amino-Terminal Domain of Luzamine Protein from Photobacterium leiognathi, Bull. Korean Chem. Soc., vol. 31, No. 4, pp. 1017-1020, 2010.
Lam, A., et al., Improving FRET dynamic range with bright green and red fluorescent proteins, Nature Methods, vol. 9, pp. 1005-1012, 2012.
Lee, J., et el., Spectral properties and function of two lumazine proteins from Photobacterium, Biochemistry, vol. 24, pp. 1476-1483, 1985.
Lin, J.W., et al., The luzamine protein-encoding gene in Photobacterium leiognathi is linked to the Lux operon, Gene, vol. 126, No. 1, pp. 153-154, 1993.
Mao, S., et al., Optical lock-in detection of FRET using genetically encoded optical switches: High contrast FRET imaging of protein interactions in living cells, Biophysical J., vol. 94, pp. 4515-4524, 2008.
Marriott, G., et al., Spectroscopic and Functional Characterization of an Environmentally Sensitive Fluorescent Actin Conjugate, Biochemistry, vol. 27, pp. 6214-6220, 1988.
Marriott, G., et al., Time-resolved Delayed Luminescence Image Microscopy Using Europium-Ion Chelates, Biophysical J., vol. 67, p. 957, 1994.
Mastro, A.M., et al., Diffusion of a small molecule in the cytoplasm of mammalian cells, Proc. Natl. Acad. Sci. USA, vol. 81, No. 11, pp. 3414-3418, 1984.
Mattheyses, A.L., Polarized fluorescence resonance energy transfer microscopy, Biophys. J., vol. 87, No. 4, pp. 2787-2797, 2004.
Mott, H.R., et al., Structure of the small G protein Cdc42 bound to the GTPasebinding domain of ACK, Nature, vol. 399, No. 6734, pp. 384-388, 1999.
Nalbant, P., et al., Activation of Endogenous Cdc42 Visualized in Living Cells, Science, vol. 305, pp. 1615-1619, 2004.
Owen, D., et al., Molecular dissection of the Interaction between the small G Proteins Rac1and RhoA and protein kinase C-related Kinase 1 (PRK1), J. Biol. Chem., vol. 278, pp. 50578-50587, 2003.
Pereira, J.H., et al., Crystallization and preliminary X-ray analysis of human Bm-5 transcription factor in complex with DNA, Acta Crystallogr. Sect. F Struct. Biol. Cryst. Commun., vol. 64, No. 3, pp. 175-178, 2008.
Petchprayoon, C., et al., Fluorescent Kabiramides: New Probes to Quantify Actin in vitro and in vivo, Bioconjugate Chem., vol. 16, pp. 1382-1389, 2005.
Rønnov-Jessen, L., et al., Breast cancer by proxy: can the microenvironment be both the cause and consequence?, Trends Mol. Med., vol. 15, p. 513, 2009.
Salomon, M., et al., Photochemical and mutational analysis of the FMN-binding domains of the plant blue light receptor, phototropin, Biochemistry, vol. 39, pp. 9401, 2000.
Sato, Y., et al., Crystal structures of the Lumazine Protein from Photobacterium kishitanii in complexes with the authentic chromophore, 6,7-dimethyl-8-(1'-D-Ribityl) Lumazine, and its analogues, Riboflavin and Flavin Mononucleotide, at high resolution, J. Bacteriology, vol. 192, pp. 127-133, 2009.
Strickland, D., et al., Light-activated DNA binding in a designed allosteric protein, Proc. Natl. Acad. Sci., vol. 105, No. 31, pp. 10709-10714, 2008.
Takagi, T., et al., Amino acid sequence studies on factor XIII and the peptide released during Its activation by thrombin, Biochemistry, vol. 13, No. 4, pp. 750-756, 1974.
Van Der Krogt, G.N.M., et al., A comparison of donoracceptor pairs for genetically encoded FRET sensors: Application to the Epac cAMP sensor as an example, PLoS One, vol. 3, No. 4, p. 1916, 2008.
Vilardaga, J.P., et al., Measurement of the millisecond activation switch of G protein-coupled receptors in living cells, Nat. Biotechnol., vol. 21, p. 807, 2003.
Visser, A.J., et al., Determination of rotational correlation times from deconvoluted fluorescence anisotropy decay curves. Demonstration with 6,7-dimethyl-8-ribityllumazine and lumazine protein from Photobacterium lelognathi as fluorescent indicators, Biochemistry, vol. 12, pp. 1489-1496, 1985.
Visser, A.J., et al., Fluorescence Properties of Reduced Flavins and Flavoproteins, European Journal of Biochemistry, vol. 101, pp. 13-21, 1979.
Visser, A.J., et al., Time resolved fluorescence of flavins and flavoproteins, Methods Enzymol., vol. 66, pp. 373-385, 1980.
Weber, G., Polarization of the fluorescence of macromolecules. II. Polarization of the fluorescence of labeled protein molecules, Blochem. J., vol. 51, pp. 155-164, 1952.
Wolfram Research, Mathematica (Wolfram Research, Inc., Champaign, IL), Version 10, 2015. URL: https://www.wolfram.com/mathematica/new-in-10/; Original publication date unknown; Version submitted herewith downloaded on Mar. 15, 2017.
Wu, Y., et al., A genetically encoded photoactivatable Rac controls the motility of living cells, Nature, vol. 461, pp. 104-110, 2009.
Yan, Y., et al., Analysis of Protein Interactions using Fluorescence Technologies, Curr. Opin. Chem. Biol., vol. 7, pp. 635-640, 2003.
Yan, Y., et al., Fluorescence resonance energy transfer imaging microscopy and fluorescence polarization imaging microscopy, Methods in Enzymology., vol. 360, pp. 561-580, 2003.
International Preliminary Report on Patentability, dated Dec. 22, 2014, in International Application No. PCT/US2014/038644.
International Search Report, dated Dec. 22, 2014, in International Application No. PCT/US2014/038644.
Dale et al., The Orientational Freedom of Molecular Probes: The Orientation Factor in Intramolecular Energy Transfer, Biophys. Journal, vol. 26, pp. 161-194, May 1979.
FluorTools (2014) UV-Vis-IR Spectral Software, Version 1.2, Available at www.fluortools.com. Accessed Nov. 28, 2017.
Hoepker et al., Genetically-encoded Sensors of Protein Hydrodynamics, Oncotarget, vol. 9, No. 19, pp. 16808-16809, Jul. 2015.
Hoepker et al., Genetically-encoded Sensors of Protein Hydrodynamics and Molecular Proximity, PNAS, May 19, 2015;112(20):E2569-74. doi: 10.1073/pnas.1424021112. Epub Apr. 30, 2015.
Jablonski, A., On the Notion of Emission Anistropy, Bull Acad Poi Sci Biol, vol. 8, pp. 259-264, 1960.
Laine et al., Fluorescence Lifetime Readouts of Troponin-C-Based Calciu, FRET Sensors: A Quantitative Comparison of CFP and mTFP1 as Donor Fluorophores, PLOS, vol. 7, No. 11, Nov. 2012.
Sarker et al., Photophysical Properties of Cerulean and Venus Fluorescent Proteins, J Biomed Opt, vol. 14, No. 3, 2009.
Valour, B., Effect of Brownian Motion, Molecular Fluorescence Principles and Applications, V. 5.6, pp. 140-143, 2001.
Van Der Krogt et al., A Comparison of Donor-Acceptor Pairs for Genetically Encoded FRET Sensors: Application to the Epac cAMP Sensor as an Example, PLOS One, vol. 3, No. 4, Apr. 2008.
Vicidomini et al., STED Nanoscopy with Time-Gated Detection: Theoretical and Experimental Aspects, PLOS One, vol. 8, No. 1, Jan. 2013.
Volkmer et al., One-and Two-Photon Excited Fluorescence Lifetimes and Anisotropy Decays of Green Fluorescent Proteins, Biophys J, vol. 78, pp. 1589-1598, Mar. 2000.
Haynes, W.M., et al., CRC Handbook of Chemistry and Physics, 94th Ed, CRC Press, Boca Raton, FL, 2013.
Jameson, D.M., Introduction to Fluorescence, CRC Press, Boca Raton, FL, pp. 75-99, 2014.
Nagai, T., et al, A variant of yellow fluorescent protein with fast and efficient maturation for cell-biological applications, Nature Biotechnology, vol. 20, No. 1, pp. 87-90, Jan. 2002.
Office Action, dated Sep. 20, 2017, in European Patent Application No. 14801287.5.
Office Action, dated Nov. 2, 2017, in Australian Patent Application No. 2014268797.
Office Action, dated Feb. 6, 2018, in European Patent Application No. 14801287.5.
Anonymous: "UNIPROT:Q06877", Feb. 1, 1995 (Feb. 1, 1995), XP055305074, Retrieved from the internet: URL:http://ibis/exam/dbfetch.jsp?id=UNIPROT:O06877 [retrieved on Sep. 23, 2016] *sequence*.

* cited by examiner

Excitation and Emission spectra For fLov2

LUMP - *P. leioghnati* (20 kD)

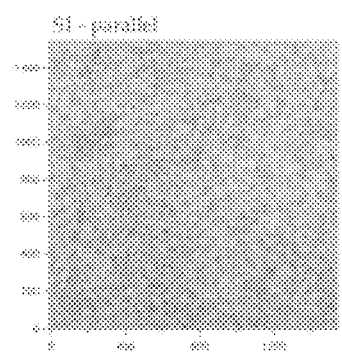 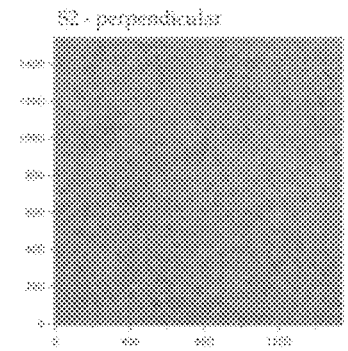 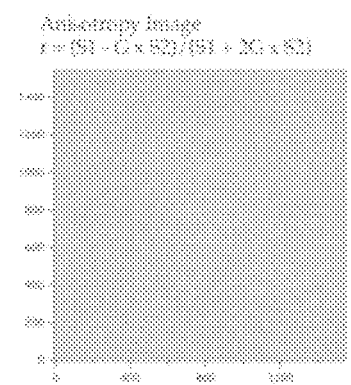
FIG. 6A  FIG. 6B  FIB. 6C

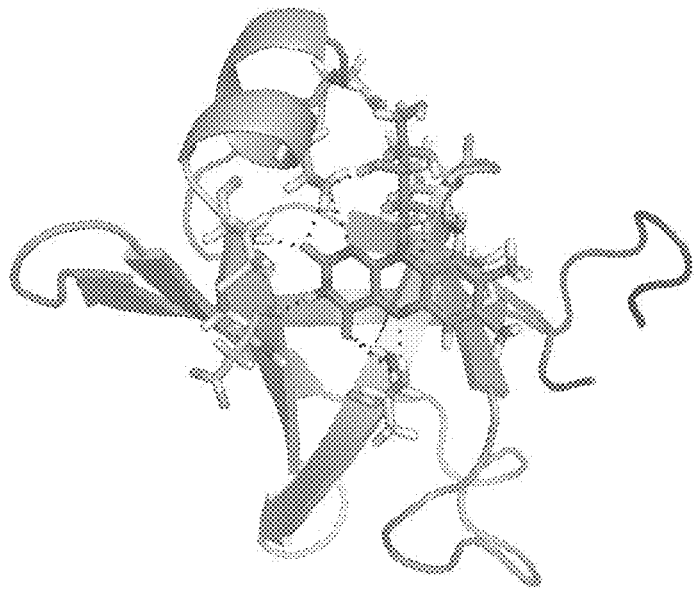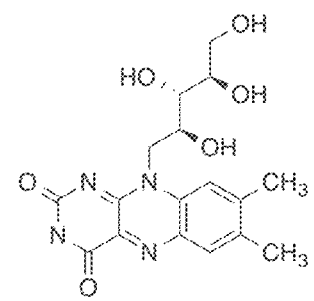
cofactor: Riboflavin
N-terminal RS (1-88) dimerizes– N72, N83, N45
Monomeric with N72D/N83A mutations
(1) flavin is brighter and redder than lumazine
(2) flavin binds to RS at the surface,
Figure 9

FIG. 11A amino acid sequence of Y1:

MFKGIVEGIGIIEKIDIYTDLDKYAIRFPENMLNGIKKESSIMFNGCFLTVTSVNSNIVWFDIFEKEARKLDTFR
EYKVGDRVNLGTFPKFGAASGGHILSARISCVASIIEIIENEDYQQMWIQIPENFTEFLIDKDYIAVDGISLTID
TIKNNQFFISLPLKIAQNTNMKWRKKGDKVNVELSNKINANQCW (SEQ ID NO: 12)

nucleic acid sequence of Y1:

```
  1 aatattttta ttaattcatt agaaaaatga gaggaaggat tattatgttt aaaggtatag    61
    tagaaggtat aggaatcatt gaaaaaattg atatatatac tgacctagat aagtatgcaa   121
    ttcgatttcc tgaaaatatg ttgaatggaa ttaaaaagga gtcgtcaata atgtttaacg   181
    gatgcttctt aacggtaact agcgtgaatt caaacattgt ctggtttgat atatttgaaa   241
    aagaagcacg taagcttgat acttttcggg aatataaggt aggtgaccga gtaaatttag   301
    gaacattccc aaaatttggc gctgcatctg gtgggcatat attatcagca aggatttcat   361
    gtgtagcaag tattattgaa ataatagaaa atgaggatta tcaacaaatg tggattcaaa   421
    ttcctgaaaa ttttacagag tttcttattg ataaagacta tattgctgtg gatggtatta   481
    gcttaactat tgacactata aaaaacaacc aattttcat tagtttaccc ttaaaaatag    541
    cacaaaatac aaatatgaaa tggcgaaaaa aaggtgataa ggtaaatgtt gagttatcaa   601
    acaaaattaa tgctaaccag tgttggtaat ttactgagga tagtaaaaat gaactgttta   661
    aaataatatt taaattttta tttataatac agagtcagtt gttgtaaata gtctgagtgg   721
    taaataagtt ctaccattaa ttaaatatta tccatattaa ataaggatc t         (SEQ ID NO: 13)
```

FIG. 11B

N-RFS (native) – residues 1-97
MFTGIVQGTAKLVSIDEKPNFRTHVVELPDHMLDGLETGASVAHNGCCLTVTEINGNHV
SFDLMKETLRITNLGDLKVGDWVNVERAAKFSDEIGGH
(SEQ ID NO: 10)

mutated, monomeric N-RFS (N72D/N83A):
MGSSHHHHHHDYDIPTTENLYFQGHMFTGIVQGTAKLVSIDEKPNFRTHVVELPDHML
DGLETGASVAHNGCCLTVTEINGNHVSFDLMKETLRITDLGDLKVGDWVAVERAAKFS
DEIGGH*
(SEQ ID NO: 11)

FIG. 11C

```
MASKGAGGGG GGHEEPQRPK QQLPRDSRGS LEVFNPSSSS AAVEPPSAFR PAARSASPFI
        70         80         90        100        110        120
EEATGGIEDV GKATQRAAEW GLVLQTNEQT GRPQGVSARS SGGGGSARSS SDDKAVAGAI
       130        140        150        160        170        180
PRVSEELRAA LSAFQQTFVV SDASRPGHPI MYASAGFFNM TGYTSKEVVG PNCRFLQGSG
       190        200        210        220        230        240
TDPAEIAKIR QALANGSNYC GRVLNYKKDG TAFWNLLTIA PIKDEEGRVL KFIGMQVEVS
       250        260        270        280        290        300
KYTEGNKDTV VRFNGLPESL IKYDARQKDQ ARSSVSELLL AIKNPRSLSE STNSTFKRKS
       310        320        330        340        350        360
QESVGALTGD RPGKRSSESG SRRNSKSGAR TSLQKISEVP ERGSKSRKSG LYSLMSLLGM
       370        380        390        400        410        420
GPGNIEKDML KPRDEDPLLD SDDERPESFD DELPRKEMRR GIDLATTLER IEKNFVITDP
       430        440        450        460        470        480
RLPDNPIIFA SDSFLQLTEY SREEILGRNC RFLQGPETDR ATVRKIRDAI DNQTEVTVQL
       490        500        510        520        530        540
INYTKSGKKF WNLFHLQPMR DQKGDVQYFI GVQLDGTERV RDAAEREGVM LIKKTAENID
       550        560        570        580        590        600
EAAKELPDAN LRFEDLWANH SKVVLFKPHM KDSASWRAIQ KVLEGGENID LKHFRPVKPL
       610        620        630        640        650        660
GSGDTGSVRL VELLNTGEYF AMKAMDKNVM LNRNKVHRAN AEREILDMLD HPFLPTLYAS
       670        680        690        700        710        720
FQTKTHICLI TDYYPGGELF LLLDRQPLKV LREDAVRFYA AEVVIALEYL HCQGIIYRDL
       730        740        750        760        770        780
KPENILLHRD GHISLTDFDL SCLTSCRPQV FLPEEANKKS RRKSRSSPIF FAEPMRASNS
       790        800        810        820        830        840
FVGTEEYIAP EIITGAGHTS AVDWWALGIL LYEMLYGYTP FRGKTRQRTF ANILHKDIRF
       850        860        870        880        890        900
PASISVSLPA RQLIYRLLHR DPSNRLGSYE GSNEIKEHPF FRGINWALVR GTAPPKLDAP
       910        920
LFPDDTDKGM GDAAAADTHT DMF     (SEQ ID NO: 1)
```

FIG. 11D

```
   1 aggtcgacac tagtggatcc aaagaattcn ggcacgagcc ccccaattcc cttcgtccca
  61 cggccatgcc gcgcggtctt ccgagcgggc atatacgtac cctagctacg cgcgcagcaa
 121 gcatctactg tgcagatcgc ctctcgcttc acgcgcaccg gcgcaaaggc tagccaagtg
 181 ctcgctgcct ctgcccgtc tgacctctc ttcctagcta gctccctcgt agagtccact
 241 gggcactgct cgcgagcaga taaagaaata tagtgggatg gagagctgag gtgcgtgcgg
 301 ttttaggttc ttggatcacg cgccagcgag cacgccaaga tagaaggagg aggaaggaag
 361 agtcgctgct actggctgc tatttagctg aagcttcaca tcaatggctt ccaaaggtgc
 421 aggaggcggc ggcggcggcc atgaggagcc tcagcggccg aagcagcagc tgccgcgcga
 481 ctccgcggc tcgctcgagg tcttcaaccc ctcttcctcc tccgccgccg tcgagcccc
 541 ctccgcgttc cgcccgccg ccaggtccgc ctcccgttc atcgaggaag caacgggcgg
 601 catcgaggat gtcggcaagg ccacgcagcg ggcggcggag tgggcctcg tgctccagac
 661 caacgagcag acgggccggc cgcagggcgt gtccgccga tcctccggag gcggcggctc
 721 cgccgcagc agctccgacg acaaggccgt cgccggcgcc atccccggg tctcggagga
 781 gctccgggcc gcgtctccg cgttccagca gaccttcgtc gtgtcggacg ccagccgacc
 841 cggccaccca atcatgtacg ccagcgcgg cttcttcaac atgaccggct acacatccaa
 901 ggaggtcgtc ggaaggaact gccgcttcct ccaaggctcc ggcaccgacc cggcggagat
 961 tgccaagatc aggcaggctc tagcaaatgg atcaaactac tgcggccgtg tcctcaacta
1021 caagaaggac ggcaccgcat tctggaacct cttgaccatt gcccaatca aggatgaaga
1081 aggcagggtc ctcaagttca tagggatgca agtggaagta agtaaataca ctgaagggaa
1141 caaggatacg gttgttcgtc caaatggcct gccagagtca ctcatcaaat atgatgccag
1201 gcaaaaggat caggcccgta gctcagtgtc tgagcttctg ttggcatca agaatccacg
1261 atcattgtca gaatcaacta atagcacctt taaaagaaaa tcacaggaat cagtaggtgc
1321 attgacgggt gatcgtcctg gcaagagaag ctcagaaagt ggatctcgac gtaactcaaa
1381 atctggagca agaacctcac tgcaaaagat cagcgaagta cctgaaagag gcagtaaaag
1441 tagaaaatct ggtctgtatt cacttatgag tttacttggt atgggcctg gaaatataga
1501 aaggacatg ctgaaaccaa gagatgaaga cccgctactt gacagtgatg atgaaagacc
1561 tgagagtttt gatgatgagc taaggcggaa agaaatgaga aggggtatag acttggctac
1621 tacacttgaa cgtattgaga agaactttgt cattactgac ccaaggttgc cagataatcc
1681 cattatattc gcgtccgata gtttcttgca gttgacagaa tatagccgtg aagaaattt
1741 gggaagaaac tgcaggtttc tacaaggtcc tgaaactgat cgcgcgacag tgagaaaaat
1801 tagagatgcc atagataacc aaacagaggt cactgttcag ctgattaatt atacaaagag
1861 tggtaaaaag ttctggaacc tctttcactt gcagcctatg cgagatcaga agggagatgt
1921 ccagtacttt attggggttc agttggatgg aactgagcat gtccgagatg ctgccgagag
1981 agagggagtc atgctgatta agaaaactgc agaaaatatt gatgaggcgg caaaagaact
2041 tccagatgct aatttgagac cagaggattt gtgggctaac cactcaaaag tagttttgcc
2101 aaagccacat atgaaggatt ctgcatcatg gagagccatc caaaagttc ttgagggtgg
2161 agaaaacatt gatttgaagc atttcaggcc tgtaaagcct tgggatctg gtgacactgg
2221 aagcgtgcac ttggtggagt tattaaacac aggtgaatac tttgccatga agctatgga
2281 taaaaacgtc atgcttaacc gcaataaggt tcatagagct aacgctgaac gagaaatcct
2341 tgatatgttt gatcacccat tccttccgac attatatgcg tcatttcaga caaagacaca
2401 tatatgtctc attacagact actaccctgg cgggagctc tttctgctcc tagatagaca
2461 acctctaaag gttctgcggg aagatgccgt caggttctat gctgctgaag ttgtcattgc
2521 acttgaatac ttgcattgcc aaggaatat ctaccgagac ttgaagccag agaatatctt
2561 acttcacagg gacgggcaca tctccttgac agactttgat ttgtcttgtc tgacatcttg
2641 cagaccgcag gtctttcttc cagaagaagc taataagaaa agtaggagga aaagcaggag
2701 ttcaccccata tttttgctg aacctatgcg agcatccaat tcatttgttg gtacagagga
2761 gtacattgca cctgagatca ttactggagc tggccataca agtgctgttg attggtgggc
2821 gctagggatc ctcctgtatg aaatgttgta tggttacaca cccttcagag gtaaaaccag
2881 gcagaggaca ttcgccaaca tcctacacaa ggacatcaga tttccgcga gtatatcggt
2941 gagcctccca gcaaggcagc tgatatatag gctgctacac agggatcctt cgaataggct
3001 gggatcgtac gagggatcaa acgagataaa agaacaccct tcttccgcg gcatcaactg
3061 ggctctcgtg cgtggcacgg ctcctccaaa gctggacgct ccactgttcc cggatgacac
3121 ggacaaggga atgggcgatg ctgctgctgc tgatactcac acgacatgt tctgaatgaa
3181 gaagctggct tggataaaaa cgcatctcga tcaagctcaa tcatgcatgc atgttttgt
3241 ttgttgttga tagctgctgt ttactactgc ctaggattgt aggaataatt aagctagcct
```

```
3301 gggatcgctg gatgtaatgt aatgtattgt actgcgtgta tttggatcgt gcttaaataa
3361 taatcaagtt cagccaaaaa aaaaaaaaaa aaaactcnga gagtacttct agagcggccg
3421 cgggcccatc gattttccac ccgggtgggt accagtaatt acccaat   (SEQ ID NO: 2)
```

GHMASE[NFVTCDPRLFDNPTTFAIDSTLQITRSRPRILGRHRFLQQFBTDNATYKK IBAIDRQTRVTVQLINYTKSGANFWILTHLQPMRLCKGDVQIFIGEQLL] (SEQ ID NO:3)

FIG. 11F

MASEKNFVICDPRLPDNPIIFASDSFLQLTEYSREEILGRNARFLQGPETDRATVRKIR
DAIDNQTEVTVQLINYTKSGKKFWNLFHLQPMRDQKGDVQYFIGVQLD (SEQ ID
NO:4)

FIG. 11G

```
         10          20          30          40          50          60
MFRGIVQGRG  VIPSISKSED  SQRHGIAFPE  GMFQLVDVDT  VMLVNGCSLT  VVRILGDMVY 70          80          90         100         110         120
FDIDQALGFT  TFDGLKEGDQ  VNLEIHPKFG  EVVGRGGLTG  NIKGTALVAA  IEENDAGFSV 130         140         150         160         170         180
LIDIPKSLAE  NLTVKDDIGI  DGISLPITDM  SDSIITLNYS  RDLLASTNIA  SLAKDVKVNV

EILNEW  (SEQ ID NO: 6)
```

FIG. 11H

```
   1 ctgcagcagt taatcactac cattcattta aatttcaac gttcacttc acatcttttg
  61 ctaacgatgc aatgttagta ctcgctaaca aatcacgcga gtaattcaat gtaataatgc
 121 tgtctgacat atcagtgata ggcaaagaga tccatcaat tcaatatca tctttcactg
 181 ttaagttttc agctaaccct ttagggatat caatcagtac agaaaaacct gcgtcattct
 241 cttctattgc tgcgaccagc gcagtgcctt taatatttcc tgttaatcca ccacggcaaa
 301 ccacttcacc aaatttaggg tggatctcta ggtttacctg atcgccttct tttaatccat
 361 caaatgttgt cgtacccaat gcttggtcga tatcaaagta caccatatcg cctaaaatac
 421 ggacaactgt caatgaacaa ccatttacta acattacagt atctacatca acaagttgaa
 481 acatacccct agggaatgca atccatgtc gctgactatc ttcacttttt gaaatggatc
 541 gaataacacc acgaccttga acaatacctc taaacattac tgtctcctt tttagactct
 601 atatgatatt ttcagtaaaa atacaactag cacatttatg agattctagt aattgaagaa
 661 agaaatacaa aagcggaca acatttttct attaccatca caattttttt aattaaacaa
 721 tattaaaatc aatcttgtat taacaatgaa atatcaataa tattttaatg ggcaattgaa
 781 acattattca ttttacattc caattgaacg ctatataaac aattccagcc aatacccatc
 841 aaaaatcccc ttacccccaat aaaaataaa taaaaacaaa taaaaatcaa caacttaaca
 901 aacaaaacca ccagcagata cttgctaaaa tccgtatata aaggttgag taatatttac
 961 ctaataaaaa taaaatctat tattaaaact taaaaaaatac aaaacaaaat actgtttaat
1021 taaataaaaa acaccggagt aaatataaa taaaaatata aataaagtt caaaatataa
1081 ccaaaaagct taaatttaca tttataaaaa atcatagaaa taataaacac aataaattcc
1141 gcactgcatt ctatattttt tagaacgatt tttaagcaca tataagtgta aaaaaaactg
1201 ggcagagtaa atataaaaac catgaattaa aaataatatt gtcaacaatg tgagccaaat
1261 ctcaaaacgt aacaaatgca aaacaattta cttacactaa aaaaaatatt ctcctagcct
1321 aatttcattc cctatgcagc atgcgactat gcaattaggg tatataaaac ttacaatatg
1381 ctaatggaga ttgcatgatt aaaaagatcc cactgattat tggaggcgaa gttcaagaca
1441 cgtcagaaca tgatgtccgt gaacttacgc ttaacaataa caccgtcaat gtacctatca
1501 ttacggacaa agatgctgaa tctatcacct cactaaaaat agaaataag ttaaatatca
1561 accagatagt taacttcttg tatactgtag ggcaaaaatg gaagagtgag aactacagcc
1621 gtcgcctcac ttatattcgt gatctagtaa aattcatggg ctactcccct gagatggcaa
1681 aactagaagc gaactggatt tcgatgattc tatgtagcaa aagtgcgcta tatgacattg
1741 ttgaaaatga tctcagctct cgtcatattg ttgatgaatg gctcccccaa ggtgattgct
1801 atgttaaagc gctaccaaaa ggtaaatcta tccatttatt agcgggtaac gttccgctat
1861 caggtgtgac atcgatcctg cgtgcaattt taactaaaaa tgaatgtatc attaaaacat
1921 catctgcag     (SEQ ID NO: 7)
```

FIG. 11I

GHMFRGIVQGRGVIRSISKSEDSQRHGIAFPEGMFQLVDVDTVMLVNGCSLTVVRILGD
MVYFDIDQALGTTTFDGLKEGDQVNLEIHPKFGEVVGRGGLTGNI (SEQ ID NO:8)

FIG. 11J

GHMFRGIVQGRGVIRSISKSEDSQRHGIAFPEGMFQLVDVDTVMLVNGCSLTVVRILGD
MVYFDIDQALGTTTFDGLKEGDQVNLEIHPKFGEVVGRGGLTGNIKGTALVAAIEENDA
GFSVLIDIPKGLAENLTVKDDIGIDGISLPITDMSDSIITLNYSRDLLASTNIASLAKD
VKVNVEILNEW (SEQ ID NO:9)

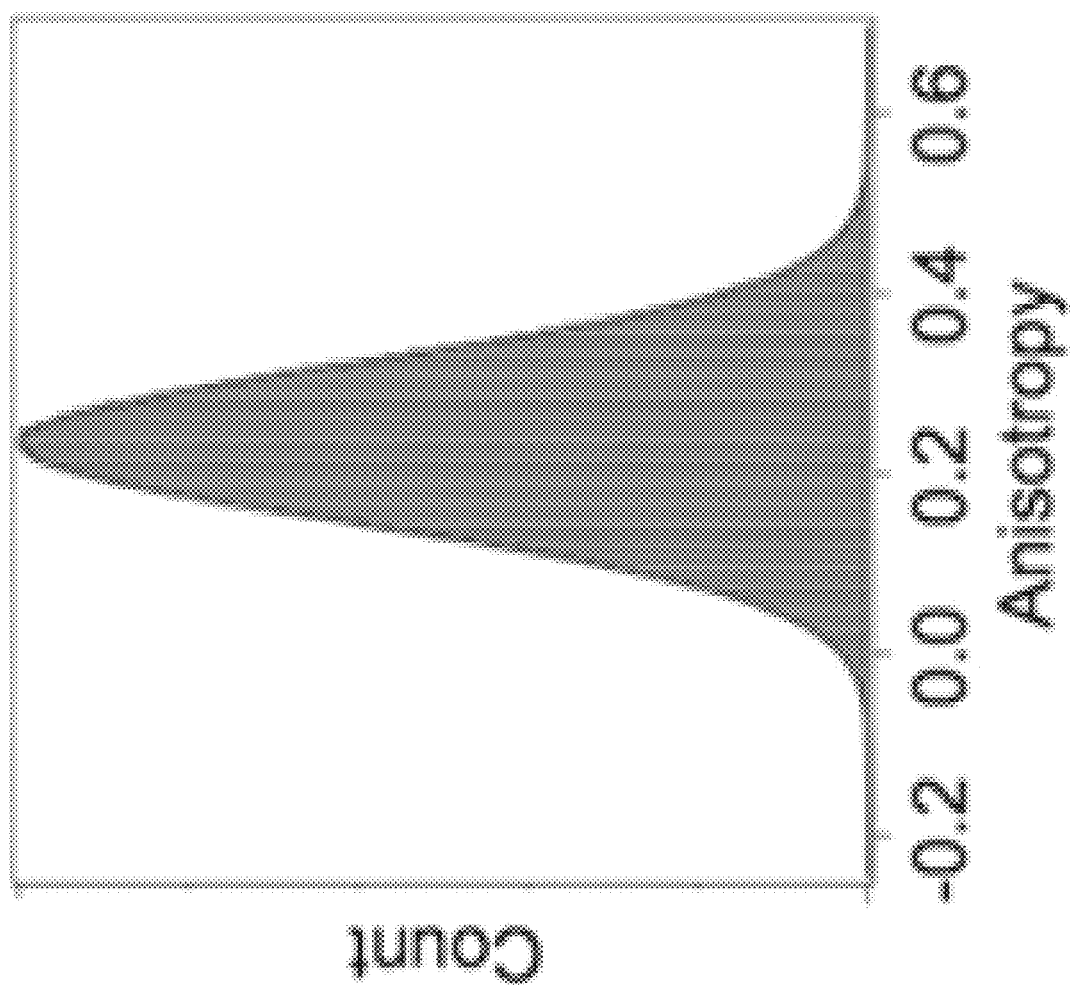

FIG. 22

MGSSHHHHHHDYDIPTTENLYFQ//GHMFRGIVQGRGVIRSISKSEDSQRHGIAFPEGMFQ
LVDVDTVMLVNGCSLTVVRILGDMVYFDIDQALGTTFDGLKEGDQVNLEIHPKFGEVVGR
GGLTGNIKGTALVAAIEENDAGFSVLIDIPKGLAENLTVKDDIGIDGISLPITDMSDSIITLNYS
RDLLASTNIASLAKDVKVNVEILNEW (SEQ ID NO: 14)

FIG. 23

MGSSHHHHHHDYDIPTTENLYFQ//GHMGLSAQDISQPLQNSFIHTGHGDSDPRHCWGFPDRIDELYLGNGSGSASFRGIVQGRGVIRSISKSEDSQRHGIAFPEGMFQLVDVDTVMLVNGCSLTVVRILGDMVYFDIDQALGTTFDGLKEGDQVNLEIHPKFGEVVGRGGLTGNIKGTALVAAIEENDAGFSVLIDIPKGLAENLTVKDDIGIDGISLPITDMSDSIITLNYSRDLLASTNIASLAKDVKVNVEILNEW (SEQ ID NO: 15)

FIG. 24

MGSSHHHHHHDYDIPTTENLYFQ//GHMVSKGEELFTGVVPILVELDGDVNGHKFSVSGEG
EGDATYGKLTLKFICTTGKLPVPWPTLVTTFGYGLMCFARYPDHMKQHDFFKSAMPEGYV
QERTIFFKDDGNYKTRAEVKFEGDTLVNRIELKGIDFKEDGNILGHKLEYNYNSHNVYIMAD
KQKNGIKVNFKIRHNIEDGSVQLADHYQQNTPIGDGPVLLPDNHYLSYQSALSKDPNEKRD
HMVLLEFVTAAGITLGMDELYKASFRGIVQGRGVIRSISKSEDSQRHGIAFPEGMFQLVDV
DTVMLVNGCSLTVVRILGDMVYFDIDQALGTTFDGLKEGDQVNLEIHPKFGEVVGRGGLT
GNIKGTALVAAIEENDAGFSVLIDIPKGLAENLTVKDDIGIDGISLPITDMSDSIITLNYSRDLL
ASTNIASLAKDVKVNVEILNEW (SEQ ID NO: 16)

MGSSHHHHHHDYDIPTTENLYFQ//GHMVSKGEELFTGVVPILVELDGDVNGHKFSVSGEG
EGDATYGKLTLKFICTTGKLPVPWPTLVTTFGYGLMCFARYPDHMKQHDFFKSAMPEGYV
QERTIFFKDDGNYKTRAEVKFEGDTLVNRIELKGIDFKEDGNILGHKLEYNYNSHNVYIMAD
KQKNGIKVNFKIRHNIEDGSVQLADHYQQNTPIGDGPVLLPDNHYLSYQSALSKDPNEKRD
HMVLLEFVTAAGITLGMDELYKASLVPRGSRGSFRGIVQGRGVIRSISKSEDSQRHGIAFP
EGMFQLVDVDTVMLVNGCSLTVVRILGDMVYFDIDQALGTTFDGLKEGDQVNLEIHPKF
GEVVGRGGLTGNIKGTALVAAIEENDAGFSVLIDIPKGLAENLTVKDDIGIDGISLPITDMSD
SIITLNYSRDLLASTNIASLAKDVKVNVEILNEW (SEQ ID NO: 17)

The full amino acid sequence of the thrombin substrate (including the His-tag) is:

HHHHHHGMASMTGGQQMGRDLYENLYFQGSSMVSKGEELIKENMRMKVVMEGSVNGHQFKCTGEGEGNPYMGTQTMRIKV
IEGGPLPFAFDILATSFMYGSRTFIKYPKGIPDFFKQSFPEGFTWERVTRYEDGGVVTVMQDTSLEDGCLVYHVQVRGVNFPSNGPV
MQKKTKGWEPNTEMMYPADGGLRGYTHMALKVDGGGHLSCSFVTTYRSKKTVGNIKMPGIHAVDHRLERLEESDNEMFVVQRE
HAVAKFAGLGGGMDELYKGSLVPRGSASEKNFVICDPRLPDNPIIFASDSFLQLTEYSREEILGRNARFLQGPETDRATVRKIRDAIDN
QTEVTVQLINYTKSGKKFWNLFHLQPMRDQKGDVQYFIGVQLD (SEQ ID NO: 26)

FIG. 27D

After cleavage with thrombin the fragment bearing mRuby2 is:

HHHHHHGMASMTGGQQMGRDLYENLYFQGSSMVSKGEELIKENMRMKVVMEGSVNGHQFKCTGEGEGNPYMGTQTMRIKV
IEGGPLPFAFDILATSFMYGSRTFIKYPKGIPDFFKQSFPEGFTWERVTRYEDGGVVTVMQDTSLEDGCLVYHVQVRGVNFPSNGPV
MQKKTKGWEPNTEMMYPADGGLRGYTHMALKVDGGGHLSCSFVTTYRSKKTVGNIKMPGIHAVDHRLERLEESDNEMFVVQRE
HAVAKFAGLGGGMDELYKGSLVPR (SEQ ID NO: 27)

FIG. 27E

After cleavage, the fragment bearing fLov2 is :

GSASEKNFVICDPRLPDNPIIFASDSFLQLTEYSREEILGRNARFLQGPETDRATVRKIRDAIDNQTEVTVQLINYTKSGKKFWNLFHLQ
PMRDQKGDVQYFIGVQLD (SEQ ID NO: 28)

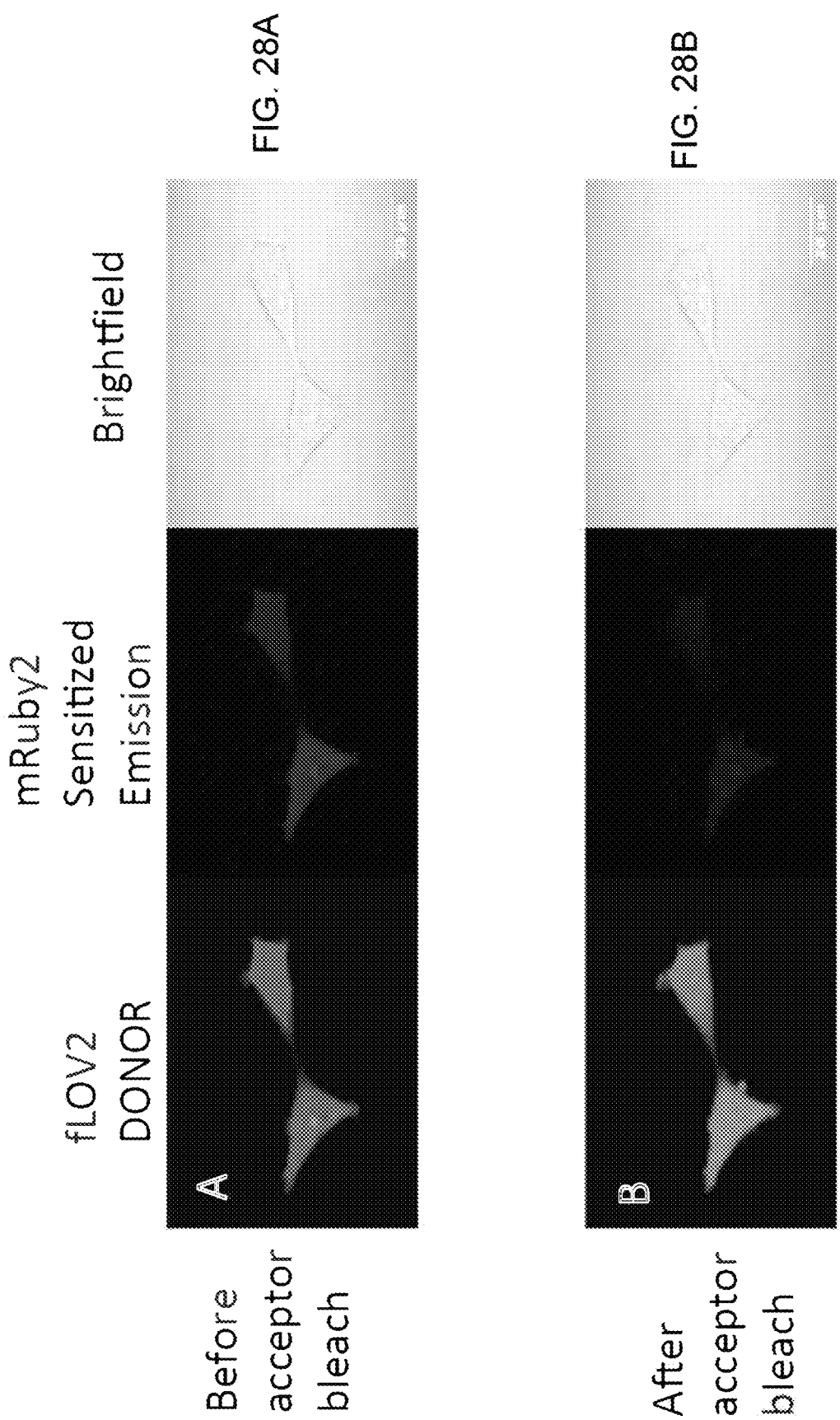

SEQUENCE LISTING

<160> NUMBER OF SEQ ID NOS: 31

<210> SEQ ID NO 1
<211> LENGTH: 923
<212> TYPE: PRT

<213> ORGANISM: Avena sativa
<220> FEATURE:
<223> OTHER INFORMATION: NPH1-1

<400> SEQUENCE: 1

```
Met Ala Ser Lys Gly Ala Gly Gly Gly Gly His Glu Glu Pro
1               5                   10                  15

Gln Arg Pro Lys Gln Gln Leu Pro Arg Asp Ser Arg Gly Ser Leu Glu
            20                  25                  30

Val Phe Asn Pro Ser Ser Ser Ala Ala Val Glu Pro Pro Ser Ala
                35                  40                  45

Phe Arg Pro Ala Ala Arg Ser Ala Ser Pro Phe Ile Glu Glu Ala Thr
    50                  55                  60

Gly Gly Ile Glu Asp Val Gly Lys Ala Thr Gln Arg Ala Ala Glu Trp
65                  70                  75                  80

Gly Leu Val Leu Gln Thr Asn Glu Gln Thr Gly Arg Pro Gln Gly Val
                85                  90                  95

Ser Ala Arg Ser Ser Gly Gly Gly Ser Ala Arg Ser Ser Ser Asp
                100                 105                 110

Asp Lys Ala Val Ala Gly Ala Ile Pro Arg Val Ser Glu Glu Leu Arg
            115                 120                 125

Ala Ala Leu Ser Ala Phe Gln Gln Thr Phe Val Val Ser Asp Ala Ser
130                 135                 140

Arg Pro Gly His Pro Ile Met Tyr Ala Ser Ala Gly Phe Phe Asn Met
145                 150                 155                 160

Thr Gly Tyr Thr Ser Lys Glu Val Val Gly Arg Asn Cys Arg Phe Leu
                165                 170                 175

Gln Gly Ser Gly Thr Asp Pro Ala Glu Ile Ala Lys Ile Arg Gln Ala
            180                 185                 190

Leu Ala Asn Gly Ser Asn Tyr Cys Gly Arg Val Leu Asn Tyr Lys Lys
            195                 200                 205

Asp Gly Thr Ala Phe Trp Asn Leu Leu Thr Ile Ala Pro Ile Lys Asp
210                 215                 220

Glu Glu Gly Arg Val Leu Lys Phe Ile Gly Met Gln Val Glu Val Ser
225                 230                 235                 240

Lys Tyr Thr Glu Gly Asn Lys Asp Thr Val Val Arg Pro Asn Gly Leu
                245                 250                 255

Pro Glu Ser Leu Ile Lys Tyr Asp Ala Arg Gln Lys Asp Gln Ala Arg
            260                 265                 270

Ser Ser Val Ser Glu Leu Leu Leu Ala Ile Lys Asn Pro Arg Ser Leu
            275                 280                 285

Ser Glu Ser Thr Asn Ser Thr Phe Lys Arg Lys Ser Gln Glu Ser Val
            290                 295                 300

Gly Ala Leu Thr Gly Asp Arg Pro Gly Lys Arg Ser Ser Glu Ser Gly
305                 310                 315                 320

Ser Arg Arg Asn Ser Lys Ser Gly Ala Arg Thr Ser Leu Gln Lys Ile
                325                 330                 335

Ser Glu Val Pro Glu Arg Gly Ser Lys Ser Arg Lys Ser Gly Leu Tyr
            340                 345                 350

Ser Leu Met Ser Leu Gly Met Gly Pro Gly Asn Ile Glu Lys Asp
            355                 360                 365

Met Leu Lys Pro Arg Asp Glu Asp Pro Leu Leu Asp Ser Asp Glu
            370                 375                 380

Arg Pro Glu Ser Phe Asp Asp Glu Leu Arg Arg Lys Glu Met Arg Arg
```

```
385                 390                 395                 400
Gly Ile Asp Leu Ala Thr Thr Leu Glu Arg Ile Glu Lys Asn Phe Val
                405                 410                 415

Ile Thr Asp Pro Arg Leu Pro Asp Asn Pro Ile Ile Phe Ala Ser Asp
            420                 425                 430

Ser Phe Leu Gln Leu Thr Glu Tyr Ser Arg Glu Ile Leu Gly Arg
        435                 440                 445

Asn Cys Arg Phe Leu Gln Gly Pro Glu Thr Asp Arg Ala Thr Val Arg
    450                 455                 460

Lys Ile Arg Asp Ala Ile Asp Asn Gln Thr Glu Val Thr Val Gln Leu
465                 470                 475                 480

Ile Asn Tyr Thr Lys Ser Gly Lys Lys Phe Trp Asn Leu Phe His Leu
            485                 490                 495

Gln Pro Met Arg Asp Gln Lys Gly Asp Val Gln Tyr Phe Ile Gly Val
        500                 505                 510

Gln Leu Asp Gly Thr Glu His Val Arg Asp Ala Ala Glu Arg Glu Gly
    515                 520                 525

Val Met Leu Ile Lys Lys Thr Ala Glu Asn Ile Asp Glu Ala Ala Lys
    530                 535                 540

Glu Leu Pro Asp Ala Asn Leu Arg Pro Glu Asp Leu Trp Ala Asn His
545                 550                 555                 560

Ser Lys Val Val Leu Pro Lys Pro His Met Lys Asp Ser Ala Ser Trp
            565                 570                 575

Arg Ala Ile Gln Lys Val Leu Glu Gly Gly Glu Asn Ile Asp Leu Lys
        580                 585                 590

His Phe Arg Pro Val Lys Pro Leu Gly Ser Gly Asp Thr Gly Ser Val
    595                 600                 605

His Leu Val Glu Leu Leu Asn Thr Gly Glu Tyr Phe Ala Met Lys Ala
    610                 615                 620

Met Asp Lys Asn Val Met Leu Asn Arg Asn Lys Val His Arg Ala Asn
625                 630                 635                 640

Ala Glu Arg Glu Ile Leu Asp Met Leu Asp His Pro Phe Leu Pro Thr
            645                 650                 655

Leu Tyr Ala Ser Phe Gln Thr Lys Thr His Ile Cys Leu Ile Thr Asp
        660                 665                 670

Tyr Tyr Pro Gly Gly Glu Leu Phe Leu Leu Asp Arg Gln Pro Leu
    675                 680                 685

Lys Val Leu Arg Glu Asp Ala Val Arg Phe Tyr Ala Ala Glu Val Val
    690                 695                 700

Ile Ala Leu Glu Tyr Leu His Cys Gln Gly Ile Ile Tyr Arg Asp Leu
705                 710                 715                 720

Lys Pro Glu Asn Ile Leu Leu His Arg Asp Gly His Ile Ser Leu Thr
            725                 730                 735

Asp Phe Asp Leu Ser Cys Leu Thr Ser Cys Arg Pro Gln Val Phe Leu
        740                 745                 750

Pro Glu Glu Ala Asn Lys Lys Ser Arg Arg Lys Ser Arg Ser Ser Pro
    755                 760                 765

Ile Phe Phe Ala Glu Pro Met Arg Ala Ser Asn Ser Phe Val Gly Thr
    770                 775                 780

Glu Glu Tyr Ile Ala Pro Glu Ile Ile Thr Gly Ala Gly His Thr Ser
785                 790                 795                 800

Ala Val Asp Trp Trp Ala Leu Gly Ile Leu Leu Tyr Glu Met Leu Tyr
            805                 810                 815
```

-continued

Gly Tyr Thr Pro Phe Arg Gly Lys Thr Arg Gln Arg Thr Phe Ala Asn
                820                 825                 830

Ile Leu His Lys Asp Ile Arg Phe Pro Ala Ser Ile Ser Val Ser Leu
            835                 840                 845

Pro Ala Arg Gln Leu Ile Tyr Arg Leu Leu His Arg Asp Pro Ser Asn
        850                 855                 860

Arg Leu Gly Ser Tyr Glu Gly Ser Asn Glu Ile Lys Glu His Pro Phe
865                 870                 875                 880

Phe Arg Gly Ile Asn Trp Ala Leu Val Arg Gly Thr Ala Pro Pro Lys
                885                 890                 895

Leu Asp Ala Pro Leu Phe Pro Asp Asp Thr Asp Lys Gly Met Gly Asp
            900                 905                 910

Ala Ala Ala Ala Asp Thr His Thr Asp Met Phe
        915                 920

<210> SEQ ID NO 2
<211> LENGTH: 3467
<212> TYPE: DNA
<213> ORGANISM: Avena sativa
<220> FEATURE:
<221> NAME/KEY: misc_feature
<222> LOCATION: 30, 3398
<223> OTHER INFORMATION: n = a, c, t or g

<400> SEQUENCE: 2

```
aggtcgacac tagtggatcc aaagaattcn ggcacgagcc ccccaattcc cttcgtccca      60
cggccatgcc gcgcggtctt ccgagcgggc atatacgtac cctagctacg cgcgcagcaa     120
gcatctactg tgcagatcgc ctctcgcttc acgcgcaccg gcgcaaaggc tagccaagtg     180
ctcgctgcct ctgccccgtc tcgacctctc ttcctagcta gctccctcgt agagtccact     240
gcgcactgct cgcgagcaga taaagaaata tagtgggatg agagctgagg gtgcgtgcgg     300
ttttaggttc ttggatcacg cgccagcgag cacgccaaga tagaaggagg aggaaggaag     360
agtcgctgct actggcctgc tatttagctg aagcttcaca tcaatggctt ccaaaggtgc     420
aggaggcggc ggcggcggcc atgaggagcc tcagcgccg aagcagcagc tgccgcgcga     480
ctcccgcggc tcgctcgagg tcttcaaccc ctcttcctcc tccgccgccg tcgagccccc     540
ctccgcgttc cgcccccgcc gcaggtccgc ctccccgttc atcgaggaag caacgggcgg     600
catcgaggat gtcggcaagg ccacgcagcg ggcggcggag tggggcctcg tgctccagac     660
caacgagcag acgggccggc cgcagggcgt gtccgcccga tcctccggag gcggcggctc     720
cgcccgcagc agctccgacg acaaggccgt cgccggcgcc atccccgggg tctcggagga     780
gctccgggcc gcgctctccg cgttccagca gaccttcgtc gtgtcggacg ccagccgacc     840
cggccacccca atcatgtacg ccagcgccgg cttcttcaac atgaccggct acacatccaa     900
ggaggtcgtc ggaaggaact gccgcttcct ccaaggctcc ggcaccgacc ggcggagat     960
tgccaagatc aggcaggctc tagcaaatgg atcaaactac tgcggccgtg tcctcaacta    1020
caagaaggac ggcaccgcat tctggaacct cttgaccatt gccccaatca aggatgaaga    1080
aggcagggtc ctcaagttca tagggatgca agtggaagta agtaaataca ctgaagggaa    1140
caaggatacg gttgttcgtc caaatggcct gccagagtca ctcatcaaat atgatgccag    1200
gcaaaaggat caggcccgta gctcagtgtc tgagcttctg ttggctatca gaatccacg     1260
atcattgtca gaatcaacta atagcacctt taaagaaaa tcacaggaat cagtaggtgc    1320
attgacgggt gatcgtcctg gcaagagaag ctcagaaagt ggatctcgac gtaactcaaa    1380
```

-continued

```
atctggagca agaacctcac tgcaaaagat cagcgaagta cctgaaagag gcagtaaaag    1440
tagaaaatct ggtctgtatt cacttatgag tttacttggt atgggccctg gaaatataga    1500
aaaggacatg ctgaaaccaa gagatgaaga cccgctactt gacagtgatg atgaaagacc    1560
tgagagtttt gatgatgagc taaggcggaa agaaatgaga aggggtatag acttggctac    1620
tacacttgaa cgtattgaga agaactttgt cattactgac ccaaggttgc cagataatcc    1680
cattatattc gcgtccgata gtttcttgca gttgacagaa tatagccgtg aagaaatttt    1740
gggaagaaac tgcaggtttc tacaaggtcc tgaaactgat cgcgcgacag tgagaaaaat    1800
tagagatgcc atagataacc aaacagaggt cactgttcag ctgattaatt atacaaagag    1860
tggtaaaaag ttctggaacc tctttcactt gcagcctatg cgagatcaga agggagatgt    1920
ccagtacttt attggggttc agttggatgg aactgagcat gtccgagatg ctgccgagag    1980
agagggagtc atgctgatta agaaaactgc agaaaatatt gatgaggcgg caaaagaact    2040
tccagatgct aatttgagac cagaggattt gtgggctaac cactcaaaag tagttttgcc    2100
aaagccacat atgaaggatt ctgcatcatg gagagccatc caaaaagttc ttgagggtgg    2160
agaaaacatt gatttgaagc atttcaggcc tgtaaagcct ttgggatctg gtgacactgg    2220
aagcgtgcac ttggtggagt tattaaacac aggtgaatac tttgccatga agctatgga    2280 taaaaacgtc atgcttaacc gcaataaggt tcatagagct aacgctgaac gagaaatcct    2340
tgatatgttg gatcacccat tccttccgac attatatgcg tcatttcaga caaagacaca    2400
tatatgtctc attacagact actaccctgg cggggagctc tttctgctcc tagatagaca    2460
acctctaaag gttctgcggg aagatgccgt caggttctat gctgctgaag ttgtcattgc    2520
acttgaatac ttgcattgcc aaggaataat ctaccgagac ttgaagccag agaatatctt    2580
acttcacagg gacgggcaca tctccttgac agactttgat ttgtcttgtc tgacatcttg    2640
cagaccgcag gtctttcttc cagaagaagc taataagaaa agtaggagga aaagcaggag    2700
ttcacccata ttttttgctg aacctatgcg agcatccaat tcatttgttg gtacagagga    2760
gtacattgca cctgagatca ttactggagc tggccataca agtgctgttg attggtgggc    2820
gctagggatc ctcctgtatg aaatgttgta tggttacaca cccttcagag gtaaaaccag    2880
gcagaggaca ttcgccaaca tcctacacaa ggacatcaga tttcccgcga gtatatcggt    2940
gagcctccca gcaaggcagc tgatatatag gctgctacac agggatcctt cgaataggct    3000
gggatcgtac gagggatcaa acgagataaa agaacaccct ttcttccgcg gcatcaactg    3060
ggctctcgtg cgtggcacgg ctcctccaaa gctggacgct ccactgttcc cggatgacac    3120
ggacaaggga atgggcgatg ctgctgctgc tgatactcac accgacatgt tctgaatgaa    3180
gaagctggct tggataaaaa cgcatctcga tcaagctcaa tcatgcatgc atgttttgt    3240 ttgttgttga tagctgctgt ttactactgc ctaggattgt aggaataatt aagctagcct    3300
gggatcgctg gatgtaatgt aatgtattgt actgcgtgta tttggatcgt gcttaaataa    3360
taatcaagtt cagccaaaaa aaaaaaaaaa aaaactcnga gagtacttct agagcggccg    3420
cgggcccatc gattttccac ccgggtgggt accagtaatt acccaat                  3467
```

<210> SEQ ID NO 3
<211> LENGTH: 109
<212> TYPE: PRT
<213> ORGANISM: Artificial Sequence
<220> FEATURE:
<223> OTHER INFORMATION: Avena sativa
<220> FEATURE:

<223> OTHER INFORMATION: NPH1-1 (AA 412-515) with N-terminal linker

<400> SEQUENCE: 3

Gly His Met Ala Ser Glu Lys Asn Phe Val Ile Cys Asp Pro Arg Leu
1               5                   10                  15

Pro Asp Asn Pro Ile Ile Phe Ala Ser Asp Ser Phe Leu Gln Leu Thr
            20                  25                  30

Glu Tyr Ser Arg Glu Glu Ile Leu Gly Arg Asn Ala Arg Phe Leu Gln
        35                  40                  45

Gly Pro Glu Thr Asp Arg Ala Thr Val Arg Lys Ile Arg Asp Ala Ile
    50                  55                  60

Asp Asn Gln Thr Glu Val Thr Val Gln Leu Ile Asn Tyr Thr Lys Ser
65                  70                  75                  80

Gly Lys Lys Phe Trp Asn Leu Phe His Leu Gln Pro Met Arg Asp Gln
                85                  90                  95

Lys Gly Asp Val Gln Tyr Phe Ile Gly Val Gln Leu Asp
            100                 105

<210> SEQ ID NO 4
<211> LENGTH: 107
<212> TYPE: PRT
<213> ORGANISM: Artificial Sequence
<220> FEATURE:
<223> OTHER INFORMATION: Avena sativa
<220> FEATURE:
<223> OTHER INFORMATION: NPH1-1 (AA 412-490) with N-terminal linker

<400> SEQUENCE: 4

Met Ala Ser Glu Lys Asn Phe Val Ile Cys Asp Pro Arg Leu Pro Asp
1               5                   10                  15

Asn Pro Ile Ile Phe Ala Ser Asp Ser Phe Leu Gln Leu Thr Glu Tyr
            20                  25                  30

Ser Arg Glu Glu Ile Leu Gly Arg Asn Ala Arg Phe Leu Gln Gly Pro
        35                  40                  45

Glu Thr Asp Arg Ala Thr Val Arg Lys Ile Arg Asp Ala Ile Asp Asn
    50                  55                  60

Gln Thr Glu Val Thr Val Gln Leu Ile Asn Tyr Thr Lys Ser Gly Lys
65                  70                  75                  80

Lys Phe Trp Asn Leu Phe His Leu Gln Pro Met Arg Asp Gln Lys Gly
                85                  90                  95

Asp Val Gln Tyr Phe Ile Gly Val Gln Leu Asp
            100                 105

<210> SEQ ID NO 5

<400> SEQUENCE: 5

000

<210> SEQ ID NO 6
<211> LENGTH: 186
<212> TYPE: PRT
<213> ORGANISM: Photobacterium leiognathi
<220> FEATURE:
<223> OTHER INFORMATION: Lumazine protein (LUMP), gene: lumP

<400> SEQUENCE: 6

Met Phe Arg Gly Ile Val Gln Gly Arg Gly Val Ile Arg Ser Ile Ser
1               5                   10                  15

Lys Ser Glu Asp Ser Gln Arg His Gly Ile Ala Phe Pro Glu Gly Met

|   |   | 20 |   |   | 25 |   |   | 30 |   |   |   |
|---|---|---|---|---|---|---|---|---|---|---|---|

Phe Gln Leu Val Asp Val Asp Thr Val Met Leu Val Asn Gly Cys Ser
      35                     40                   45

Leu Thr Val Val Arg Ile Leu Gly Asp Met Val Tyr Phe Asp Ile Asp
 50                      55                   60

Gln Ala Leu Gly Thr Thr Phe Asp Gly Leu Lys Glu Gly Asp Gln
65                   70                   75                 80

Val Asn Leu Glu Ile His Pro Lys Phe Gly Glu Val Val Gly Arg Gly
             85                     90                   95

Gly Leu Thr Gly Asn Ile Lys Gly Thr Ala Leu Val Ala Ala Ile Glu
            100                  105              110

Glu Asn Asp Ala Gly Phe Ser Val Leu Ile Asp Ile Pro Lys Gly Leu
            115                  120              125

Ala Glu Asn Leu Thr Val Lys Asp Asp Ile Gly Ile Asp Gly Ile Ser
          130                 135              140

Leu Pro Ile Thr Asp Met Ser Asp Ser Ile Ile Thr Leu Asn Tyr Ser
145               150                  155              160

Arg Asp Leu Leu Ala Ser Thr Asn Ile Ala Ser Leu Ala Lys Asp Val
            165                  170              175

Lys Val Asn Val Glu Ile Leu Asn Glu Trp
            180                  185

```
<210> SEQ ID NO 7
<211> LENGTH: 1929
<212> TYPE: DNA
<213> ORGANISM: Photobacterium leiognathi
<220> FEATURE:
<223> OTHER INFORMATION: Lumazine protein (LUMP), gene: lumP

<400> SEQUENCE: 7
```

| | | | | |
|---|---|---|---|---|
| ctgcagcagt | taatcactac | cattcattta | aaatttcaac | gttcactttc | acatcttttg | 60 |
| ctaacgatgc | aatgttagta | ctcgctaaca | atcacgcga | gtaattcaat | gtaataatgc | 120 |
| tgtctgacat | atcagtgata | ggcaaagaga | tcccatcaat | tccaatatca | tctttcactg | 180 |
| ttaagttttc | agctaaccct | ttagggatat | caatcagtac | agaaaaacct | gcgtcattct | 240 |
| cttctattgc | tgcgaccagc | gcagtgcctt | taatatttcc | tgttaatcca | ccacggcaaa | 300 |
| ccacttcacc | aaatttaggg | tggatctcta | ggtttacctg | atcgccttct | tttaatccat | 360 |
| caaatgttgt | cgtacccaat | gcttggtcga | tatcaaagta | caccatatcg | cctaaaatac | 420 |
| ggacaactgt | caatgaacaa | ccatttacta | acattacagt | atctacatca | acaagttgaa | 480 |
| acatacccctc | agggaatgca | atcccatgtc | gctgactatc | ttcactttt | gaaatggatc | 540 |
| gaataacacc | acgaccttga | caataccctc | taaacattac | tgtctccttt | tttagactct | 600 |
| atatgatatt | tcagtaaaaa | atacaactag | cacatttatg | agattctagt | aattgaagaa | 660 |
| agaaatacaa | aaagcggaca | cattttttct | attaccatca | caatttttt | aattaaacaa | 720 |
| tattaaaatc | aatcttgtat | taacaatgaa | atatcaataa | tattttaatg | ggcaattgaa | 780 |
| acattattca | ttttacattc | caattgaacg | ctatataaac | aattccagcc | aatacccatc | 840 |
| aaaaatcccc | ttaccccaat | aaaaaataaa | taaaacaaa | taaaaatcaa | caacttaaca | 900 |
| aacaaaacca | ccagcagata | cttgctaaaa | tccgtatata | aaaggttgag | taatatttac | 960 |
| ctaataaaaa | taaatctat | tattaaaact | taaaaaatac | aaaacaaat | actgtttaat | 1020 |
| taaataaaaa | acaccggagt | aaatataaaa | taaaaatata | aataaagtt | caaaatataa | 1080 |
| ccaaaaagct | taaatttaca | tttataaaaa | atcatagaaa | taataaacac | aataaattcc | 1140 |

-continued

```
gcactgcatt ctatattttt tagaacgatt tttaagcaca tataagtgta aaaaaaactg    1200
ggcagagtaa atataaaaac catgaattaa aaataatatt gtcaacaatg tgagccaaat    1260
ctcaaaacgt aacaaatgca aaacaattta cttacactaa aaaaaatatt ctcctagcct    1320
aatttcattc cctatgcagc atgcgactat gcaattaggg tatataaaac ttacaatatg    1380
ctaatggaga ttgcatgatt aaaaagatcc cactgattat tggaggcgaa gttcaagaca    1440
cgtcagaaca tgatgtccgt gaacttacgc ttaacaataa caccgtcaat gtacctatca    1500
ttacggacaa agatgctgaa tctatcacct cactaaaaat agaaataag ttaaatatca     1560 accagatagt taacttcttg tatactgtag ggcaaaaatg gaagagtgag aactacagcc    1620
gtcgcctcac ttatattcgt gatctagtaa aattcatggg ctactcccct gagatggcaa    1680
aactagaagc gaactggatt tcgatgattc tatgtagcaa aagtgcgcta tatgacattg    1740
ttgaaaatga tctcagctct cgtcatattg ttgatgaatg ctcccccaa ggtgattgct     1800 atgttaaagc gctaccaaaa ggtaaatcta tccatttatt agcgggtaac gttccgctat    1860
caggtgtgac atcgatcctg cgtgcaattt taactaaaaa tgaatgtatc attaaaacat    1920
catctgcag                                                            1929
```

<210> SEQ ID NO 8
<211> LENGTH: 104
<212> TYPE: PRT
<213> ORGANISM: Photobacterium leiognathi
<220> FEATURE:
<223> OTHER INFORMATION: Truncated Lumazine protein (LUMP, AA 1-102),
      gene: lumP

<400> SEQUENCE: 8

Gly His Met Phe Arg Gly Ile Val Gln Gly Arg Gly Val Ile Arg Ser
1               5                   10                  15

Ile Ser Lys Ser Glu Asp Ser Gln Arg His Gly Ile Ala Phe Pro Glu
            20                  25                  30

Gly Met Phe Gln Leu Val Asp Val Asp Thr Val Met Leu Val Asn Gly
        35                  40                  45

Cys Ser Leu Thr Val Val Arg Ile Leu Gly Asp Met Val Tyr Phe Asp
    50                  55                  60

Ile Asp Gln Ala Leu Gly Thr Thr Thr Phe Asp Gly Leu Lys Glu Gly
65                  70                  75                  80

Asp Gln Val Asn Leu Glu Ile His Pro Lys Phe Gly Glu Val Val Gly
                85                  90                  95

Arg Gly Gly Leu Thr Gly Asn Ile
            100

<210> SEQ ID NO 9
<211> LENGTH: 188
<212> TYPE: PRT
<213> ORGANISM: Photobacterium leiognathi
<220> FEATURE:
<223> OTHER INFORMATION: Lumazine protein (LUMP)

<400> SEQUENCE: 9

Gly His Met Phe Arg Gly Ile Val Gln Gly Arg Gly Val Ile Arg Ser
1               5                   10                  15

Ile Ser Lys Ser Glu Asp Ser Gln Arg His Gly Ile Ala Phe Pro Glu
            20                  25                  30

Gly Met Phe Gln Leu Val Asp Val Asp Thr Val Met Leu Val Asn Gly
        35                  40                  45

```
Cys Ser Leu Thr Val Val Arg Ile Leu Gly Asp Met Val Tyr Phe Asp
     50                  55                  60

Ile Asp Gln Ala Leu Gly Thr Thr Phe Asp Gly Leu Lys Glu Gly
 65                 70                  75                  80

Asp Gln Val Asn Leu Glu Ile His Pro Lys Phe Gly Glu Val Val Gly
                 85                  90                  95

Arg Gly Gly Leu Thr Gly Asn Ile Lys Gly Thr Ala Leu Val Ala Ala
                100                 105                 110

Ile Glu Glu Asn Asp Ala Gly Phe Ser Val Leu Ile Asp Ile Pro Lys
            115                 120                 125

Gly Leu Ala Glu Asn Leu Thr Val Lys Asp Asp Ile Gly Ile Asp Gly
        130                 135                 140

Ile Ser Leu Pro Ile Thr Asp Met Ser Asp Ser Ile Ile Thr Leu Asn
145                 150                 155                 160

Tyr Ser Arg Asp Leu Leu Ala Ser Thr Asn Ile Ala Ser Leu Ala Lys
                165                 170                 175

Asp Val Lys Val Asn Val Glu Ile Leu Asn Glu Trp
            180                 185
```

<210> SEQ ID NO 10
<211> LENGTH: 97
<212> TYPE: PRT
<213> ORGANISM: Artificial Sequence
<220> FEATURE:
<223> OTHER INFORMATION: Aliivibrio fischeri (Vibrio fischeri)
<220> FEATURE:
<223> OTHER INFORMATION: Truncated N-terminal domain of RS

<400> SEQUENCE: 10

```
Met Phe Thr Gly Ile Val Gln Gly Thr Ala Lys Leu Val Ser Ile Asp
 1               5                  10                  15

Glu Lys Pro Asn Phe Arg Thr His Val Val Glu Leu Pro Asp His Met
                 20                  25                  30

Leu Asp Gly Leu Glu Thr Gly Ala Ser Val Ala His Asn Gly Cys Cys
             35                  40                  45

Leu Thr Val Thr Glu Ile Asn Gly Asn His Val Ser Phe Asp Leu Met
 50                  55                  60

Lys Glu Thr Leu Arg Ile Thr Asn Leu Gly Asp Leu Lys Val Gly Asp
65                  70                  75                  80

Trp Val Asn Val Glu Arg Ala Ala Lys Phe Ser Asp Glu Ile Gly Gly
                 85                  90                  95

His
```

<210> SEQ ID NO 11
<211> LENGTH: 122
<212> TYPE: PRT
<213> ORGANISM: Artificial Sequence
<220> FEATURE:
<223> OTHER INFORMATION: Aliivibrio fischeri (Vibrio fischeri)
<220> FEATURE:
<223> OTHER INFORMATION: Truncated N-terminal domain of RS with His-tag
    and TEV protease site at N-terminus

<400> SEQUENCE: 11

```
Met Gly Ser Ser His His His His His His Asp Tyr Asp Ile Pro Thr
 1               5                  10                  15

Thr Glu Asn Leu Tyr Phe Gln Gly His Met Phe Thr Gly Ile Val Gln
                 20                  25                  30
```

Gly Thr Ala Lys Leu Val Ser Ile Asp Glu Lys Pro Asn Phe Arg Thr
            35                  40                  45

His Val Glu Leu Pro Asp His Met Leu Asp Gly Leu Glu Thr Gly
 50                  55                  60

Ala Ser Val Ala His Asn Gly Cys Cys Leu Thr Val Thr Glu Ile Asn
 65                  70                  75                  80

Gly Asn His Val Ser Phe Asp Leu Met Lys Glu Thr Leu Arg Ile Thr
                    85                  90                  95

Asp Leu Gly Asp Leu Lys Val Gly Asp Trp Val Ala Val Glu Arg Ala
                100                 105                 110

Ala Lys Phe Ser Asp Glu Ile Gly Gly His
            115                 120

<210> SEQ ID NO 12
<211> LENGTH: 194
<212> TYPE: PRT
<213> ORGANISM: Vibrio fisherei
<220> FEATURE:
<223> OTHER INFORMATION: Y1

<400> SEQUENCE: 12

Met Phe Lys Gly Ile Val Glu Gly Ile Gly Ile Glu Lys Ile Asp
 1               5                  10                  15

Ile Tyr Thr Asp Leu Asp Lys Tyr Ala Ile Arg Phe Pro Glu Asn Met
            20                  25                  30

Leu Asn Gly Ile Lys Lys Glu Ser Ser Ile Met Phe Asn Gly Cys Phe
        35                  40                  45

Leu Thr Val Thr Ser Val Asn Ser Asn Ile Val Trp Phe Asp Ile Phe
 50                  55                  60

Glu Lys Glu Ala Arg Lys Leu Asp Thr Phe Arg Glu Tyr Lys Val Gly
 65                  70                  75                  80

Asp Arg Val Asn Leu Gly Thr Phe Pro Lys Phe Gly Ala Ala Ser Gly
                85                  90                  95

Gly His Ile Leu Ser Ala Arg Ile Ser Cys Val Ala Ser Ile Ile Glu
            100                 105                 110

Ile Ile Glu Asn Glu Asp Tyr Gln Gln Met Trp Ile Gln Ile Pro Glu
        115                 120                 125

Asn Phe Thr Glu Phe Leu Leu Asp Lys Asp Tyr Ile Ala Val Asp Gly
130                 135                 140

Ile Ser Leu Thr Ile Thr Ile Lys Asn Asn Gln Phe Phe Ile Ser
145                 150                 155                 160

Leu Pro Leu Lys Ile Ala Gln Asn Thr Asn Met Lys Trp Arg Lys Lys
                165                 170                 175

Gly Asp Lys Val Asn Val Glu Leu Ser Asn Lys Ile Asn Ala Asn Gln
            180                 185                 190

Cys Trp

<210> SEQ ID NO 13
<211> LENGTH: 771
<212> TYPE: DNA
<213> ORGANISM: Vibrio fisherei
<220> FEATURE:
<223> OTHER INFORMATION: Y1

<400> SEQUENCE: 13
aatattttta ttaattcatt agaaaaatga gaggaaggat tattatgttt aaaggtatag    60
tagaaggtat aggaatcatt gaaaaaattg atatatatac tgacctagat aagtatgcaa   120

```
ttcgatttcc tgaaaatatg ttgaatggaa ttaaaaagga gtcgtcaata atgtttaacg    180
gatgcttctt aacggtaact agcgtgaatt caaacattgt ctggtttgat atatttgaaa    240
aagaagcacg taagcttgat acttttcggg aatataaggt aggtgaccga gtaaatttag    300
gaacattccc aaaatttggc gctgcatctg gtgggcatat attatcagca aggatttcat    360
gtgtagcaag tattattgaa ataatagaaa atgaggatta tcaacaaatg tggattcaaa    420
ttcctgaaaa ttttacagag tttcttattg ataaagacta tattgctgtg gatggtatta    480
gcttaactat tgacactata aaaaacaacc aatttttcat tagtttaccc ttaaaaatag    540
cacaaaatac aaatatgaaa tggcgaaaaa aaggtgataa ggtaaatgtt gagttatcaa    600
acaaaattaa tgctaaccag tgttggtaat ttactgagga tagtaaaaat gaactgttta    660
aaataatatt taattttta tttataatac agagtcagtt gttgtaaata gtctgagtgg    720
taaataagtt ctaccattaa ttaaatatta tccatattaa ataaggatc t               771
```

<210> SEQ ID NO 14
<211> LENGTH: 211
<212> TYPE: PRT
<213> ORGANISM: Artificial Sequence
<220> FEATURE:
<223> OTHER INFORMATION: Synthetic

<400> SEQUENCE: 14

```
Met Gly Ser Ser His His His His His His Asp Tyr Asp Ile Pro Thr
1               5                   10                  15

Thr Glu Asn Leu Tyr Phe Gln Gly His Met Phe Arg Gly Ile Val Gln
            20                  25                  30

Gly Arg Gly Val Ile Arg Ser Ile Ser Lys Ser Glu Asp Ser Gln Arg
        35                  40                  45

His Gly Ile Ala Phe Pro Glu Gly Met Phe Gln Leu Val Asp Val Asp
    50                  55                  60

Thr Val Met Leu Val Asn Gly Cys Ser Leu Thr Val Val Arg Ile Leu
65                  70                  75                  80

Gly Asp Met Val Tyr Phe Asp Ile Asp Gln Ala Leu Gly Thr Thr Thr
                85                  90                  95

Phe Asp Gly Leu Lys Glu Gly Asp Gln Val Asn Leu Glu Ile His Pro
            100                 105                 110

Lys Phe Gly Glu Val Val Gly Arg Gly Gly Leu Thr Gly Asn Ile Lys
        115                 120                 125

Gly Thr Ala Leu Val Ala Ala Ile Glu Glu Asn Asp Ala Gly Phe Ser
    130                 135                 140

Val Leu Ile Asp Ile Pro Lys Gly Leu Ala Glu Asn Leu Thr Val Lys
145                 150                 155                 160

Asp Asp Ile Gly Ile Asp Gly Ile Ser Leu Pro Ile Thr Asp Met Ser
                165                 170                 175

Asp Ser Ile Ile Thr Leu Asn Tyr Ser Arg Asp Leu Leu Ala Ser Thr
            180                 185                 190

Asn Ile Ala Ser Leu Ala Lys Asp Val Lys Val Asn Val Glu Ile Leu
        195                 200                 205

Asn Glu Trp
    210
```

<210> SEQ ID NO 15
<211> LENGTH: 259
<212> TYPE: PRT

<213> ORGANISM: Artificial Sequence
<220> FEATURE:
<223> OTHER INFORMATION: Synthetic

<400> SEQUENCE: 15

Met Gly Ser Ser His His His His His His Asp Tyr Asp Ile Pro Thr
1               5                   10                  15

Thr Glu Asn Leu Tyr Phe Gln Gly His Met Gly Leu Ser Ala Gln Asp
            20                  25                  30

Ile Ser Gln Pro Leu Gln Asn Ser Phe Ile His Thr Gly His Gly Asp
        35                  40                  45

Ser Asp Pro Arg His Cys Trp Gly Phe Pro Arg Ile Asp Glu Leu
    50                  55                  60

Tyr Leu Gly Asn Gly Ser Gly Ser Ala Ser Phe Arg Gly Ile Val Gln
65              70                  75                  80

Gly Arg Gly Val Ile Arg Ser Ile Ser Lys Ser Glu Asp Ser Gln Arg
                85                  90                  95

His Gly Ile Ala Phe Pro Glu Gly Met Phe Gln Leu Val Asp Val Asp
            100                 105                 110

Thr Val Met Leu Val Asn Gly Cys Ser Leu Thr Val Val Arg Ile Leu
        115                 120                 125

Gly Asp Met Val Tyr Phe Asp Ile Asp Gln Ala Leu Gly Thr Thr Thr
    130                 135                 140

Phe Asp Gly Leu Lys Glu Gly Asp Gln Val Asn Leu Glu Ile His Pro
145                 150                 155                 160

Lys Phe Gly Glu Val Val Gly Arg Gly Gly Leu Thr Gly Asn Ile Lys
                165                 170                 175

Gly Thr Ala Leu Val Ala Ala Ile Glu Glu Asn Asp Ala Gly Phe Ser
            180                 185                 190

Val Leu Ile Asp Ile Pro Lys Gly Leu Ala Glu Asn Leu Thr Val Lys
        195                 200                 205

Asp Asp Ile Gly Ile Asp Gly Ile Ser Leu Pro Ile Thr Asp Met Ser
    210                 215                 220

Asp Ser Ile Ile Thr Leu Asn Tyr Ser Arg Asp Leu Leu Ala Ser Thr
225                 230                 235                 240

Asn Ile Ala Ser Leu Ala Lys Asp Val Lys Val Asn Val Glu Ile Leu
                245                 250                 255

Asn Glu Trp

<210> SEQ ID NO 16
<211> LENGTH: 451
<212> TYPE: PRT
<213> ORGANISM: Artificial Sequence
<220> FEATURE:
<223> OTHER INFORMATION: Synthetic

<400> SEQUENCE: 16

Met Gly Ser Ser His His His His His His Asp Tyr Asp Ile Pro Thr
1               5                   10                  15

Thr Glu Asn Leu Tyr Phe Gln Gly His Met Val Ser Lys Gly Glu Glu
            20                  25                  30

Leu Phe Thr Gly Val Val Pro Ile Leu Val Glu Leu Asp Gly Asp Val
        35                  40                  45

Asn Gly His Lys Phe Ser Val Ser Gly Glu Gly Glu Gly Asp Ala Thr
    50                  55                  60

Tyr Gly Lys Leu Thr Leu Lys Phe Ile Cys Thr Thr Gly Lys Leu Pro

```
            65                  70                  75                  80
        Val Pro Trp Pro Thr Leu Val Thr Thr Phe Gly Tyr Gly Leu Met Cys
                            85                  90                  95

Phe Ala Arg Tyr Pro Asp His Met Lys Gln His Asp Phe Phe Lys Ser
                        100                 105                 110

Ala Met Pro Glu Gly Tyr Val Gln Glu Arg Thr Ile Phe Phe Lys Asp
                    115                 120                 125

Asp Gly Asn Tyr Lys Thr Arg Ala Glu Val Lys Phe Glu Gly Asp Thr
                130                 135                 140

Leu Val Asn Arg Ile Glu Leu Lys Gly Ile Asp Phe Lys Glu Asp Gly
        145                 150                 155                 160

Asn Ile Leu Gly His Lys Leu Glu Tyr Asn Tyr Asn Ser His Asn Val
                        165                 170                 175

Tyr Ile Met Ala Asp Lys Gln Lys Asn Gly Ile Lys Val Asn Phe Lys
                    180                 185                 190

Ile Arg His Asn Ile Glu Asp Gly Ser Val Gln Leu Ala Asp His Tyr
                195                 200                 205

Gln Gln Asn Thr Pro Ile Gly Asp Gly Pro Val Leu Leu Pro Asp Asn
            210                 215                 220

His Tyr Leu Ser Tyr Gln Ser Ala Leu Ser Lys Asp Pro Asn Glu Lys
        225                 230                 235                 240

Arg Asp His Met Val Leu Leu Glu Phe Val Thr Ala Ala Gly Ile Thr
                        245                 250                 255

Leu Gly Met Asp Glu Leu Tyr Lys Ala Ser Phe Arg Gly Ile Val Gln
                    260                 265                 270

Gly Arg Gly Val Ile Arg Ser Ile Ser Lys Ser Glu Asp Ser Gln Arg
                275                 280                 285

His Gly Ile Ala Phe Pro Glu Gly Met Phe Gln Leu Val Asp Val Asp
            290                 295                 300

Thr Val Met Leu Val Asn Gly Cys Ser Leu Thr Val Val Arg Ile Leu
        305                 310                 315                 320

Gly Asp Met Val Tyr Phe Asp Ile Asp Gln Ala Leu Gly Thr Thr Thr
                        325                 330                 335

Phe Asp Gly Leu Lys Glu Gly Asp Gln Val Asn Leu Glu Ile His Pro
                    340                 345                 350

Lys Phe Gly Glu Val Val Gly Arg Gly Gly Leu Thr Gly Asn Ile Lys
                355                 360                 365

Gly Thr Ala Leu Val Ala Ala Ile Glu Glu Asn Asp Ala Gly Phe Ser
            370                 375                 380

Val Leu Ile Asp Ile Pro Lys Gly Leu Ala Glu Asn Leu Thr Val Lys
        385                 390                 395                 400

Asp Asp Ile Gly Ile Asp Gly Ile Ser Leu Pro Ile Thr Asp Met Ser
                        405                 410                 415

Asp Ser Ile Ile Thr Leu Asn Tyr Ser Arg Asp Leu Leu Ala Ser Thr
                    420                 425                 430

Asn Ile Ala Ser Leu Ala Lys Asp Val Lys Val Asn Val Glu Ile Leu
                435                 440                 445

Asn Glu Trp
            450

<210> SEQ ID NO 17
<211> LENGTH: 460
<212> TYPE: PRT
<213> ORGANISM: Artificial Sequence
```

<220> FEATURE:
<223> OTHER INFORMATION: Synthetic

<400> SEQUENCE: 17

```
Met Gly Ser Ser His His His His His Asp Tyr Asp Ile Pro Thr
1               5                   10                  15

Thr Glu Asn Leu Tyr Phe Gln Gly His Met Val Ser Lys Gly Glu Glu
            20                  25                  30

Leu Phe Thr Gly Val Val Pro Ile Leu Val Glu Leu Asp Gly Asp Val
        35                  40                  45

Asn Gly His Lys Phe Ser Val Ser Gly Glu Gly Glu Gly Asp Ala Thr
50                  55                  60

Tyr Gly Lys Leu Thr Leu Lys Phe Ile Cys Thr Thr Gly Lys Leu Pro
65                  70                  75                  80

Val Pro Trp Pro Thr Leu Val Thr Thr Phe Gly Tyr Gly Leu Met Cys
                85                  90                  95

Phe Ala Arg Tyr Pro Asp His Met Lys Gln His Asp Phe Phe Lys Ser
            100                 105                 110

Ala Met Pro Glu Gly Tyr Val Gln Glu Arg Thr Ile Phe Phe Lys Asp
        115                 120                 125

Asp Gly Asn Tyr Lys Thr Arg Ala Glu Val Lys Phe Glu Gly Asp Thr
130                 135                 140

Leu Val Asn Arg Ile Glu Leu Lys Gly Ile Asp Phe Lys Glu Asp Gly
145                 150                 155                 160

Asn Ile Leu Gly His Lys Leu Glu Tyr Asn Tyr Asn Ser His Asn Val
                165                 170                 175

Tyr Ile Met Ala Asp Lys Gln Lys Asn Gly Ile Lys Val Asn Phe Lys
            180                 185                 190

Ile Arg His Asn Ile Glu Asp Gly Ser Val Gln Leu Ala Asp His Tyr
        195                 200                 205

Gln Gln Asn Thr Pro Ile Gly Asp Gly Pro Val Leu Leu Pro Asp Asn
210                 215                 220

His Tyr Leu Ser Tyr Gln Ser Ala Leu Ser Lys Asp Pro Asn Glu Lys
225                 230                 235                 240

Arg Asp His Met Val Leu Leu Glu Phe Val Thr Ala Ala Gly Ile Thr
                245                 250                 255

Leu Gly Met Asp Glu Leu Tyr Lys Ala Ser Leu Val Pro Arg Gly Ser
            260                 265                 270

Arg Gly Ser Phe Arg Gly Ile Val Gln Gly Arg Gly Val Ile Arg Ser
        275                 280                 285

Ile Ser Lys Ser Glu Asp Ser Gln Arg His Gly Ile Ala Phe Pro Glu
290                 295                 300

Gly Met Phe Gln Leu Asp Val Asp Thr Val Met Leu Val Asn Gly
305                 310                 315                 320

Cys Ser Leu Thr Val Val Arg Ile Leu Gly Asp Met Val Tyr Phe Asp
                325                 330                 335

Ile Asp Gln Ala Leu Gly Thr Thr Thr Phe Asp Gly Leu Lys Glu Gly
            340                 345                 350

Asp Gln Val Asn Leu Glu Ile His Pro Lys Phe Gly Glu Val Val Gly
        355                 360                 365

Arg Gly Gly Leu Thr Gly Asn Ile Lys Gly Thr Ala Leu Val Ala Ala
370                 375                 380

Ile Glu Glu Asn Asp Ala Gly Phe Ser Val Leu Ile Asp Ile Pro Lys
385                 390                 395                 400
```

```
Gly Leu Ala Glu Asn Leu Thr Val Lys Asp Asp Ile Gly Ile Asp Gly
            405                 410                 415

Ile Ser Leu Pro Ile Thr Asp Met Ser Asp Ser Ile Ile Thr Leu Asn
        420                 425                 430

Tyr Ser Arg Asp Leu Leu Ala Ser Thr Asn Ile Ala Ser Leu Ala Lys
    435                 440                 445

Asp Val Lys Val Asn Val Glu Ile Leu Asn Glu Trp
    450                 455                 460

<210> SEQ ID NO 18
<211> LENGTH: 33
<212> TYPE: DNA
<213> ORGANISM: Artificial Sequence
<220> FEATURE:
<223> OTHER INFORMATION: Synthetic

<400> SEQUENCE: 18
agcgcagcta gctttagagg tattgttcaa ggt                              33

<210> SEQ ID NO 19
<211> LENGTH: 27
<212> TYPE: DNA
<213> ORGANISM: Artificial Sequence
<220> FEATURE:
<223> OTHER INFORMATION: Synthetic

<400> SEQUENCE: 19
gagtgcggcc gcctaccatt catttaa                                    27

<210> SEQ ID NO 20
<211> LENGTH: 29
<212> TYPE: DNA
<213> ORGANISM: Artificial Sequence
<220> FEATURE:
<223> OTHER INFORMATION: Synthetic

<400> SEQUENCE: 20
atatatccat gggcctgagc gcacaggac                                  29

<210> SEQ ID NO 21
<211> LENGTH: 33
<212> TYPE: DNA
<213> ORGANISM: Artificial Sequence
<220> FEATURE:
<223> OTHER INFORMATION: Synthetic

<400> SEQUENCE: 21
tattataagc ttgagtgcgg ccgcctacca ttc                             33

<210> SEQ ID NO 22
<211> LENGTH: 36
<212> TYPE: DNA
<213> ORGANISM: Artificial Sequence
<220> FEATURE:
<223> OTHER INFORMATION: Synthetic

<400> SEQUENCE: 22
gcgcatatgc agacaattaa gtgtgttgtt gtgggc                          36

<210> SEQ ID NO 23
<211> LENGTH: 30
<212> TYPE: DNA
<213> ORGANISM: Artificial Sequence
<220> FEATURE:
```

```
<223> OTHER INFORMATION: Synthetic

<400> SEQUENCE: 23
tattatctcg agtcatagca gcacacacct                                           30

<210> SEQ ID NO 24
<211> LENGTH: 42
<212> TYPE: DNA
<213> ORGANISM: Artificial Sequence
<220> FEATURE:
<223> OTHER INFORMATION: Synthetic

<400> SEQUENCE: 24 gacttttttgg tactgcaggg ctagaggatt atgatagatt ac                            42

<210> SEQ ID NO 25
<211> LENGTH: 42
<212> TYPE: DNA
<213> ORGANISM: Artificial Sequence
<220> FEATURE:
<223> OTHER INFORMATION: Synthetic

<400> SEQUENCE: 25
gtaatctatc ataatcctct agccctgcag taccaaaaag tc                             42

<210> SEQ ID NO 26
<211> LENGTH: 382
<212> TYPE: PRT
<213> ORGANISM: Artificial Sequence
<220> FEATURE:
<223> OTHER INFORMATION: Synthetic

<400> SEQUENCE: 26
```

His His His His His His Gly Met Ala Ser Met Thr Gly Gly Gln Gln
1               5                   10                  15

Met Gly Arg Asp Leu Tyr Glu Asn Leu Tyr Phe Gln Gly Ser Ser Met
            20                  25                  30

Val Ser Lys Gly Glu Glu Leu Ile Lys Glu Asn Met Arg Met Lys Val
        35                  40                  45

Val Met Glu Gly Ser Val Asn Gly His Gln Phe Lys Cys Thr Gly Glu
    50                  55                  60

Gly Glu Gly Asn Pro Tyr Met Gly Thr Gln Thr Met Arg Ile Lys Val
65                  70                  75                  80

Ile Glu Gly Gly Pro Leu Pro Phe Ala Phe Asp Ile Leu Ala Thr Ser
                85                  90                  95

Phe Met Tyr Gly Ser Arg Thr Phe Ile Lys Tyr Pro Lys Gly Ile Pro
            100                 105                 110

Asp Phe Phe Lys Gln Ser Phe Pro Glu Gly Phe Thr Trp Glu Arg Val
        115                 120                 125

Thr Arg Tyr Glu Asp Gly Gly Val Val Thr Val Met Gln Asp Thr Ser
    130                 135                 140

Leu Glu Asp Gly Cys Leu Val Tyr His Val Gln Val Arg Gly Val Asn
145                 150                 155                 160

Phe Pro Ser Asn Gly Pro Val Met Gln Lys Lys Thr Lys Gly Trp Glu
                165                 170                 175

Pro Asn Thr Glu Met Met Tyr Pro Ala Asp Gly Gly Leu Arg Gly Tyr
            180                 185                 190

Thr His Met Ala Leu Lys Val Asp Gly Gly Gly His Leu Ser Cys Ser
        195                 200                 205

```
Phe Val Thr Thr Tyr Arg Ser Lys Lys Thr Val Gly Asn Ile Lys Met
    210                 215                 220

Pro Gly Ile His Ala Val Asp His Arg Leu Glu Arg Leu Glu Glu Ser
225                 230                 235                 240

Asp Asn Glu Met Phe Val Gln Arg Glu His Ala Val Ala Lys Phe
                245                 250                 255

Ala Gly Leu Gly Gly Met Asp Glu Leu Tyr Lys Gly Ser Leu Val
            260                 265                 270

Pro Arg Gly Ser Ala Ser Glu Lys Asn Phe Val Ile Cys Asp Pro Arg
                275                 280                 285

Leu Pro Asp Asn Pro Ile Ile Phe Ala Ser Asp Ser Phe Leu Gln Leu
    290                 295                 300

Thr Glu Tyr Ser Arg Glu Glu Ile Leu Gly Arg Asn Ala Arg Phe Leu
305                 310                 315                 320

Gln Gly Pro Glu Thr Asp Arg Ala Thr Val Arg Lys Ile Arg Asp Ala
                325                 330                 335

Ile Asp Asn Gln Thr Glu Val Thr Val Gln Leu Ile Asn Tyr Thr Lys
                340                 345                 350

Ser Gly Lys Lys Phe Trp Asn Leu Phe His Leu Gln Pro Met Arg Asp
            355                 360                 365

Gln Lys Gly Asp Val Gln Tyr Phe Ile Gly Val Gln Leu Asp
370                 375                 380

<210> SEQ ID NO 27
<211> LENGTH: 274
<212> TYPE: PRT
<213> ORGANISM: Artificial Sequence
<220> FEATURE:
<223> OTHER INFORMATION: Synthetic

<400> SEQUENCE: 27

His His His His His His Gly Met Ala Ser Met Thr Gly Gly Gln Gln
1               5                   10                  15

Met Gly Arg Asp Leu Tyr Glu Asn Leu Tyr Phe Gln Gly Ser Ser Met
            20                  25                  30

Val Ser Lys Gly Glu Glu Leu Ile Lys Glu Asn Met Arg Met Lys Val
        35                  40                  45

Val Met Glu Gly Ser Val Asn Gly His Gln Phe Lys Cys Thr Gly Glu
    50                  55                  60

Gly Glu Gly Asn Pro Tyr Met Gly Thr Gln Thr Met Arg Ile Lys Val
65                  70                  75                  80

Ile Glu Gly Gly Pro Leu Pro Phe Ala Phe Asp Ile Leu Ala Thr Ser
                85                  90                  95

Phe Met Tyr Gly Ser Arg Thr Phe Ile Lys Tyr Pro Lys Gly Ile Pro
            100                 105                 110

Asp Phe Phe Lys Gln Ser Phe Pro Glu Gly Phe Thr Trp Glu Arg Val
        115                 120                 125

Thr Arg Tyr Glu Asp Gly Gly Val Val Thr Val Met Gln Asp Thr Ser
    130                 135                 140

Leu Glu Asp Gly Cys Leu Val Tyr His Val Gln Val Arg Gly Val Asn
145                 150                 155                 160

Phe Pro Ser Asn Gly Pro Val Met Gln Lys Lys Thr Lys Gly Trp Glu
                165                 170                 175

Pro Asn Thr Glu Met Met Tyr Pro Ala Asp Gly Gly Leu Arg Gly Tyr
            180                 185                 190
```

```
Thr His Met Ala Leu Lys Val Asp Gly Gly His Leu Ser Cys Ser
            195                 200                 205

Phe Val Thr Thr Tyr Arg Ser Lys Lys Thr Val Gly Asn Ile Lys Met
        210                 215                 220

Pro Gly Ile His Ala Val Asp His Arg Leu Glu Arg Leu Glu Glu Ser
225                 230                 235                 240

Asp Asn Glu Met Phe Val Val Gln Arg Glu His Ala Val Ala Lys Phe
                245                 250                 255

Ala Gly Leu Gly Gly Gly Met Asp Glu Leu Tyr Lys Gly Ser Leu Val
            260                 265                 270

Pro Arg

<210> SEQ ID NO 28
<211> LENGTH: 108
<212> TYPE: PRT
<213> ORGANISM: Artificial Sequence
<220> FEATURE:
<223> OTHER INFORMATION: Synthetic

<400> SEQUENCE: 28

Gly Ser Ala Ser Glu Lys Asn Phe Val Ile Cys Asp Pro Arg Leu Pro
1               5                   10                  15

Asp Asn Pro Ile Ile Phe Ala Ser Asp Ser Phe Leu Gln Leu Thr Glu
            20                  25                  30

Tyr Ser Arg Glu Glu Ile Leu Gly Arg Asn Ala Arg Phe Leu Gln Gly
        35                  40                  45

Pro Glu Thr Asp Arg Ala Thr Val Arg Lys Ile Arg Asp Ala Ile Asp
50                  55                  60

Asn Gln Thr Glu Val Thr Val Gln Leu Ile Asn Tyr Thr Lys Ser Gly
65                  70                  75                  80

Lys Lys Phe Trp Asn Leu Phe His Leu Gln Pro Met Arg Asp Gln Lys
                85                  90                  95

Gly Asp Val Gln Tyr Phe Ile Gly Val Gln Leu Asp
            100                 105

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Gly Ser Gly Ser Ala Ser
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic

<400> SEQUENCE: 30

Ser Gly Ser Ala Ser
1               5

<210> SEQ ID NO 31
<211> LENGTH: 10
<212> TYPE: PRT
<213> ORGANISM: Artificial Sequence
```

```
<220> FEATURE:
<223> OTHER INFORMATION: Synthetic

<400> SEQUENCE: 31

Gly Ser Gly Lys Ile Ile Ser Ala Gly Ser
1               5                   10
```

GENETICALLY ENCODED SENSORS FOR IMAGING PROTEINS AND THEIR COMPLEXES

CLAIM FOR PRIORITY

This application is a continuation in part of PCT App. No. PCT/US2014/038644, filed May 19, 2014, which claims priority to 61/825,434, filed May 20, 2013, the entire disclosures of which are hereby incorporated by reference.

STATEMENT OF GOVERNMENTAL SUPPORT

The present invention was supported by the Laboratory Directed Research and Development program under Contract No. DE-AC02-05CH11231 awarded by the U.S. Department of Energy. The present invention was supported under RO1 GM086233-02 awarded by the NIH. The government has certain rights to the invention.

REFERENCE TO SEQUENCE LISTING APPENDIX

The present application is being filed along with a Sequence Listing in electronic format. The Sequence Listing is provided as a file entitled SeqList_LBNL058P1.TXT, created on Nov. 18, 2015, last modified on Nov. 19, 2015, which is 48,110 bytes in size and updated by a file entitled LBNL058P1SEQLISTREPLACEMENT.txt, which is 48,269 bytes in size, created and modified on May 14, 2018, and updated by a file entitled LBNL058P1SEQLISTREPLACEMENT2.txt, which is 48,619 bytes in size, created and modified on Oct. 17, 2018. The information in the electronic format of the Sequence Listing is incorporated herein by reference in its entirety.

FIELD

The present invention relates to constructs, systems, and methods regarding genetically encoded proteins for imaging and detection of target molecules.

BACKGROUND

Genetically encoded proteins such as the green fluorescent protein (GFP) have revolutionized the fields of biology and biotechnology, spawning an industry based on their genes, fusion proteins, diagnostic kits and related biologics that is estimated to generate at $3 billion dollars in sales per year. These fluorescent proteins are widely used as sensors to detect and image proteins and their complexes in living cells and in vitro. The potential to improve upon existing fluorescent proteins, and to advance the aforementioned fields of application through new and improved types of genetically encoded fluorescent protein is very high.

SUMMARY

Embodiments provided herein provide for a new class of genetically encoded proteins whose optimized photophysical properties and small size are being exploited for: (A) fluorescence intensity imaging of fusion proteins, (B), fluorescence anisotropy (FA) based imaging and detection of target protein and their complexes and (C), Foerster resonance energy transfer (FRET) based imaging of target proteins and their complexes in vitro and in living cells, (D), Fluorescence lifetime based imaging (FLIM) and detection of target proteins and their complexes in vitro and in vivo.

In some embodiments, an isolated truncated and mutated sensor protein derived from LUMP that is 12 KDa or less is provided. It can be a genetically encoded for detection and imaging of protein complexes, wherein the sensor protein has a sequence comprising SEQ ID NO:8 or 9.

In some embodiments, a sensor protein having at least 80 percent (%) homology to SEQ ID NOS: 8 or 9 is provided.

In some embodiments, a genetically encoded fluorescence protein having a small mass that is about 20 kD or less, having a sequence that is at least 75% homologous to SEQ ID NOS:8 or 9, and having a fluorescent anisotropic lifetime that is >4.0 ns is provided.

In some embodiments, an isolated polynucleotide that when translated, provides for a protein having a sequence comprising SEQ ID NOS: 8 or 9 is provided.

In some embodiments, an isolated fluorescent variant of LUMP is provided. The variant is truncated such that it is 20 KDa or less in size, wherein the variant has a sequence that is at least 90% identical to SEQ ID NO: 8 or 9 and wherein the variant has a fluorescent anisotropic lifetime that is greater than 4.0 ns.

In some embodiments, a fluorescent anisotropy based sensor is provided. The sensor comprises a targeting protein; and a fluorescent molecule that is covalently linked to the targeting (protein). The fluorescent molecule is a truncated variant of a protein having the sequence of SEQ ID NO: 4, 8, 9, or 11 wherein the truncated variant is no greater in size than about 10 KDa, wherein the truncated variant comprises an amino acid sequence that is at least 90% identical to SEQ ID NO: 4, 8, 9, OR 11 for a section of the sequence that is present in the truncated variant, and wherein the truncated variant has an anisotropic lifetime of greater than 4 ns.

In some embodiments, a method of detecting a target molecule is provided. The method comprises providing an amino acid based fluorescent molecule. The fluorescent molecule is covalently linked to a targeting molecule that binds to the target molecule, and the fluorescent molecule has a fluorescent anisotropic lifetime that is greater than 4.0 ns. The method comprises adding the fluorescent molecule to a sample, and detecting if there is a change in fluorescent anisotropy of the fluorescent molecule.

In some embodiments, an isolated fluorescent variant of LOV2 is provided. The variant is truncated such that the variant is 12 KDa or less in size, wherein the variant has a sequence that is at least 90% identical to SEQ ID NO 4, and wherein the variant has a fluorescent anisotropic lifetime that is greater than 4.0 ns.

In some embodiments, an isolated truncated and mutated sensor protein derived from LOV2 that is 12 KDa or less, genetically encoded for detection and imaging of protein complexes, the sensor protein having a sequence with at least 90% homology to SEQ ID NO 4 is provided.

In some embodiments, a sensor protein having 91, 92, 93, 94, 95, 96, 97, 98, or 99 percent (%) homology to SEQ ID NO: 4 is provided.

In some embodiments, a genetically encoded fluorescence protein having a mass that is about 20 kD or less, having a sequence that is at least 75% homologous to SEQ ID NO 4, and having a fluorescent anisotropic lifetime that is >4.0 ns is provided.

In some embodiments, an isolated polynucleotide that when translated, provides for a protein having a sequence comprising SEQ ID NO 4, is provided.

Embodiments provided herein can relate to systems and methods for generating, detecting or imaging fluorescent proteins and their complexes encoded by engineered genes of full length and truncated flavoproteins and related proteins that bind to fluorescent forms of flavin, ribityllumazine and their precursors or exogenously added derivatives for applications in the study and analysis of protein and DNA complexes in basic research, diagnostics and biomarker detection.

In some embodiments, an isolated truncated and mutated sensor protein derived from LOV2 that is 12 KDa or less, genetically encoded for detection and imaging of protein complexes is provided. The sensor protein has a sequence comprising SEQ ID NO:3.

In some embodiments, a sensor protein having 50, 60, 70, 75, 80, 85, 90, 91, 92, 93, 94, 95, 96, 97, 98, 99 percent (%) homology to SEQ ID NOS: 3 or 4 is provided.

In some embodiments, a genetically encoded fluorescence protein having a small mass that is about 20 kD or less, having a sequence that is at least 75% homologous to SEQ ID NOS:3 or 4, and having a fluorescent lifetime that is >4.0 ns is provided.

In some embodiments, an isolated polynucleotide that when translated, provides for a protein having a sequence comprising SEQ ID NOS: 3 or 4 is provided.

In some embodiments, an isolated truncated and mutated sensor protein derived from LUMP that is 12 KDa or less is provided. It is genetically encoded for detection and imaging of protein complexes, the sensor protein having a sequence comprising SEQ ID NO: 6, 7, 8 or 9. An embodiment of the nucleotide sequence encoding an embodiment of the LUMP protein is shown in FIG. 11H (SEQ ID NO: 7).

In some embodiments, a sensor protein having 50, 60, 70, 75, 80, 85, 90, 91, 92, 93, 94, 95, 96, 97, 98, 99 percent (%) homology to SEQ ID NOS: 6, 7, 8 or 9 is provided.

In some embodiments, a genetically encoded fluorescence protein having a small mass that is about 20 kD or less, having a sequence that is at least 75% homologous to SEQ ID NOS: 6, 7, 8 or 9, and having a fluorescent lifetime that is >4.0 ns is provided.

In some embodiments, an isolated polynucleotide that when translated, provides for a protein having a sequence comprising SEQ ID NOS: 6, 7, 8 or 9 is provided.

In some embodiments, an isolated fluorescent variant of Lov2 is provided. The variant is truncated such that the variant is 12 kDa or less in size. The variant has a sequence that is at least 90% identical to SEQ ID NO: 3 or 4, and the variant has a fluorescent lifetime that is greater than 4.5 ns.

In some embodiments, an isolated fluorescent variant of LUMP is provided. The variant is truncated such that it is 20 kDa or less in size. The variant has a sequence that is at least 90% identical to SEQ ID NO: 6, 7, 8 or 9, and the variant has a fluorescent lifetime that is greater than 4.5 ns.

In some embodiments, a fluorescent anisotropy based sensor is provided. The sensor comprises a targeting molecule and a fluorescent molecule that is covalently linked to the targeting molecule. The fluorescent molecule is a truncated variant of the protein within SEQ ID NO: 3, 4, 8, or 9, wherein the truncated variant is no greater in size than about 12 KDa. The truncated variant comprises an amino acid sequence that is at least 90% identical to SEQ ID NO: 3, 4, 6, 7, 8, or 9, for a section of the sequence that is present in the truncated variant, and wherein the truncated variant has a fluorescent lifetime of greater than 4 ns.

In some embodiments, a method of detecting a target molecule is provided. The method comprises providing an amino acid based fluorescent molecule. The fluorescent molecule is covalently linked to a targeting molecule that binds to the target molecule, and the fluorescent molecule has a fluorescent lifetime that is greater than 4.0 ns. The method further includes adding the fluorescent molecule to a sample and detecting if there is a change in fluorescent anisotropy of the fluorescent molecule as a result of its binding to a target molecule.

BRIEF DESCRIPTION OF THE DRAWINGS

FIG. 1A depicts, fLov2 (10 kD) fused to a 2.5 kD LiveAct actin binding peptide (HR1b). The unbound sensor has τc of ~5 ns and given a $\tau_f$ of 4.5 ns the calculated FA value in buffer is 0.22. Upon binding to actin, τc increases to 22 ns with a FA value of >0.3.

FIG. 1B depicts, Y1 (20 kD) fusion with GBD (5 kD) has a calculated $\tau_c$ of 10 ns, increasing to 18 ns on binding to Cdc42 (with the calculated change in FA being from 0.23 to 0.31).

Figure 4:
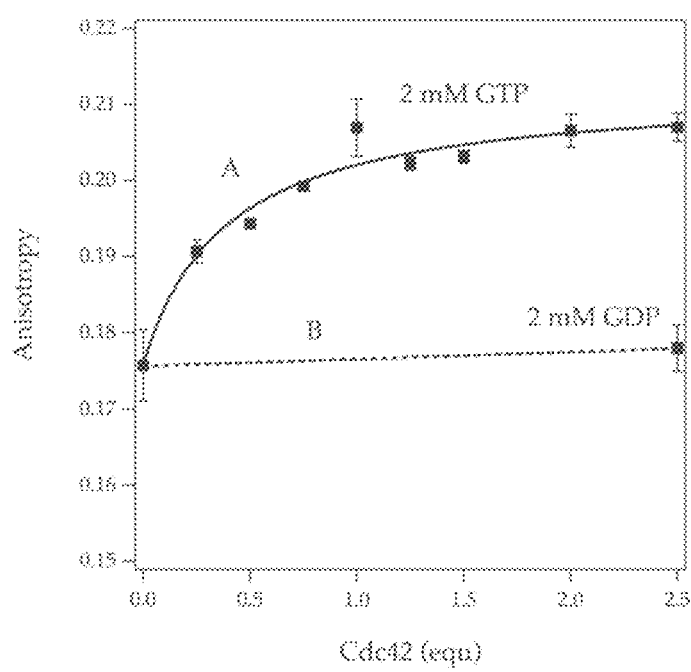

FIG. 4 depicts a FA-based stoichiometric titration of LUMP-GBD (SEQ ID NO: 15) (10 μM) with GTP-bound cdc42 showing a 1:1 complex. A is in an aqueous buffer of 20 mM Tris, pH=8, 50 mM NaCl, 2 mM GTP. B is in an aqueous buffer of 20 mM Tris, pH=8, 50 mM NaCl, both at 20° C.

Figure 5:
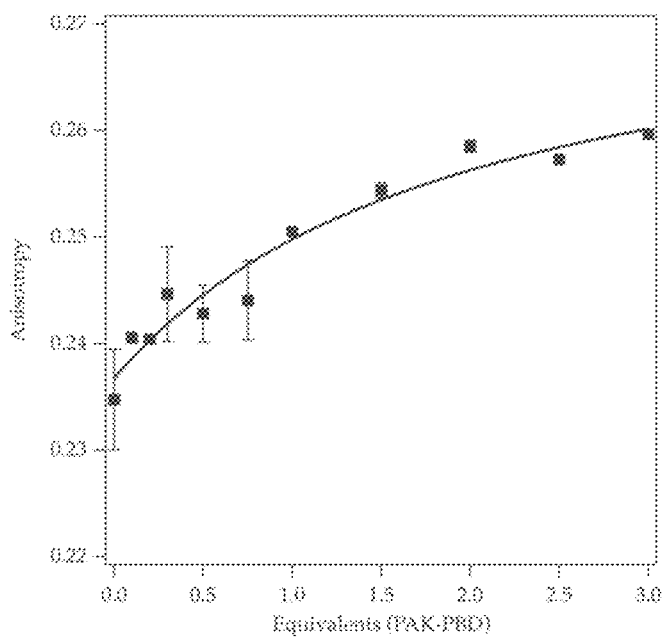

FIG. 5 depicts a FA-based stoichiometric titration of GTPT bound LUMP-cdc42 (10 microM) with PAK-PBD in aqueous buffer (20 mM Tris, pH=8, 50 mM NaCl) at 20° C. showing a 1:1 complex.

FIG. 6A depicts a Fluorescence image of the parallel polarized emission of surface about bacteria expressing LUMP-GBD (20 kD fluorescence in *E. coli* using a modified laser scanning confocal microscope (Zeiss, LSM 700, 20× objective, NA=0.7).

FIG. 6B depicts a Fluorescence image of the perpendicular polarized emission of surface about bacteria expressing LUMP-GBD (20 kD fluorescence in *E. coli* using a modified laser scanning confocal microscope (Zeiss, LSM 700, 20× objective, NA=0.7).

FIG. 6C, Image of the calculated FA values of LUMP-GBD in *E coli* (20 kD fluorescence in *E. coli* using a modified laser scanning confocal microscope (Zeiss, LSM 700, 20× objective, NA=0.7).

Figure 7:
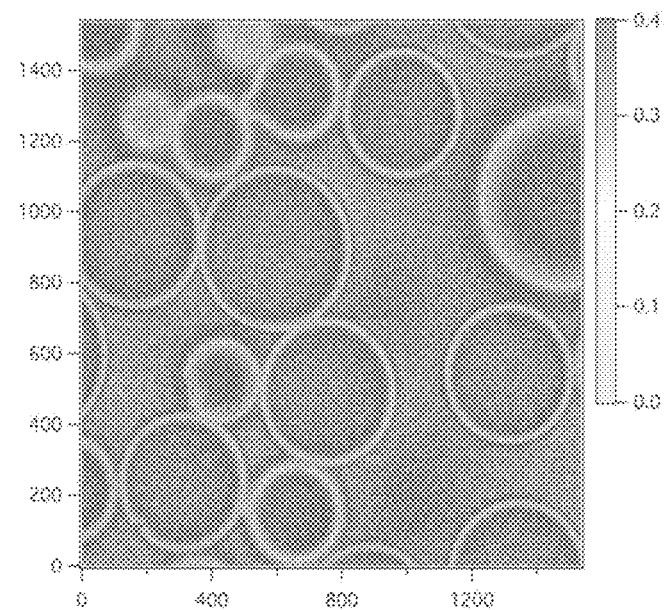

FIG. 7 depicts the fluorescence Anisotropy image of LUMP (His-tagged) bound to individual Ni-NTA-coupled Sepharose beads. The bound LUMP exhibits an FA value of 0.34, which is close to its limiting anisotropy value. LUMP was immobilized on Ni-NTA agarose beads with a N-terminal 6-histidine peptide tag. Residual LUMP fluorescence is seen in the interstitial spaces with an anisotropy of r=0.16, matching the cuvette-based measurement almost perfectly. The 15 amino acid linker between 6His and LUMP allows for enough mobility of the globular protein fluorophore to reduce its anisotropy from r0=0.38 to r=0.34. It is noteworthy, that these large anisotropy values are observed further towards the inside of the bead and that intermediate anisotropy values (0.2<r<0.3) are observed at the outer surface of the bead. This highlights an advantage of Anisotropy imaging over intensity—based approaches in that for the same intensity, protein mobility related microenviromnents are detected that could result from the density of the binding environment as in our case here. In other cellular cases, one can detect differences between mere proximity and actual tight binding (low entropy) events that could be distinguished by fluorescence anisotropy but not by intensity or colocalization approaches.

Figure 8:
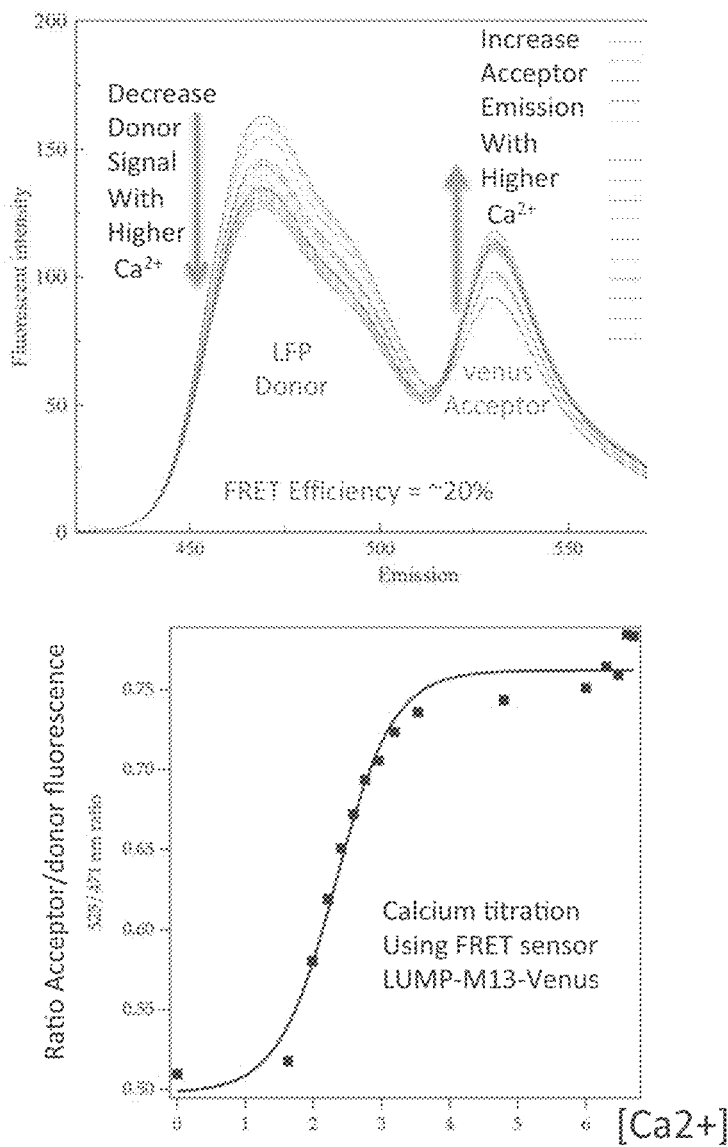

FIG. 8 shows the application of LUMP as a CFP-like donor probe in FRET with a Venus acceptor probe in a calcium ion FRET sensor.

FIG. 9 depicts the structure of the monomeric form of riboflavin synthase.

Figure 10A:
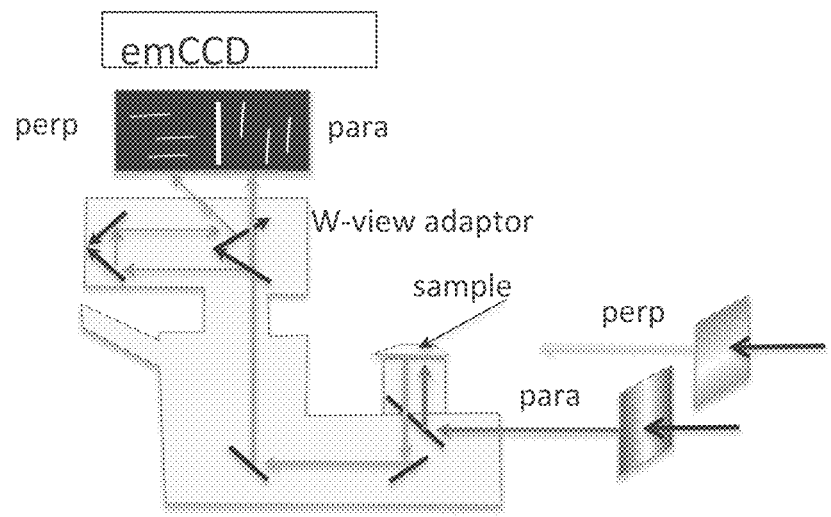

FIG. 10A Depicts a schematic of the fluorescence anisotropy imaging microscope.

FIG. 10B depicts the dependence of the measured anisotropy value on the numerical aperture of the objective lens (after Yan and Marriott 2003).

FIG. 11A depicts sequences (SEQ ID NO: 12 and SEQ ID NO: 13) relating to Y1 embodiments.

FIG. 11B depicts sequences (SEQ ID NO: 10 and SEQ ID NO: 11) relating to N-RFS embodiments.

FIG. 11C depicts the sequence of an embodiment of a protein for the nucleotide-binding flavoprotein NPH1-1 and also called LOV2 from *Avena sativa* (Oat) (GeneID: O49003, the GenBank Accession) (SEQ ID NO: 1).

FIG. 11D depicts SEQ ID NO: 2 which is an embodiment of the nucleotide sequence encoding the protein of SEQ ID NO: 1 shown in FIG. 11C.

FIG. 11E depicts SEQ ID NO: 3 (an embodiment of mLOV2).

FIG. 11F depicts SEQ ID NO: 4 (an embodiment of fLOV2).

FIG. 11G depicts SEQ ID NO: 6 (an embodiment of a LUMP protein).

FIG. 11H depicts SEQ ID NO: 7 (an embodiment a LUMP nucleic acid sequence).

FIG. 11I depicts SEQ ID NO: 8 (an embodiment of a mLUMP construct).

FIG. 11J depicts SEQ ID NO: 9 (an embodiment of a modified full length LUMP protein).

Figure 12:

FIG. 12 depicts the crystal structure of an embodiment of LUMP with surface bound ribityl-lumazine.

Figure 13:
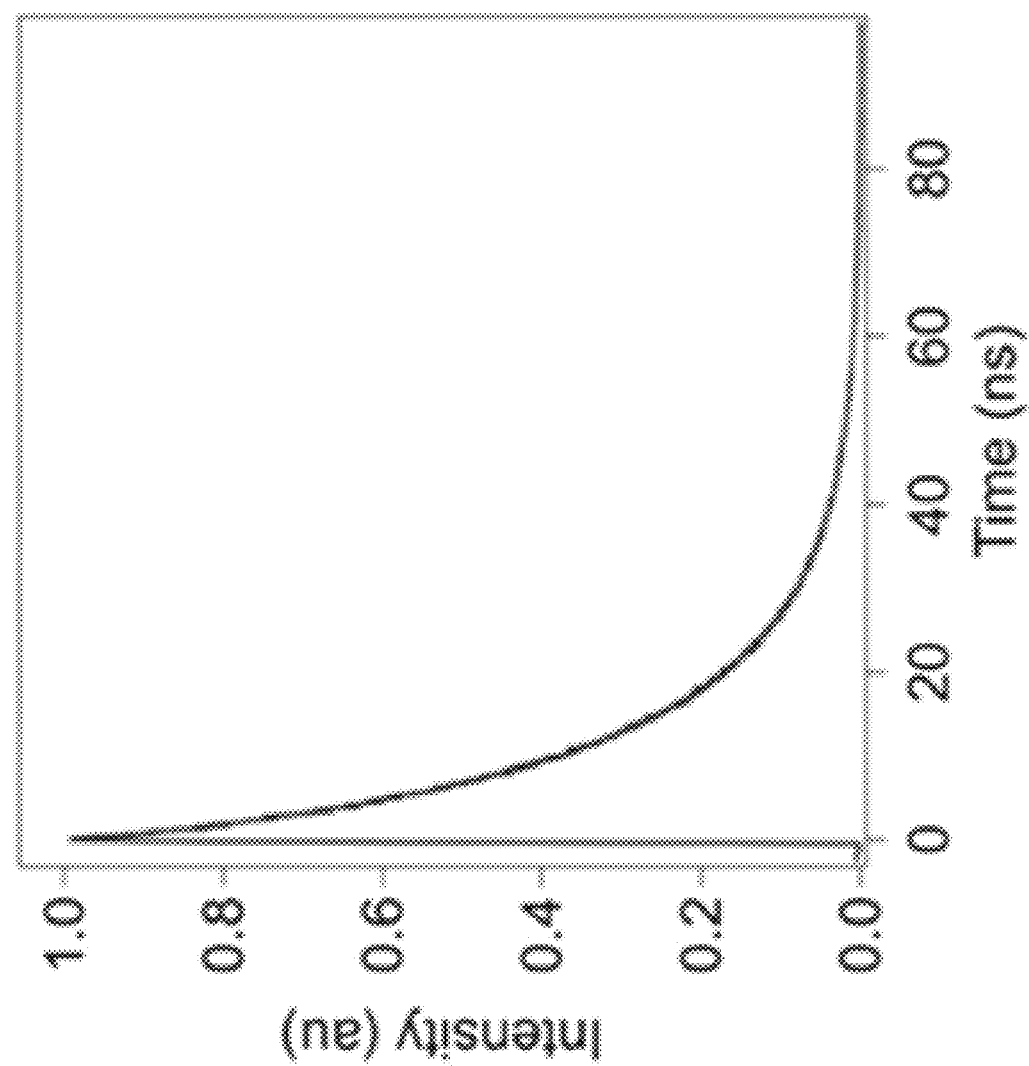

FIG. 13 depicts time-resolved fluorescence intensity decay of an embodiment of LUMP.

Figure 14:
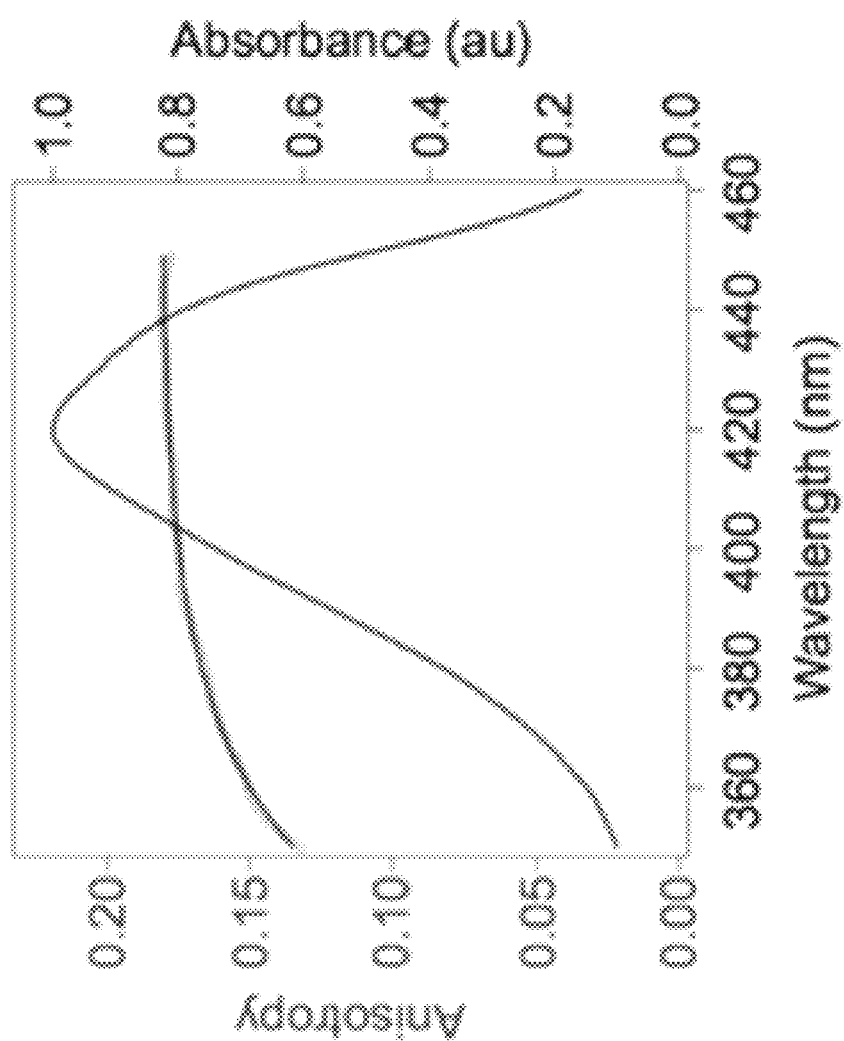

FIG. 14 depicts excitation anisotropy scan with fluorescence emission at 470 nm superimposed on absorbance scan of an embodiment of LUMP in a viscous medium [75% (mass/volume) sucrose].

Figure 15:
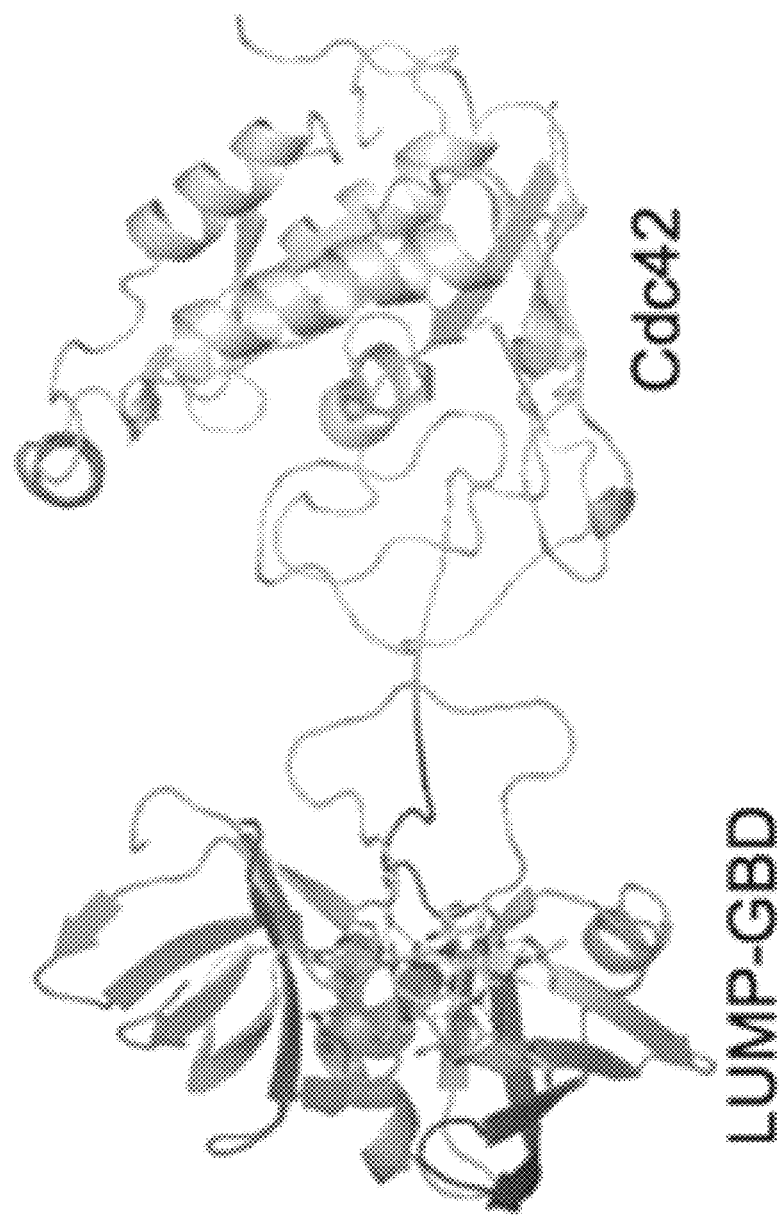

FIG. 15 is an illustration of the of crystal structures of an embodiment of LUMP and GBD-Cdc42 with the flexible six-amino acid linker GSGSAS (SEQ ID NO: 29).

Figure 16:
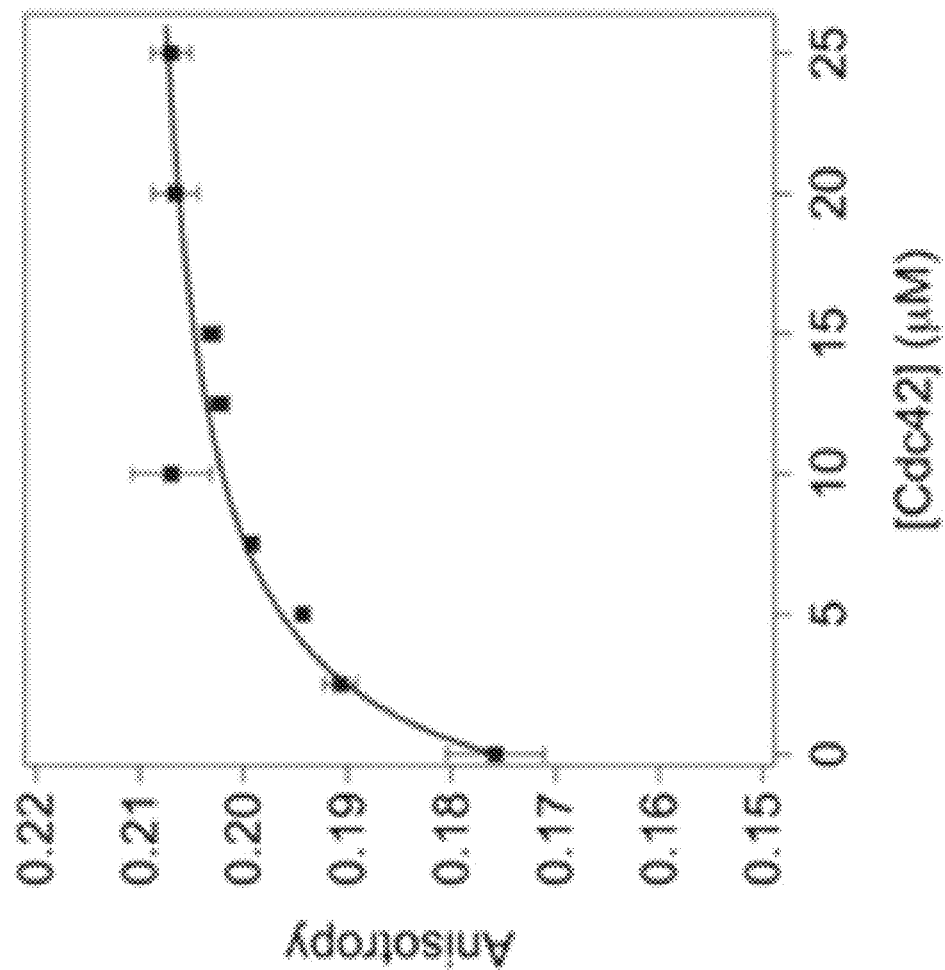

FIG. 16 depicts FA plot of an embodiment of GBD-LUMP (SEQ ID NO: 15) vs. titrated equivalents of Cdc42 in aqueous buffer [20 mM Hepes (pH 7.9), 150 mM NaCl, 2 mM GTP] at 20° C. showing binding of a fixed concentration of LUMP-GBD to varying levels of GTP-bound Cdc42.

Figure 17:
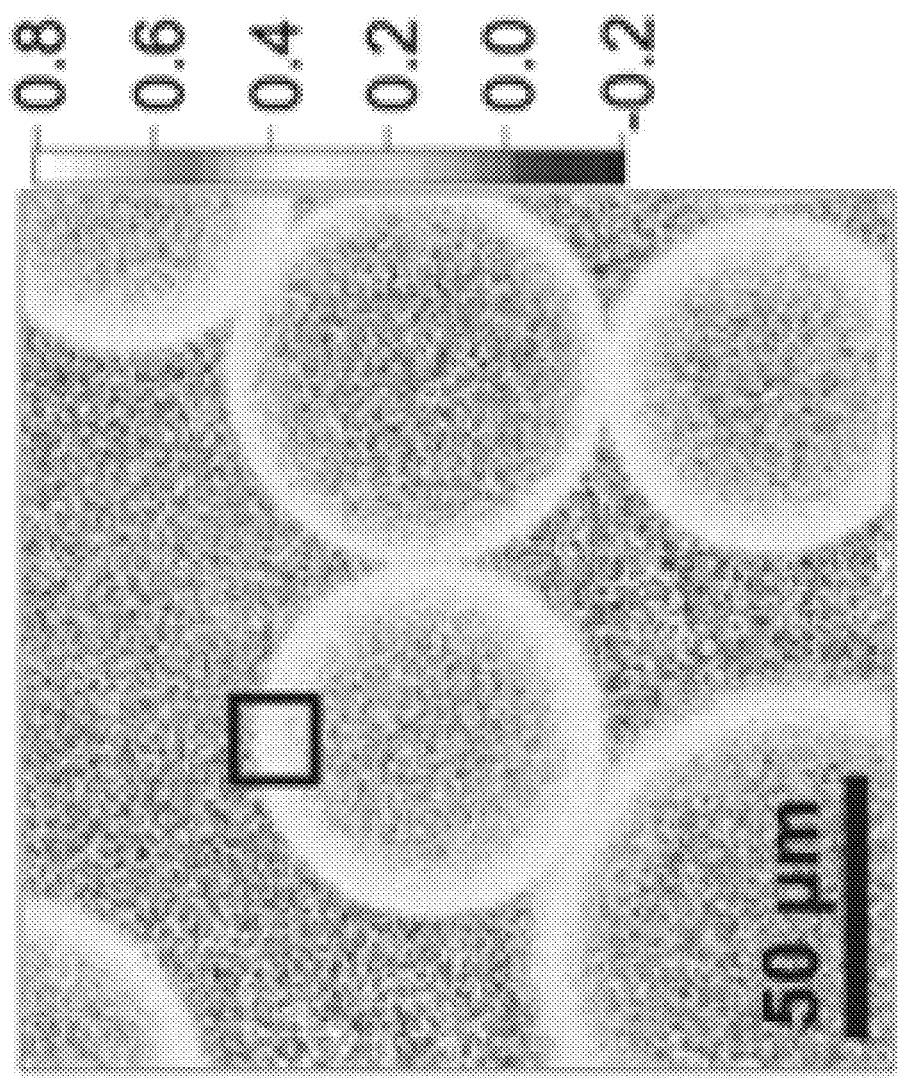

FIG. 17 shows anisotropy image of an embodiment of His-tagged LUMP on Ni-NTA agarose beads with an average of r ($r_{avg}$)=0.310.

Figure 18:
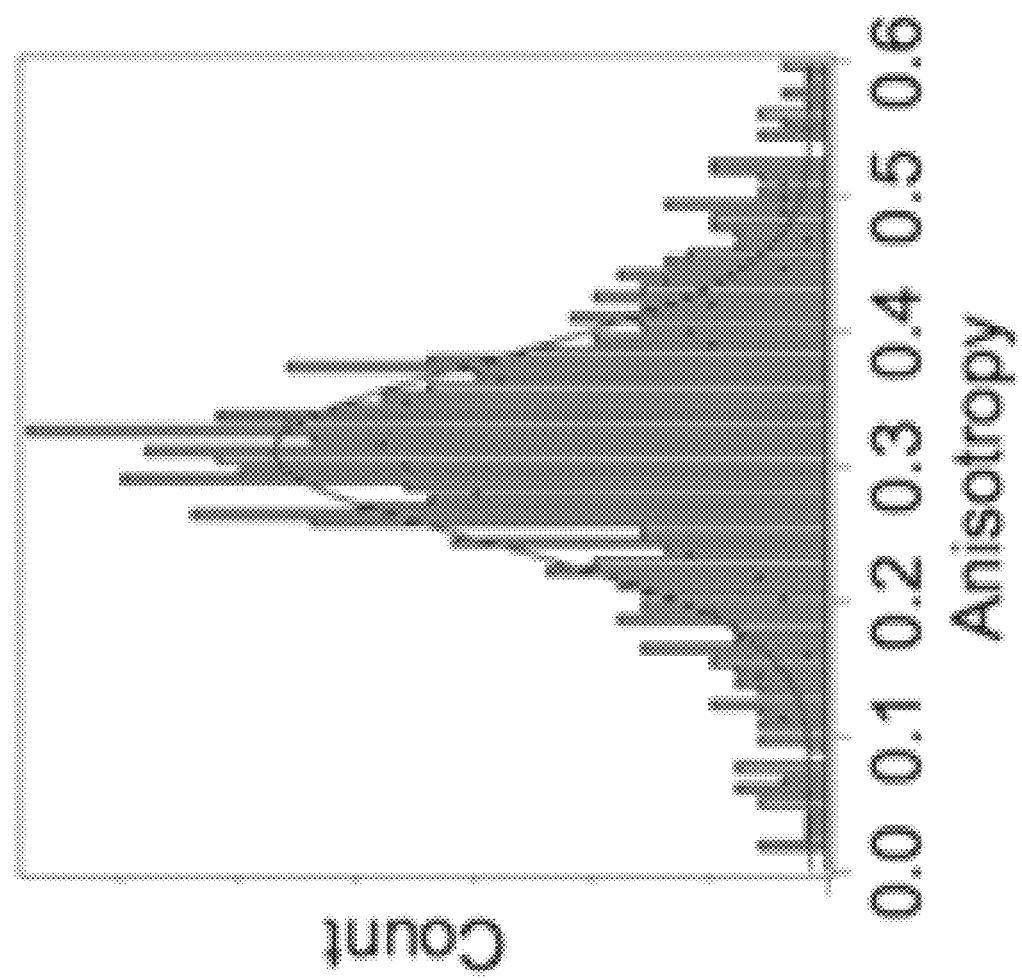

FIG. 18 shows anisotropy distribution of the selected region in FIG. 17 with $r_{avg}$=0.311±0.002.

FIGS. 19A-19D show fluorescence intensity and anisotropy images of unlabeled agarose beads with 10 μM of an embodiment of His-tagged LUMP in buffer at 20° C.

Figure 19A:
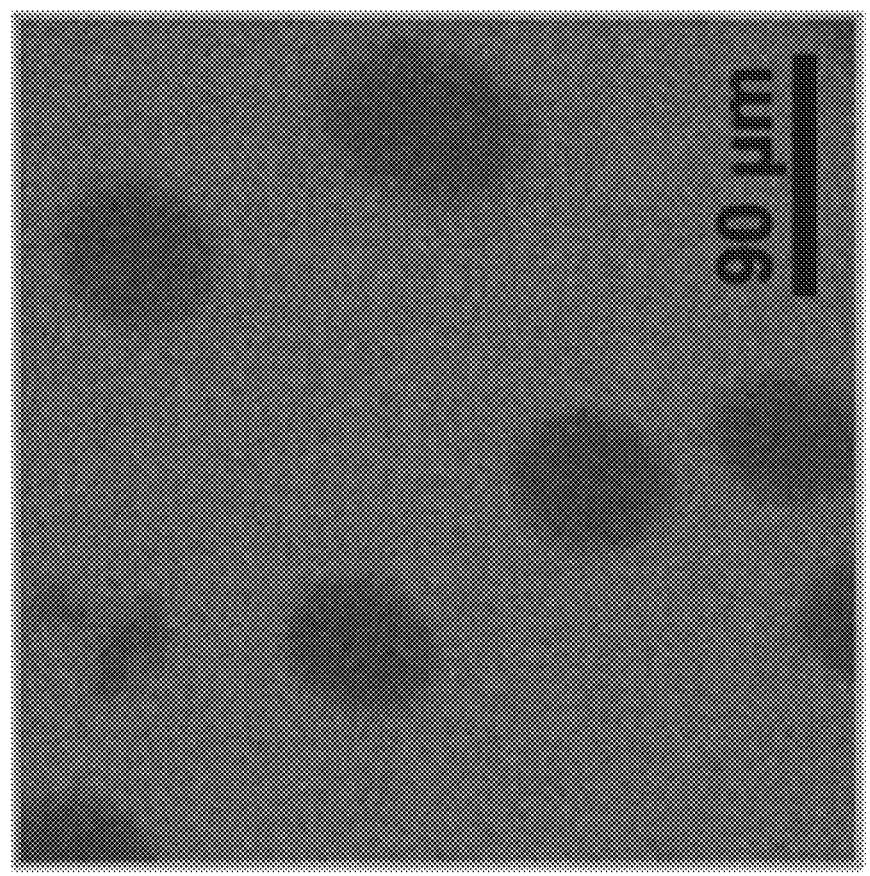

FIG. 19A shows fluorescence intensity image of unlabeled agarose bead showing no intensity at the bead.

Figure 19B:
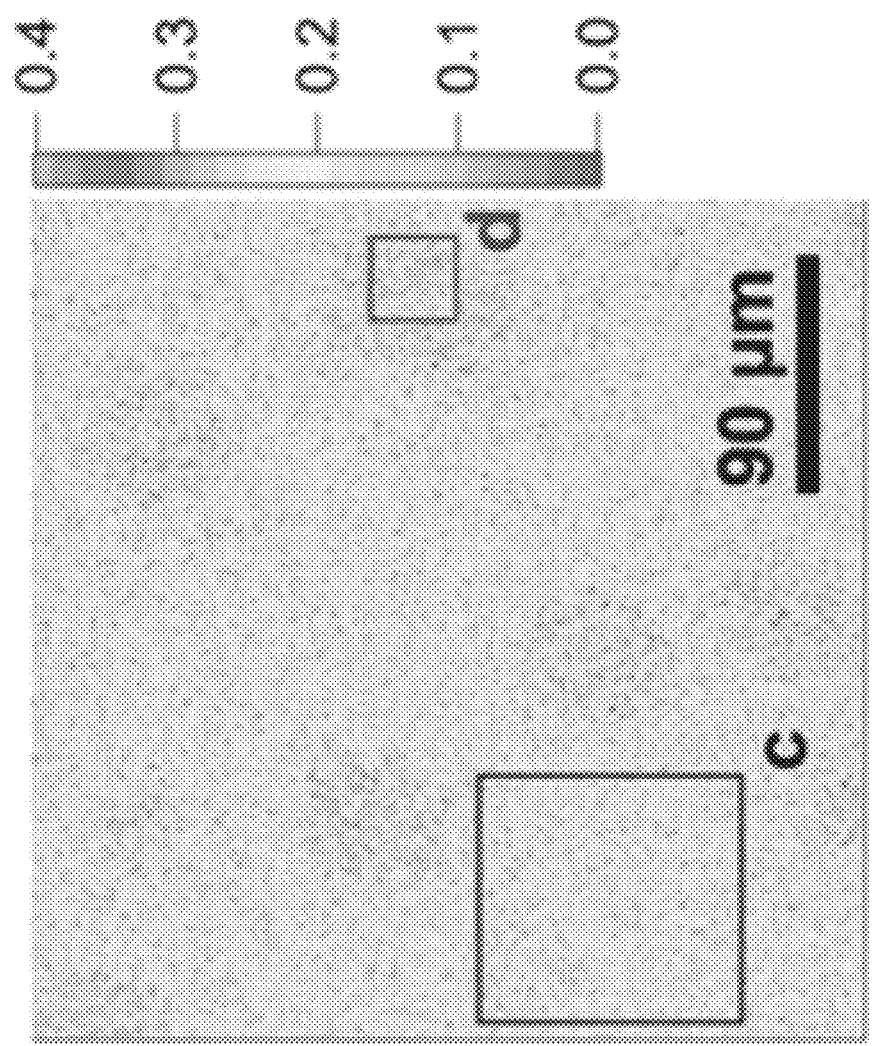

FIG. 19B shows FA image obtained from P- and S-polarized images with a G-factor of 0.78.

Figure 19C:
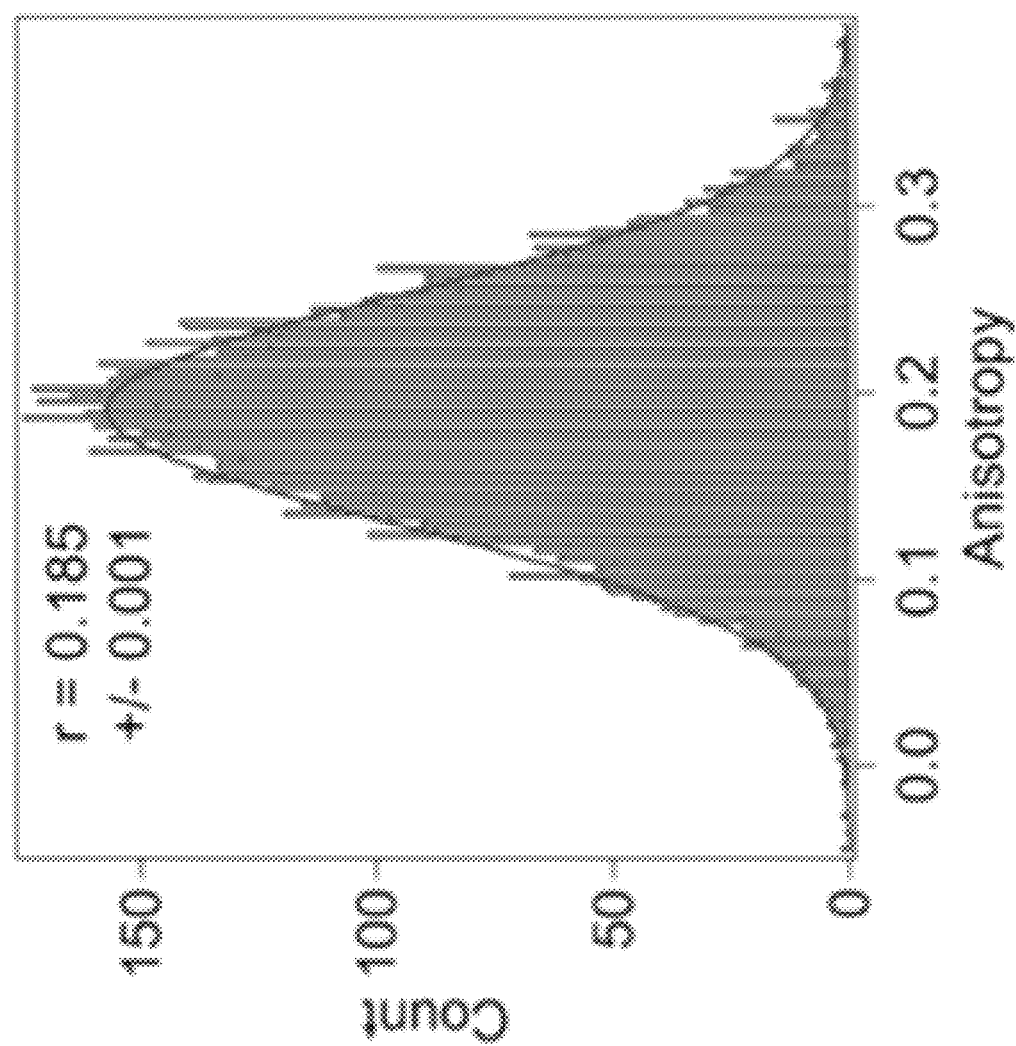

FIG. 19C shows anisotropy distribution of box c in FIG. 19B. The anisotropy of 0.185 matches the anisotropy obtained from SLM-AB (2 fluorometer measurement of His-LUMP. For comparison, LUMP without the His-tag measures 0.166, as referenced earlier.

Figure 19D:
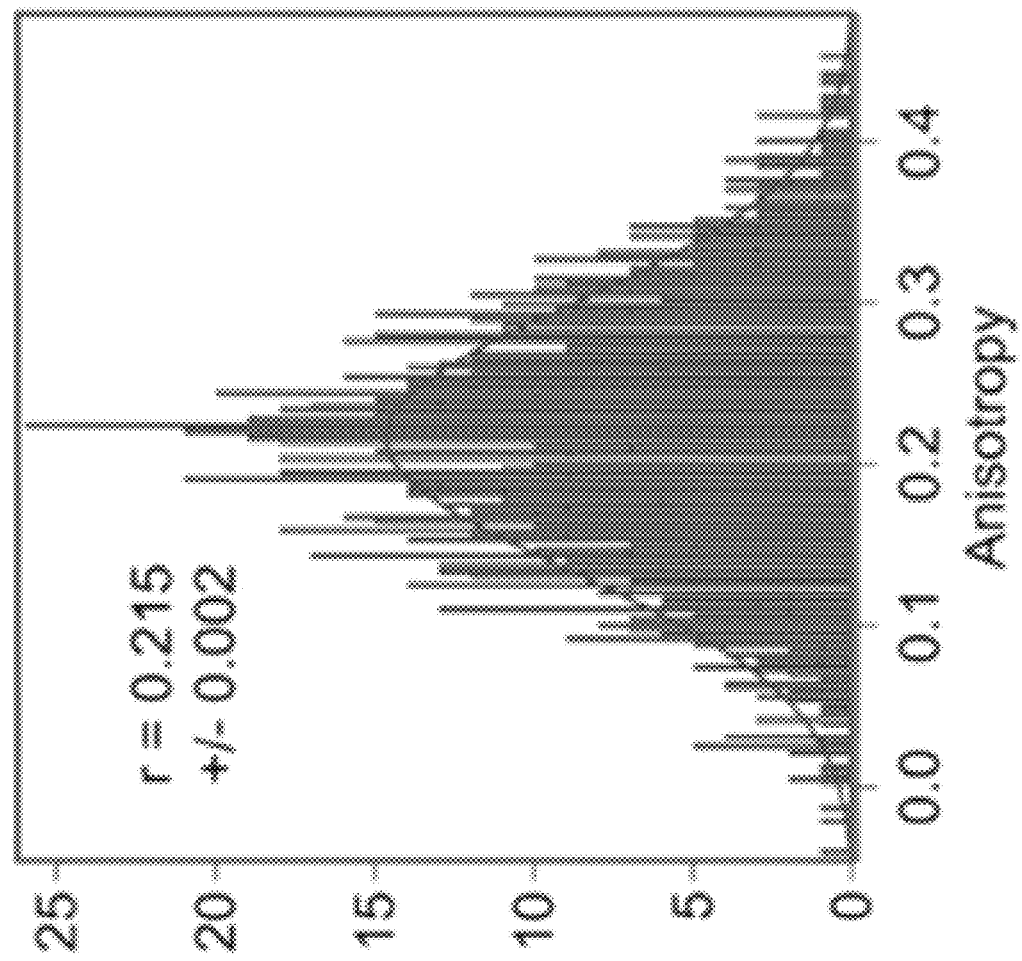

FIG. 19D shows anisotropy distribution of box d in FIG. 19B.

Figure 20A:
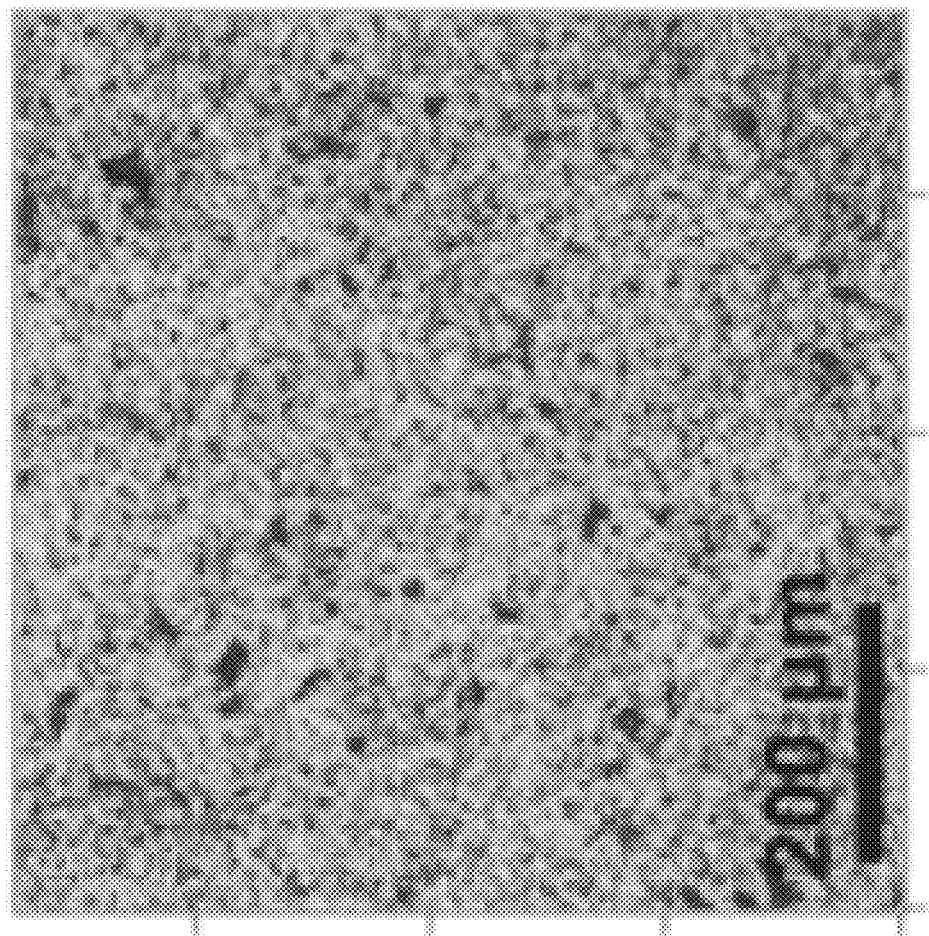

FIG. 20A shows P-polarized (parallel) emission image of *E. coli* cells in PBS buffer expressing an embodiment of GBD-LUMP and Cdc42 (Q61L) in a double-expression vector.

Figure 20B:
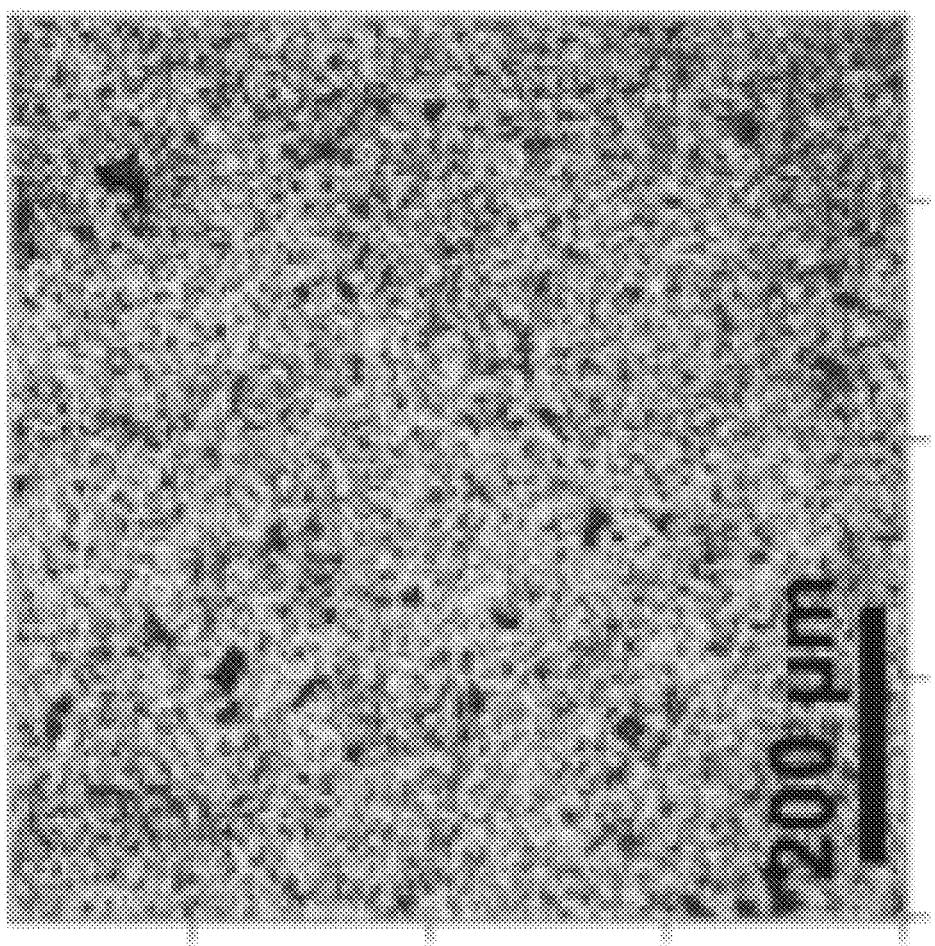

FIG. 20B shows S-polarized (perpendicular) emission images of *E. coli* cells in PBS buffer expressing an embodiment of GBD-LUMP and Cdc42 (Q61L) in a double-expression vector.

Figure 20C:
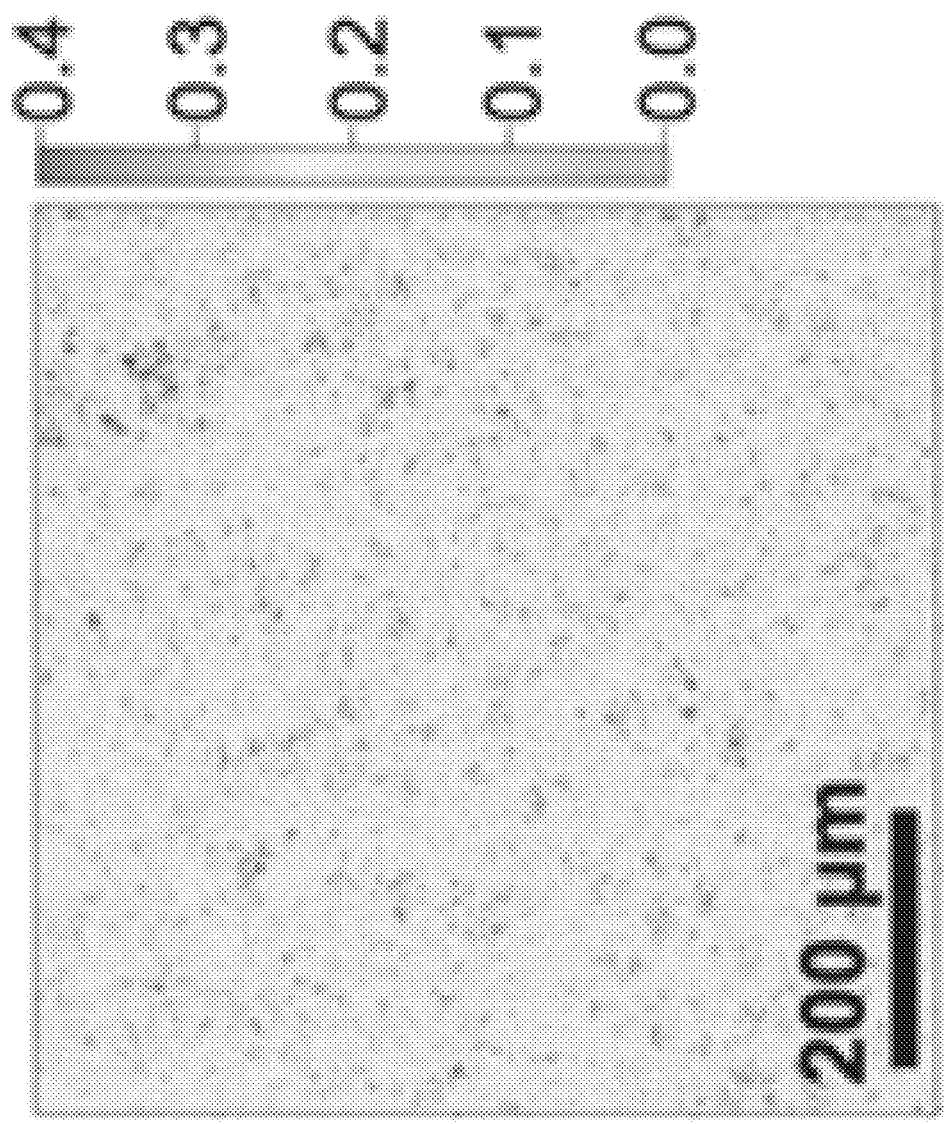

FIG. 20C shows anisotropy image obtained from P- and S-polarized images (FIGS. 20A and B) using a G-factor of 0.78.

FIG. 20D shows anisotropy distribution of anisotropy image in FIG. 20C with $r_{avg}$=0.233.

FIG. 21A-21D show kinetic study of an embodiment of 10 μM Venus-thrombin-LUMP in aqueous buffer [20 mM Hepes (pH 7.9), 150 mM NaCl] at 20° C. with addition of 2.5 ng/μL thrombin protease.

Figure 21A:
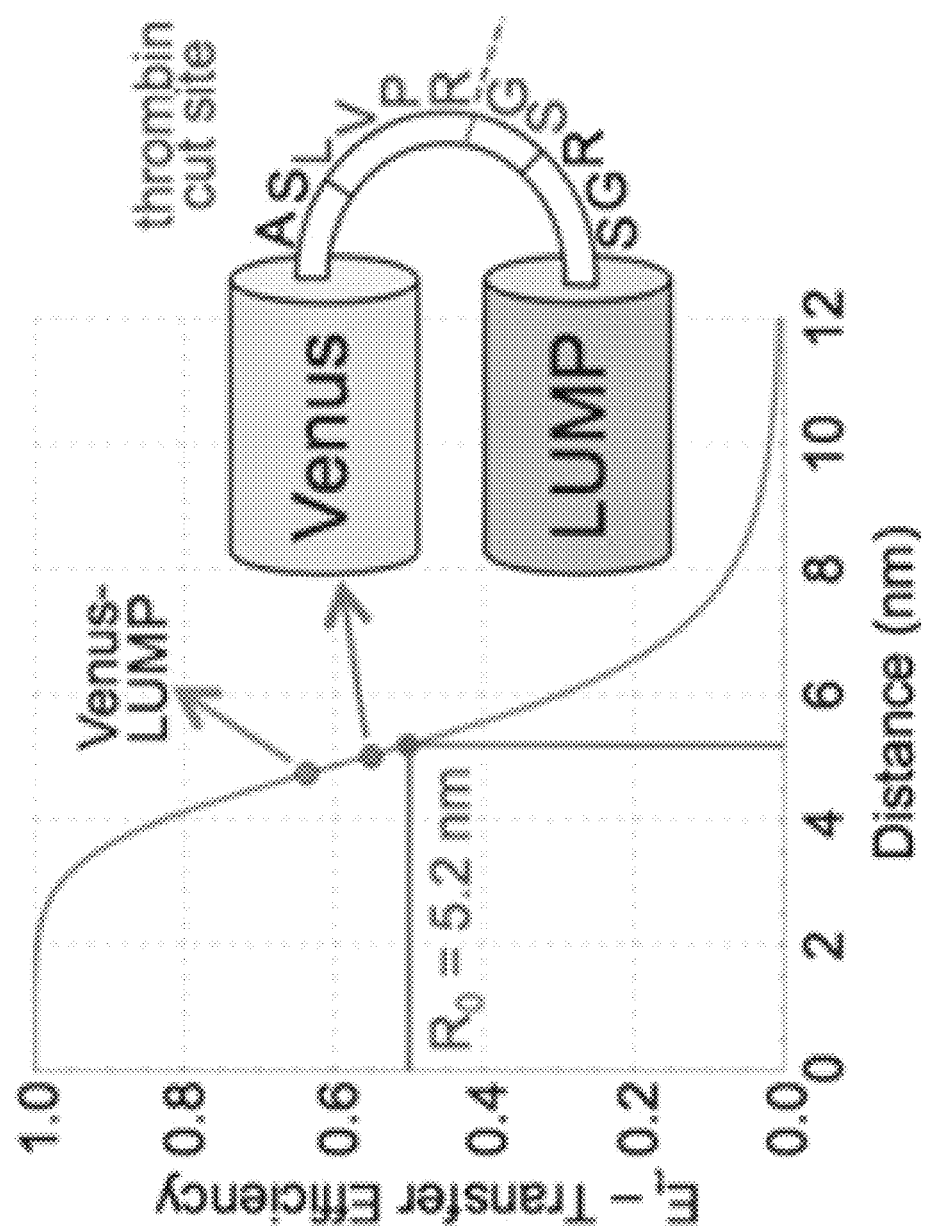

FIG. 21A shows FRET efficiency summary of an embodiment of minimum linker Venus-LUMP (SEQ ID NO: 16) (top dot) and an embodiment of Venus-thrombin-LUMP (SEQ ID NO: 17) (bottom dot) FRET probes relative to the $R_0$ of 5.2 nm.

Figure 21B:
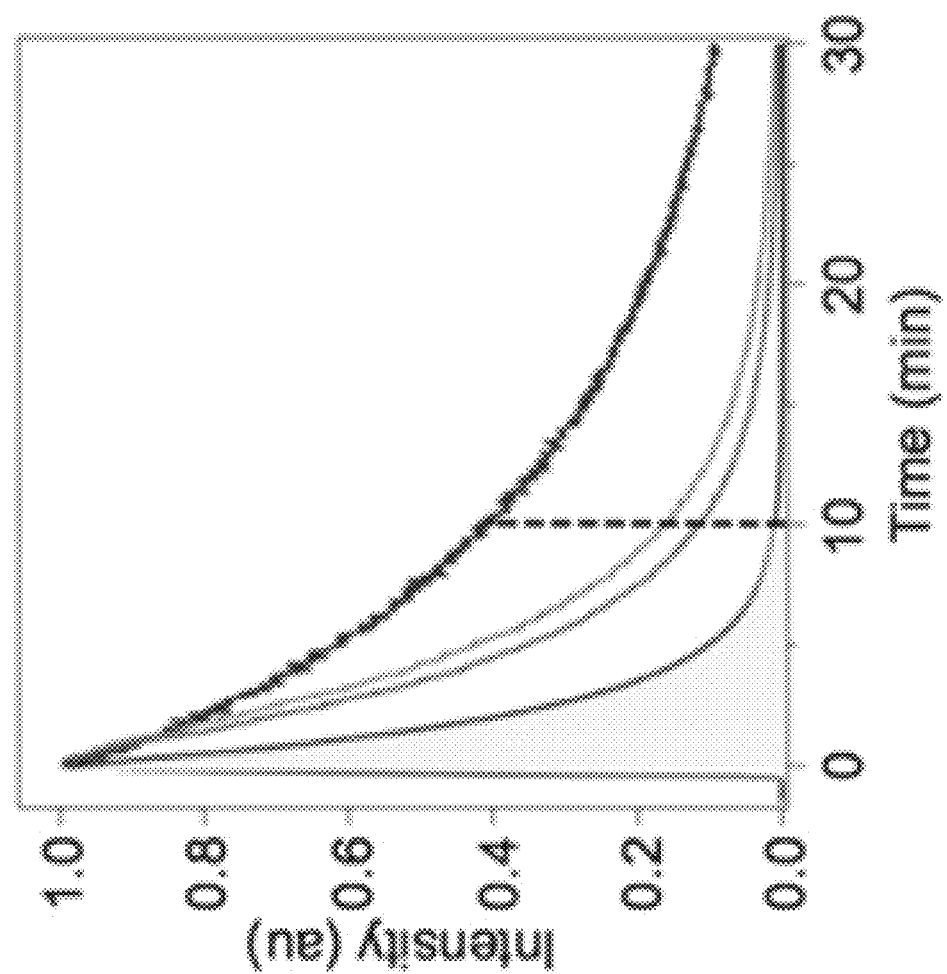

FIG. 21B shows fluorescence decays of LUMP and FRET probes. The simulated fluorescence decay of CFP with lifetime $\tau_f$=2.2 ns (first curved line from left), an embodiment of LUMP (fourth curved line from left; SEQ ID NO: 14), an embodiment of Venus-thrombin-LUMP (third curved line from left; SEQ ID NO: 17), and an embodiment of Venus-LUMP (second curved line from left; SEQ ID NO: 16) are shown. The dashed line illustrates a potential 10-ns time gate resulting in almost complete suppression of CFP emission (illustrated by the area under the line representing CFP to the left of the dashed line) relative to LUMP emission.

Figure 21C:
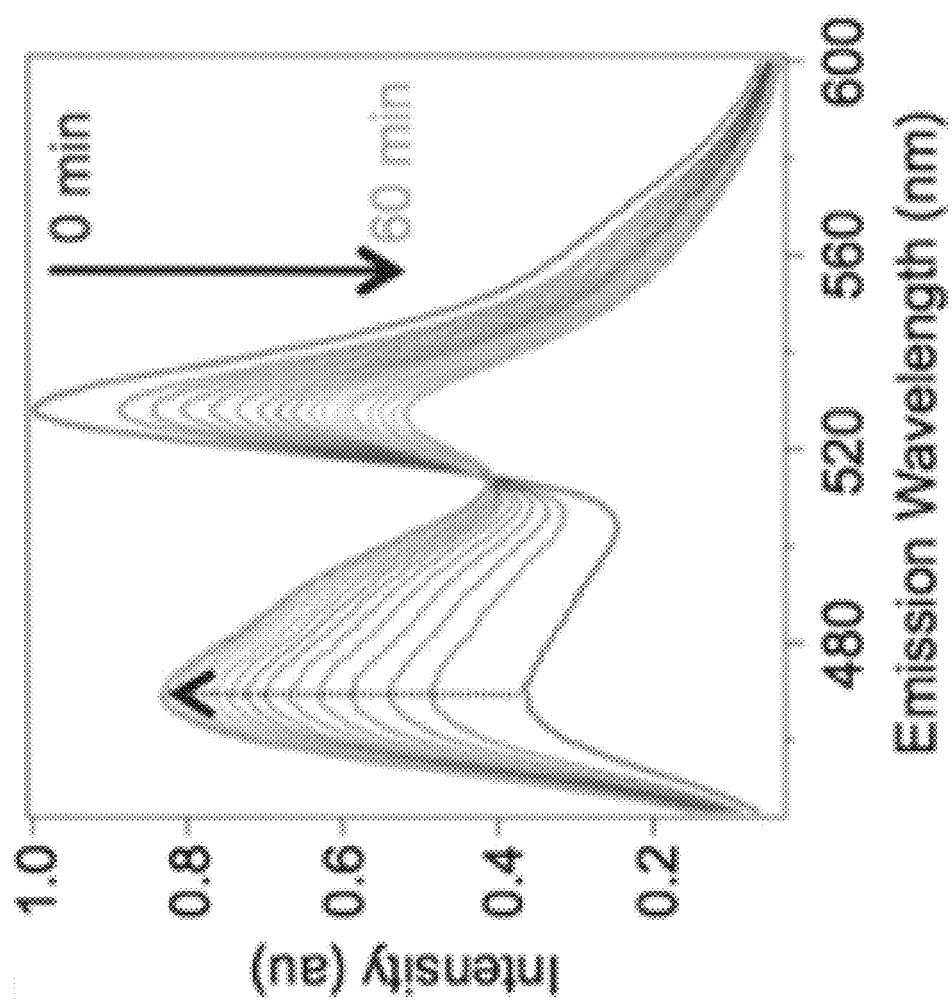

FIG. 21C shows fluorescence emission spectra of an embodiment of Venus-thrombin-LUMP vs. time after addition of thrombin. The time course is visualized with a curve shift from the bottom to the top for the left peak and curve shift from the top to the bottom for the right peak.

Figure 21D:
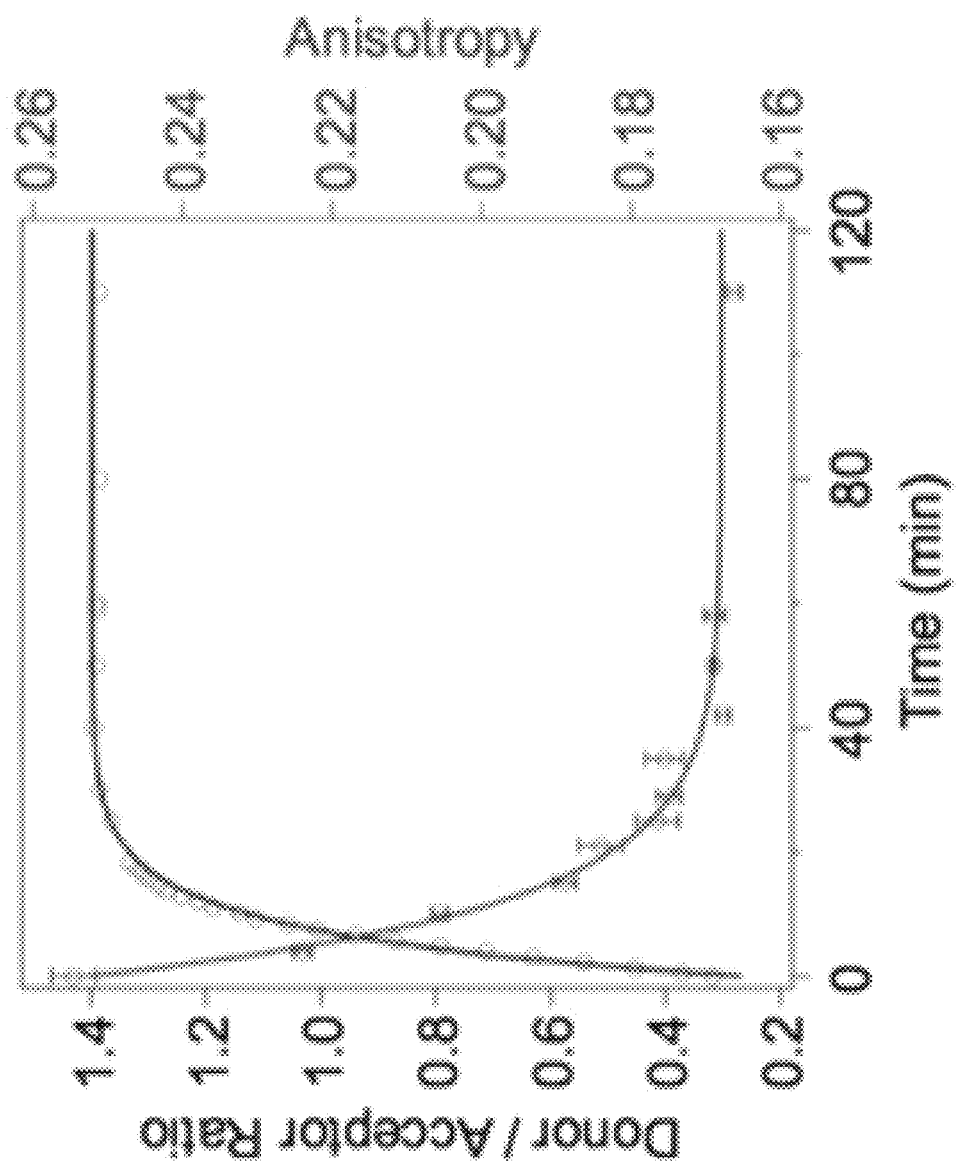

FIG. 21D shows FA (line from top left to bottom right) and donor/acceptor ratio (line from bottom left to top right) of fluorescence emission at 470 nm of an embodiment of Venus-thrombin-LUMP (SEQ ID NO: 17) vs. time.

FIG. 22 is the amino acid sequence of an embodiment of LUMP (SEQ ID NO: 14). The protein was purified with the affinity tag removed with TEV protease. The cut site is denoted by the symbol //.

FIG. 23 is the amino acid sequence of an embodiment of LUMP-GBD (SEQ ID NO: 15). The protein was purified with the affinity tag removed with TEV protease. The cut site is denoted by the symbol //.

FIG. 24 is the amino acid sequence of an embodiment of Venus-LUMP (SEQ ID NO: 16). The protein was purified with the affinity tag removed with TEV protease. The cut site is denoted by the symbol //.

FIG. 25 is the amino acid sequence of an embodiment of Venus-thrombin-LUMP (SEQ ID NO: 17). The protein was purified with the affinity tag removed with TEV protease. The cut site is denoted by the symbol //.

Figure 26:
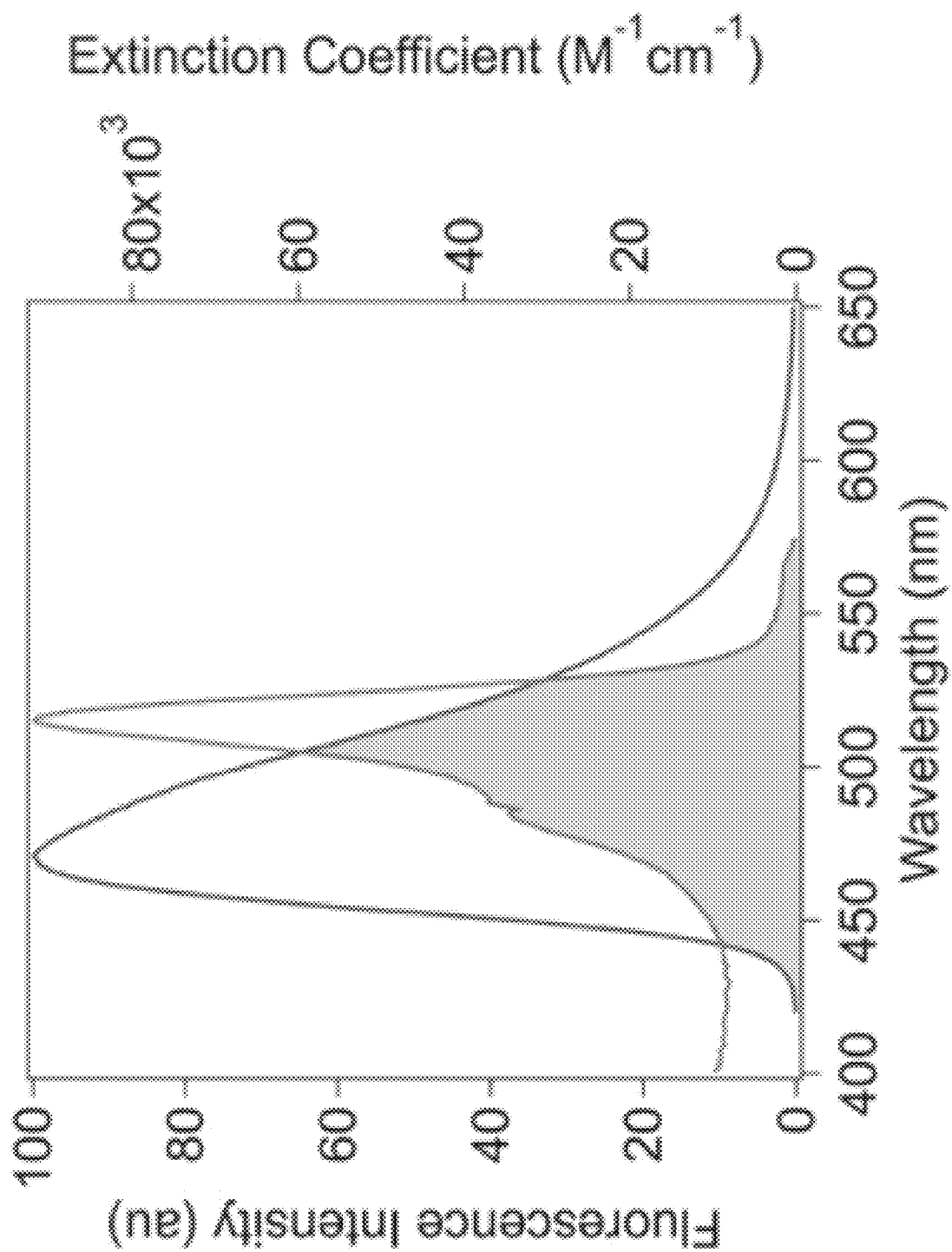

FIG. 26 shows peak-normalized absorption spectrum of an embodiment of Venus (right trace) superimposed on fluorescence emission spectrum of an embodiment of LUMP (left trace; SEQ ID NO: 14) in aqueous buffer [20 mM Hepes (pH 7.9), 150 mM NaCl] at 20° C. The shaded area indicates the overlap integral J(λ) that is used to calculate the Förster radius $R_0$.

Figure 27A:
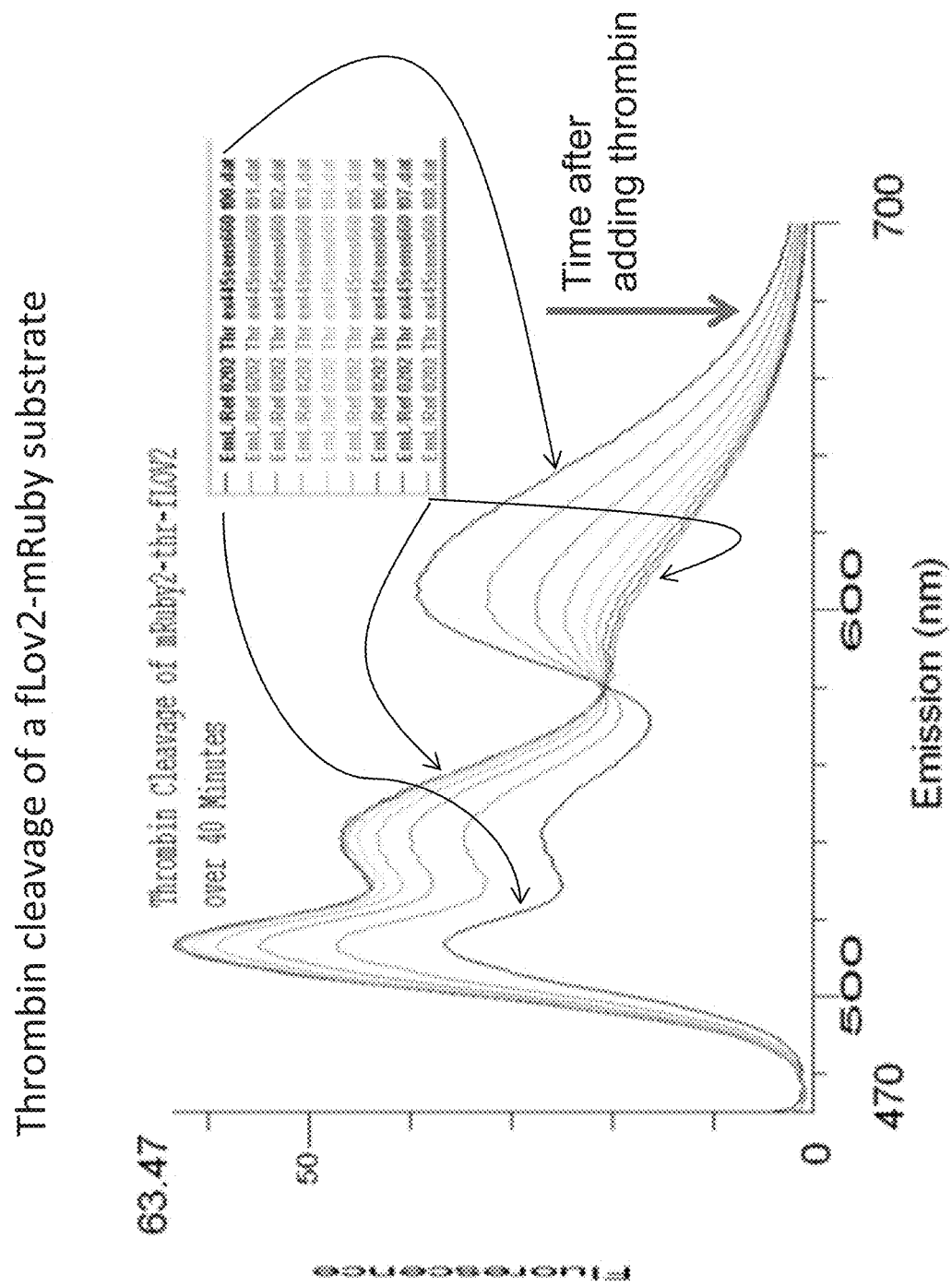

FIG. 27A is a graph depicting the emission spectra recorded as a function of time after the addition of thrombin.

Figure 27B:
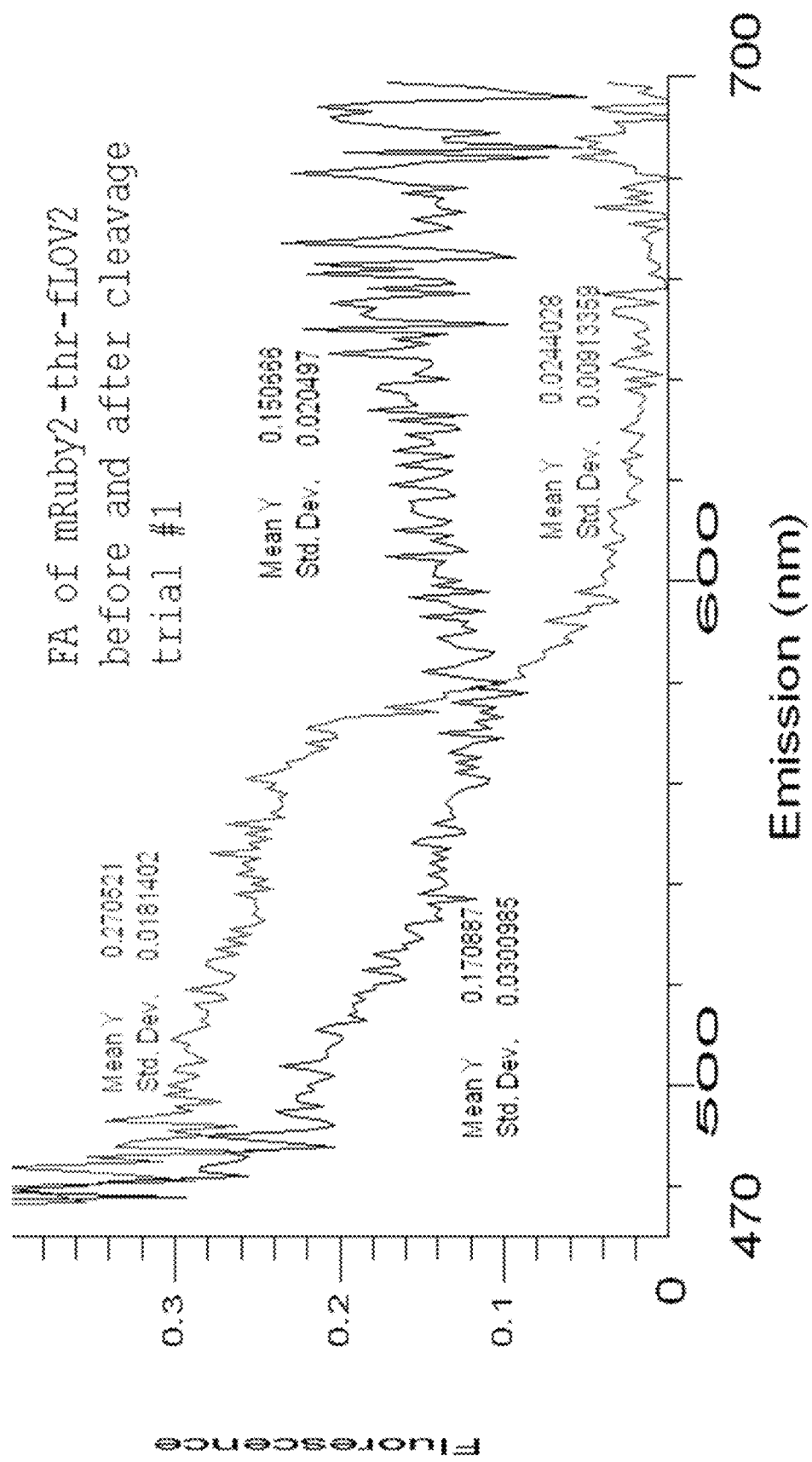

FIG. 27B depicts the anisotropy emission spectra of the substrate before and after cleavage with thrombin. FIG. 27C depicts the full amino acid sequence of the thrombin substrate (including a His-tag) used in example 16. FIG. 27D depicts the amino acid sequence of the fragment bearing mRuby2 after cleavage with thrombin in Example 16. FIG. 27E depicts the amino acid sequence bearing fLov2 after cleavage with thrombin in Example 16.

FIGS. 28A and 28B depict acceptor photobleaching of an mRuby2-coil-fLOV2 probe, expressed in HEK293T. The coil is spacer element from spider silk protein that is used in Vinculin tension sensor)

DETAILED DESCRIPTION

Fluorescence spectroscopy and microscopy are useful techniques for the detection and imaging of genetically encoded fluorescence proteins in vitro and in vivo. Fluorescence signals from these fluorescence proteins can be detected within multiple formats including living cells, multi-well microtiter plates, microfluidics devices and as single molecules using both fluorometers and microscopes. These detection instruments can be used with suitable genetically encoded proteins to measure the presence of specific proteins and their complexes to the level of single molecules for applications in biology, biotechnology and medical diagnosis.

A new type of genetically encoded protein, which can be distinct from GFP and related proteins are described herein. The genetically encoded protein may be derived from flavoproteins and their truncated, mutated versions. In other embodiments, systems and methods for the production of fluorescent proteins derived from or based on flavoproteins and expressed within plant, bacteria or within mammalian cells, such proteins whose emission signal can be detected with great sensitivity using a fluorescence microscope or fluorescence spectrophotometer. It has been appreciated that there is a need for effective new methods and approaches to develop new types of genetically encoded fluorescent protein for quantitative and qualitative applications related to detection and imaging of proteins and their complexes and related applications in diagnostics.

The new genetically encoded fluorescence proteins having a small mass that is about 20 kD (or smaller) and a relatively long lifetime that is >4.0 ns that may be used as a new type of probe for quantitative analysis of their hydrodynamic properties by using measurements of their fluorescence anisotropy (FA) measured in a microscope or in a fluorescence instrument. The combination of small volume (mass) and long fluorescence lifetime is unique to the new fluorescent proteins and result in a low value of the FA. In some embodiments, a fluorescent protein with a long (e.g., ~4.5 ns) lifetime having about 75% or less of the mass of conventionally used green-fluorescent protein (GFP). Because of their small hydrodynamic volume and long fluorescence lifetime, the present probes derived are well-suited for fluorescence anisotropy measurements of the size and shape of proteins and their complexes.

In some embodiments, engineered genes encoding the lumazine binding protein (LUMP, 20 kD) from *Photobacterium phosphoreum* (amino acid sequence of an embodiment of LUMP is shown in FIG. 22 (SEQ ID NO: 14)) or a modified and/or truncated form, mini-LUMP (mLUMP, 10 kD) are provided and/or used in fluorescent anisotropy measurements. LUMP binds to endogenous ribityllumazine in living cells, forming fluorescent complexes with high quantum yield ($\Phi_f$=0.54). The excitation spectrum of LUMP is centered at 420 nm and extends to 480 nm, while the emission band peaks at 470 nm, and is somewhat similar to CFP. LUMP and mLUMP have ~75% and 40% respectively of the mass of CFP and YFP. In some embodiments, bound lumazine exhibits a higher fluorescence quantum yield ($\Phi_f$=0.45) and longer-lived excited state lifetime ($\tau f$=14.5 ns) than its unbound form ($\Phi_f$=0.22, $\tau_f$=9.5 ns). In some embodiments, the fluorescence lifetime of LUMP is the longest of any genetically encoded protein at 14~15 ns.

In some embodiments, engineered genes encoding truncated mutant proteins of the Lov2 domain (fLov2, 12 kD) from *Avena sativa*, and protein Y1 from *Vibrio fisherei* strain Y1 are provided. Y1 and fLov2 protein and its derivatives bind to endogenous riboflavin in living cells, forming stable fluorescent complexes with a respectable quantum yield ($\Phi_f$>0.25). The excitation spectrum of fLov2 is centered at 460 nm and extends to 500 nm, while the emission band peaks at 520 nm, and is somewhat similar to YFP. fLov2 has ~40% of the mass of GFP and fluorescence lifetime of 4.5 ns.

In some embodiments, the strong fluorescence emission, and photo-stability of LUMP and fLov2 are used to image the actin cytoskeleton in living cells in fusion proteins with an additional sequence encoding LiveAct. The advantage of the new probes is that they have much smaller masses compared to CFP and YFP, which reduces the risk of their interfering with the activity of the target protein or in complex formation. LUMP has an unusually long fluorescence lifetime (14~15 ns), the longest of any genetically encoded protein. The fluorescence lifetime of purified fLov2 is ~4.5 ns, roughly ×2 that of GFP.

In some embodiments, the strong fluorescence emission, and photo-stability of fLov2 is used to image the actin cytoskeleton in living cells in fusion proteins with an additional sequence encoding LiveAct. In some embodiments, an advantage of the new probes is that they have much smaller masses compared to CFP and YFP, which reduces the risk of their interfering with the activity of the target protein or in complex formation. LUMP has an unusually long fluorescence lifetime (14~15 ns), the longest of any genetically encoded protein. The fluorescence lifetime of purified fLov2 is ~4.5 ns, more than ×2 that of GFP, while Y1 has a lifetime of 8 ns.

The low masses of fluorescent LOV2 derivatives (such as fLov2, LUMP and Y1, coupled with their long fluorescence lifetimes are exploited as part of a new genetically-encoded system for quantitative analysis of specific proteins and their complexes in vitro and in living cells. As shown herein, the FA value of a purified LUMP-fusion containing an additional short sequence is as low as 0.17 in buffer at 20 c, and can increase to close to the theoretical maximum value of 0.35 in viscous samples. This change would represents the largest difference in FA value between the free and bound states of any genetically encoded derived sensor protein.

In some embodiments, the FA value for a related fLov2 fusion proteins of mass ~15 kD increases from 0.22 in aqueous buffer at 20 c to the theoretical maximum (0.35) in viscous solution. This large dynamic range can be used for accurate determinations of target proteins in a sample or within a cell.

Fusion proteins of fluorescent Lov2 derivatives Y1 and LUMP in conjunction with fluorescence anisotropy can be used as part of a single-probe approach to image and quantify specific complexes, protein activity in living cells. The unique features (such as photophysical properties) of these flavoproteins and their fusion proteins can be applied to map protein complexes, or as FA-based sensors of proteolysis, where the FA-value would decrease after proteolysis, or as part of a new design strategy for genetically encoded probes of post-translational modifications including Ser/Thr/Tyr phosphorylation, and for secondary messengers, including calcium.

The small molecular mass and volume of fluorescent Lov2 derivatives (such as fLov2), LUMP and Y1 in combination with their long fluorescence lifetimes, make them superior donor probes compared to CFP and GFP in FRET with an acceptor (eg YFP). This improvement results from the fact that these smaller volume and longer lifetime of our new probes increases the Foerster distance (Ro) between fluorescent Lov2 derivatives (such as fLOV2), LUMP, or Y1 as the donor probe and an acceptor probe, compared to the CFP and GFP donor probes.

In some embodiments, by appending a targeting peptide (or targeting molecule) sequence to a fluorescent molecule (such as the fluorescent Lov2 derivatives (such fLov2, Y1 or LUMP), one can generate genetically-encoded hydrodynamic sensors that can be used to image/quantify almost any protein or a specific DNA or RNA sequence within a cell or sample. Since these sensors are produced in *E. coli*, they can be purified on a large scale, and used as diagnostic reagents to quantify almost any protein, DNA or other biomolecule or analyte in a sample. These reagents may be used as part of high throughput screening assays, based on FA or FRET measurements, to detect multiple proteins in a sample, or to analyze multiple samples using the same fusion protein.

In some embodiments, a protein engineering based strategy to reduce the mass of LUMP to as low as 10 kD without impacting the binding to ribityllumazine. This 10 kD probe (mLUMP) would be the smallest of any genetically encoded fluorescent protein.

In some embodiments a protein engineering based strategy is employed to red shift the absorption and emission spectra of LUMP and fLov2 to the red by using a DNA shuffling strategy with residues in the red-shifted protein Y1 to the cofactor-binding site serving as a guide.

In some embodiments, these latter probes would be more suitable for in vivo sensing of target biomolecules using the FA technique.

In some embodiments a protein engineering based strategy is used to covalently link the cofactor to the FA-sensor both in vivo and in vitro. This feature will allow one to significantly increase the sensitivity of the FA-assay as one can ignore dissociation of the cofactor below the current, 16 nM dissociation constant.

In some embodiments, a protein engineering based strategy to covalently link the flavin or lumazine cofactor to the FA-sensor both in vivo and in vitro. This feature will allow one to significantly increase the sensitivity of the FA-assay as we can ignore dissociation of the cofactor In some embodiments, the amino acid sequence of a fLov2 protein (12 KDa) genetically encoded sensor for detection and imaging of protein complexes. The full length protein sequence for GeneID: O49003, the GenBank Accession and sequence hereby incorporated by reference, the nucleotide-binding flavoprotein NPH1-1 and also called LOV2 from *Avena sativa* (Oat) is provided herein and identified as SEQ ID NO: 1 (see. FIG. 11C). The nucleotide sequence (SEQ ID NO: 2) encoding the protein of SEQ ID NO: 1 is shown in FIG. 11D.

The nucleic acid sequence for the gene (NPH1-1) is provided in GenBank Accession No. AF033096.1 GI:2754822, *Avena sativa* non-phototropic hypocotyl 1 (NPH1-1) mRNA, complete cds, hereby incorporated by reference, and is identified herein as SEQ ID NO:2 (FIG. 11D).

In some embodiments, a truncated and mutated sensor protein derived from Lov2 that is 12 KDa or less, genetically encoded for detection and imaging of protein complexes. In various embodiments, the sensor protein has the sequence comprising SEQ ID NO: 3 (FIG. 11E). The highlighted portion shows the portion of the sequence have homology to the LOV2 protein. The underlined and bolded Cysteine is substitution for the wild type residue, Threonine.

In some embodiments, the sensor protein having the sequence of fLov2 (SEQ ID NO: 4)(FIG. 11F).

In some embodiments, a sensor protein having 50, 60, 70, 75, 80, 85, 90, 91, 92, 93, 94, 95, 96, 97, 98, 99 percent (%) homology to SEQ ID NOS: 3 or 4. In various embodiments, the sensor protein has at least a lifetime of or greater than 4.5 ns. In some embodiments, a sensor protein has 50, 60, 70, 75, 80, 85, 90, 91, 92, 93, 94, 95, 96, 97, 98, 99 percent (%) identity to SEQ ID NOS: 3 or 4.

In some embodiments, the amino acid sequence of a LUMP protein (12 KDa) genetically encoded sensor for detection and imaging of protein complexes. The full length protein sequence for UniProtKB/SwissProt Accession No. Q06877, the GenBank Accession No. CAA39879.1 GI:45570 and sequence hereby incorporated by reference. Lumazine is the antenna protein that modulates the color of the bioluminescence emission of the luciferase in *Photobacterium leiognathi*. In the presence of LUMP, luciferase emission is shifted to higher energy values (shorter wavelength). The LUMP protein sequence is provided herein and identified as SEQ ID NO: 6 (FIG. 11G).

In some embodiments, a sensor protein having 50, 60, 70, 75, 80, 85, 90, 91, 92, 93, 94, 95, 96, 97, 98, 99 percent (%) homology to SEQ ID NO: 6. In some embodiments, a sensor protein having 50, 60, 70, 75, 80, 85, 90, 91, 92, 93, 94, 95, 96, 97, 98, 99 percent (%) identity to SEQ ID NOS: 6. In various embodiments, the sensor protein having at least a lifetime of or greater than 4.5 ns.

The original gene is found in *Photobacterium leiognathi* subsp. *mandapamensis* luxC gene (partial) and lumP gene sequence provided in GenBank Accession No. X56534.1 GI:45568, which is hereby incorporated by reference and also provided herein as SEQ ID NO:7:

An original gene sequence for Y1 can be found in *Vibrio fisheri* subsp. The gene sequence provided in GenBank Accession No. M60852 GI: 155235, which is hereby incorporated by reference: LOCUS: VIBLUXY. The original gene for RiboflavinSynthase is found in *E. Coli* (K12). The gene sequence provided in GenBank Accession No. X69109 GI: 496323, which is hereby incorporated by reference LOCUS: X69109.

In some embodiments, a truncated sensor protein (mLUMP) derived from LUMP that is 10-12 KDa or less, genetically encoded for detection and imaging of protein complexes. In various embodiments, the sensor protein having the sequence comprising SEQ ID NO: 8 (in FIG. 11I).

In some embodiments, an isolated protein having 50, 60, 70, 75, 80, 85, 90, 91, 92, 93, 94, 95, 96, 97, 98, 99 percent (%) homology to full length LUMP (20 kD, SEQ ID NO:6). In some embodiments, an isolated protein having 50, 60, 70, 75, 80, 85, 90, 91, 92, 93, 94, 95, 96, 97, 98, 99 percent (%) identity to full length LUMP (20 kD, SEQ ID NO:6).

In some embodiment, a modified full length LUMP protein is provided, such as in SEQ ID NO: 9 (FIG. 11J).

In some embodiments, the isolated protein having 50, 60, 70, 75, 80, 85, 90, 91, 92, 93, 94, 95, 96, 97, 98, 99 percent (%) homology to mLUMP (10 kD, SEQ ID NO:8). In some embodiments, the isolated protein having 50, 60, 70, 75, 80, 85, 90, 91, 92, 93, 94, 95, 96, 97, 98, 99 percent (%) identity to mLUMP (10 kD, SEQ ID NO:8). In some embodiments, the isolated protein having 50, 60, 70, 75, 80, 85, 90, 91, 92, 93, 94, 95, 96, 97, 98, 99 percent (%) homology to full length LUMP (20 kD, SEQ ID NO:9). In some embodiments, the isolated protein having 50, 60, 70, 75, 80, 85, 90, 91, 92, 93, 94, 95, 96, 97, 98, 99 percent (%) identity to full length LUMP (20 kD, SEQ ID NO:9).

In some embodiment, any of the truncated LUMP and Lov2 derived fluorescent proteins genetically encoded in a vector for expression in a host organism for detection and imaging of protein complexes in the host organism.

In some embodiments, a peptide sequence that binds specifically to a target protein in a cell or sample can be appended to fLov2, Y1, LUMP and their truncated forms (at the N- or C-terminus) and used as an FA or FRET based sensor of the target protein. Thus, in some embodiments, genetically encoded LUMP or Lov2 sensors of specific proteins in a cell or sample.

In some embodiments, a peptide sequence that binds specifically to a target protein (or any targeting molecule more generally) in a cell or sample can be appended to fLov2, LUMP or Y1 and their truncated forms (at the N- or C-terminus) and used as an FA or FRET based sensor of the target protein. Thus, in some embodiments, genetically encoded LUMP or fLov2 sensors of specific proteins in a cell or sample are provided. In some embodiments, any of the fluorescent molecules provided herein can be combined with any targeting molecule. Similarly, in some embodiments, a nucleic acid sequence encoding for any of the fluorescent molecules provided herein combined with any amino acid based targeting molecule can be provided.

In some embodiments, by appending a peptide or full-protein tag (or any targeting molecule) onto the encoded protein it becomes possible to form a complex of the FA sensor with a larger protein target resulting in a large increase in the hydrodynamic volume and concomitant increase in the FA value. The change in the FA value can be used to quantify the amount of the target protein in the sample. It has been shown that a 12 kD fLov2 protein purified from *E coli* is highly fluorescent with absorption and emission properties similar to GFP, although the mass is 60% lower, the fluorescence lifetime is 200% longer and the FA value is <0.2 compared to 0.35 for GFP, the latter being very close to its limiting FA value of 0.4. Moreover, it has been shown that LUMP purified from *E coli* is a protein having absorption properties similar to CFP, emission properties similar to GFP, a mass of 20 kD, a fluorescence lifetime of 14 ns and an FA value of only 0.16.

In some embodiments, the system and methods can include performing a measurement and analysis of the value of the FA of the fluorescent Lov2 derivatives (e.g., fLov2, Y1, or LUMP probe fused to a peptide or protein tag that binds to a target protein (a "targeting molecule" binds to a "target protein"). In some embodiments, the targeting molecule can be amino acid based, and thus, can be expressed in a target cell or system by merely introducing a nucleic acid sequence, which encodes for the amino acid sequence (both the fluorescent molecule and the targeting molecule). In some embodiments, the targeting molecule can be a non-amino based molecule, as long as they bind to a desired target effectively and thereby allowed delivery of the fluorescent molecule to the desired location.

The interaction between the FA sensor (which can be the combined fluorescent molecule and the targeting molecule) and the target protein increases the value of the fluorescent anisotropy according to the increase in molecular volume that results following formation of the bound complex. The quantitative measure of the hydrodynamic property of the protein is the rotational correlation time, which scales with the molecular weight of a spherical protein such that the correlation time increases by 1 ns for every 2 kD of protein mass. For the 12 kD fLov2-fusion protein the FA value is ~0.2 and this increases upon binding to the target protein of mass 20 kD to a value as high as 0.35. In the case of a LUMP fusion protein, the FA value can increase from a value of ~0.16 in the unbound state to as high as 0.35 on binding to a target protein having mass of >20 kD. The analysis of protein complexes in samples based on FA measurements of the hydrodynamic volume of the genetically encoded probe and their complexes is not limited to measurements carried out in solution, in a multiwall plate reader, in a microfluidics device or within a microscope or cell sorter. The analysis may include FA measurements carried out using steady state methods or by using time-resolved FA measurements in the same sample environments. The analysis may include information from other fluorescence measurements or techniques not limited to FRET, fluorescence correlation spectroscopy, fluorescence lifetime imaging, determinations of quantum yield or the energy of the emission. These FA and hydrodynamic parameters may be used to discriminate between the free and bound forms of a protein in the sample. The said measurements may be made on a single probe or combination of FA sensors in the sample.

Generally, the mass of the protein cannot be reduced below a certain level without impairing the binding of the fluorescent cofactor. On the basis of structural analyses carried out of these proteins, one can estimate the limit for fLov2 will be 8 kD and 3.2 kD for LUMP.

In some embodiments the system and methods may include using the long fluorescence lifetime of the fLov2 and LUMP probes (or any of the fluorescent molecules provided herein) in FRET based measurements or imaging of protein interactions, not limited to the use of fusion proteins in which fLov2, Y1, or LUMP (or any of the fluorescent molecules provided herein) acts as the donor probe and YFP or other genetically encoded or dye labeled fluorescent or non-fluorescent protein or ligand serves as the acceptor probe in the FRET system. The longer lifetime of the probe serves to extend the Foerster transfer distance, which is of great practical significance in most types of genetically encoded FRET sensors.

In some embodiments, one can improve the measurement or imaging of protein complexes using the FA probes is to combine both FA measurements and fluorescence lifetime measurements in steady state or time-resolved mode using pulsed or modulated excitation.

In some embodiments, a method for measurement of proteins and their complexes in samples using the fLov2, Y1 and LUMP fluorescent proteins is provided by combining techniques not limited to fluorescence correlation spectroscopy, FRET, FA and FLIM. In some embodiments, a method for measurement of proteins and their complexes in samples using the fLov2, Y1 and LUMP fluorescent proteins is provide and includes combining techniques not limited to fluorescence correlation spectroscopy, FRET, FA and FLIM and as probes for super-resolution imaging microscopy including stimulated emission depletion (STED).

The fLov2 probe has a fluorescence lifetime that greatly exceeds that of other known genetically encoded proteins and may be lengthened further by carrying out mutations in the Lov2 protein. Such a property would increase the usefulness of the probe for measuring protein complexes using said methods and techniques. Another method to improve the properties of the fLov2 probe for measuring and imaging protein complexes using FA includes further truncation or reduction of the size of the Lov2 protein and its fusions with targeting peptides and proteins. The fLov2 probe has fluorescence lifetime that greatly exceeds that of other known genetically encoded proteins and may be lengthened further by carrying out mutations in the fLov2 protein. Such a property would increase the usefulness of the probe for measuring protein complexes using said methods and techniques. Another method to improve the properties of the fLov2 probe for measuring and imaging protein complexes using FA include further truncation or reduction of the size of the fLov2 protein and its fusions with targeting peptides and proteins.

Moreover, other variations to improve the properties of fLov2 for measuring and imaging protein complexes and as probes for imaging the distribution of tagged proteins in a sample include shifting the absorption and emission spectra to longer wavelengths and increasing the quantum yield of fluorescence emission through the action of introducing specific mutations in fLov2 and by using analogs of flavin mononucleotide added to the living cell, or else added to the purified protein.

The LUMP probe has fluorescence lifetime that greatly exceeds that of other known genetically encoded proteins and may be lengthened further by carrying out mutations in the LUMP protein. Such a property would increase the usefulness of the probe for measuring protein complexes using said methods and techniques Another method to improve the properties of the LUMP probe for measuring and imaging protein complexes using FA include further truncation or reduction of the size of the LUMP protein and its fusions with targeting peptides and proteins.

Moreover, other variations to improve the properties of LUMP for measuring and imaging protein complexes and as probes for imaging the distribution of tagged proteins in a sample include shifting the absorption and emission spectra to longer wavelengths and increasing the fluorescence quantum yield through the action of introducing specific mutations in LUMP and by using analogs of lumazine and ribityllumazine added to the living cell, or else added to the purified protein.

Other improvements to the targeting of fLov2 and LUMP proteins to specific proteins and complexes in a sample include carrying out mutagenesis on the tagging gene and using unconventional amino acid by using an expanded genetic code.

In some embodiments, the purified fLov2 fusion with a targeting peptide or protein may be used as a pre-formed stable complex with a purified target protein such that the FA value is close to the maximum value. When this complex is treated with a sample that may contain the target protein, such as a protein within serum, or other biological or environmental sample, then the binding will liberate the FA sensor from the complex and result in a low value of the FA. This can form the basis of a system for detecting the presence of drugs, diagnostic markers of disease, or other entity that binds to the fLov2 FA sensor.

In some embodiments, the purified fLov2 fusion with a targeting peptide or protein may be used as a pre-formed stable complex with a purified target protein labeled with a FRET acceptor probe such that the FRET efficiency between the fLov2 and the labeled acceptor protein or ligand is maximal. When this complex is treated with a sample that may contain the target protein, such as a protein within serum, or other biological or environmental sample, then the binding will liberate the FA sensor from the complex and result in a decrease in FRET efficiency. This can form the basis of a system for detecting the presence of drugs, diagnostic markers of disease, or other entity that binds to the fLov2 FA sensor.

In some embodiments, the purified LUMP fusion with a targeting peptide or protein may be used as a pre-formed stable complex with a purified target protein such that the FA value is close to the maximum value of 0.35. When this complex is treated with a sample that may contain the target protein, such as a protein within serum, or other biological or environmental sample, then the binding will liberate the FA sensor from the complex and result in a low value of the FA. This can form the basis of a system for detecting the presence of drugs, diagnostic markers of disease, or other entity that binds to the LUMP FA sensor.

In some embodiments, the purified LUMP fusion with a targeting peptide or protein may be used as a pre-formed stable complex with a purified target protein labeled with a FRET acceptor probe such that the FRET efficiency between the fLov2 and the labeled acceptor protein or ligand is maximal. When this complex is treated with a sample that may contain the target protein, such as a protein within serum, or other biological or environmental sample, then the binding will liberate the FA sensor from the complex and result in a decrease in FRET efficiency. This can form the basis of a system for detecting the presence of drugs, diagnostic markers of disease, or other entity that binds to the LUMP FA sensor.

In some embodiments, these measurements of FA and FRET may be made on any sample and in any instrument capable of measuring FA and FRET or both not limited to spectrophotometers, plate readers, cell phones, microscopes and microfluidics devices Some of the overall advantages, which is not intended to be limiting but merely illustrative, are described herein. In some embodiments, the present probes represent a new class of genetically encoded fluorescent protein that has unique properties of mass (volume) fluorescence lifetime and hydrodynamic properties to allow for accurate and *facile* measurements and imaging of proteins and their complexes within samples.

In some embodiments, the present probes provide quantitative measures of the FA, FRET efficiency and combinations thereof that can be used to study proteins and their complexes in vitro and in vivo and to detect the presence of specific molecules and proteins in samples.

In some embodiments, the present probes provide a system whose absorption spectrum, fluorescence emission spectrum, fluorescence lifetime, fluorescence quantum yield, FRET efficiency, FA value can be improved through mutation and truncation of the fLov2, Y1 and LUMP genes.

The applications of the methods discussed above are not limited to the diagnosis and/or treatment of protein complexes but may include any number of further diagnostic, measurement and analytical applications. Other proteins not limited to fLov2 (a fluorescent Lov2 derivative), Y1 (as in FIG. 11A), and LUMP or even non-protein molecules, endogenous fluorescent cofactors or exogenous fluorophores may be used to produce the fluorescent protein either within the cell or in vitro. The fluorescence from these proteins and their complexes, and measurements and imaging of these proteins may be carried out in any type of fixed or living cell, by transfection of cells with the gene encoding these proteins or by adding exogenous purified fluorescent protein to any sample in any environment including cells and tissue of live animal or human. Modification of the above-described methods and instruments for carrying out the invention, and variations of aspects of the invention that are obvious to those of skill in the art are intended to be within the scope of this disclosure.

The expression vector usable in the present methods with the presently described probes include pUC vectors (for example pUC118, pUC119), pBR vectors (for example pBR322), pBI vectors (for example pBI112, pBI221), pGA vectors (pGA492, pGAH), pNC (manufactured by Nissan Chemical Industries, Ltd.). In addition, virus vectors can also used including but not limited to lentiviral, adenoviral, retroviral or sendai viral vectors. The terminator gene to be ligated may include a 35S terminator gene and Nos terminator gene.

The expression system usable in a method with the presently described probes include any system utilizing RNA or DNA sequences. It can be used to transform transiently or stably in the selected host (bacteria, fungus, plant and animal cells). It includes any plasmid vectors, such as pUC, pBR, pBI, pGA, pNC derived vectors (for example pUC118, pBR322, pBI221 and pGAH). It also includes any viral DNA or RNA fragments derived from virus such as phage and retro-virus derived (TRBO, pEYK, LSNLsrc). Genes presented in the invention can be expressed by direct translation in case of RNA viral expression system, transcribed after in vivo recombination, downstream of promoter recognized by the host expression system (such as pLac, pVGB, pBAD, pPMA1, pGal4, pHXT7, pMet26, pCaMV-35S, pCMV, pSV40, pEM-7, pNos, pUBQ10, pDET3, or pRBCS) or downstream of a promoter present in the expression system (vector or linear DNA). Promoters can be from synthetic, viral, prokaryote and eukaryote origins.

The probes can be first cloned from cDNA, genomic DNA libraries, or isolated using amplification techniques with oligonucleotide primers, or synthesized. For example, sequences of candidate genes are typically isolated from nucleic acid (genomic or cDNA) libraries by hybridizing with a nucleic acid probe, the sequence of which can be derived from publicly available genomic sequence. In another embodiment, RNA and genomic DNA can be isolated from any mammal including: primates such as humans, monkeys, and chimpanzees; rodents, including mice and rats. Methods for making and screening cDNA libraries and genomic DNA libraries are well known (see, e.g., Gubler & Hoffman, Gene 25:263-269 (1983); Sambrook et al., supra; Ausubel et al., supra; Benton & Davis, Science 196:180-182 (1977); and Grunstein et al., *PNAS USA,* 72:3961-3965 (1975)).

Additional Alternative Embodiments

In some embodiments, the long fluorescence lifetime and the surface-bound fluorescent cofactor 6,7-dimethyl-8-(1'-dimethyl-ribityl) lumazine in LUMP are utilized in FRET probes that use Venus as an acceptor probe.

In some embodiments, the surface location of the ribityl-lumazine donor probe in LUMP provides an opportunity to increase FRET efficiency in fusions with a Venus acceptor probe compared with FRET efficiency in fusions using a CFP donor, where the fluorophore is buried in the protein matrix.

In some embodiments, the increase in the measured FRET efficiency of LUMP-Venus fusion proteins, the amino acid sequence of an embodiment of which is shown in FIG. 24 (SEQ ID NO: 16) compared with CFP-Venus arises, in part, from the close proximity of the donor probe on the surface of LUMP to the acceptor probe within Venus.

In some embodiments, although the longer fluorescence lifetime of ribityllumazine in LUMP-Venus fusion proteins does not affect the Förster distance, $R_0$, directly, it does affect FRET efficiency, because the rate of energy transfer is inversely related to the lifetime of the donor. Moreover, one might expect LUMP and Venus to undergo more extensive conformational dynamics during the 13.6-ns excited state lifetime [compared with CFP's 2.25-ns lifetime (Heidecker et al., Biochemistry 34(35):11017-11025 (1995)] that could favorably affect the orientation and proximity of their dipoles, and thereby increase FRET efficiency. FIG. 26 shows the peak-normalized absorption spectrum of Venus (right trace) superimposed on fluorescence emission spectrum of LUMP (left trace) in aqueous buffer [20 mM Hepes (pH 7.9), 150 mM NaCl] at 20° C. The shaded area indicates the overlap integral $J(\lambda)$ that is used to calculate the Förster radius $R_0$.

In some embodiments, the FA values of the free and target-bound states of a FA-sensor may differ by a factor of two. In some embodiments, the intermediate values in the range are proportional to the amount of bound target to the FA-sensor.

In some embodiments, the LUMP-Venus fusion is a zero-length LUMP-Venus fusion in which LUMP is linked to Venus by a zero-length (Ala-Ser) linker or Ala-Ser bridge. The amino acid sequence of an embodiment of zero-length LUMP-Venus fusion is shown in FIG. 24 (SEQ ID NO. 16).

In some embodiments, the efficiency of FRET in a zero-length LUMP-Venus fusion is 62% compared to ~31% in a related CFP-Venus fusion (van der Krogt et al., PLoS One 3(4):e1916 (2008)). In some embodiments, the FRET efficiency calculated in the LUMP-Venus fusion protein (0.62) is twofold higher than the FRET efficiency measured in an optimized zero-length CFP-Venus fusion protein (0.31) (van der Krogt et al., PLoS One 3(4):e1916 (2008)).

In some embodiments, the two fold difference in the fluorescence lifetime of LUMP in the FRET and no-FRET states of the thrombin sensor (further described in Example 15) also highlights the potential of using LUMP as a genetically encoded probe for FLIM and for FLIM-based imaging of FRET.

In some embodiments, the probe can be a LUMP-GBD probe. In some embodiments, the probe can be a Venus-LUMP probe. In some embodiments, the probe can be a Venus-thrombin-Lump probe. In some embodiments, a two part probe, having a cleavable linker between the two parts is provided. Cleaving the cleavable linker results in a change in anisotropy, allowing the presence or absence of a molecule to be detected based upon whether or not the molecule cleaves the cleavable linker. In some embodiments, the linker can be cleaved by Thrombin. In some embodiments, (the) other encoded linker sequences can be cleaved by matrix metalloproteinases (MMPs), digestive proteases including trypsin, chymotrypsin, carboxypeptidase, aspartartic proteases, cysteine proteases, subtilisin, proteases associated with of botulism, cathepsins, caspases, collagenases, elastases, proteases associated with blood disorders including plasmin, factor X, angiotensin converting enzyme (ACE) and HIV proteases. In some embodiments, a genetically encoded fluorescent protein is provided and/or optimised for fluorescent anisotropy measurements comprising at least one of LUMP, fLov2 or YY1 fused to a encoded protein domain that binds to a target protein or ligand, including, by way of example, nano bodies, (12.5 kD), diabodies (25 kD) and single chain antibodies (25 kD).

In some embodiments, FA can be easily and rapidly imaged with a fluorescence microscope, which allows for the dynamic and spatially (FIG. 2E) resolved observation of FA (Yan et al., Y Methods Enzymol 360:561-580 (2003); Dix et al., Biophys J 57(2):231-240 (1990); Mattheyses et al., Biophys J 87(4):2787-2797 (2004)) of LUMP-derived sensors in living cells.

In some embodiments, the large dynamic range of FA values between the free and bound states of LUMP sensors should also permit FA-based imaging of stepwise precomplexation reactions (Cao et al., Anal Chem 78(5):1478-1484 (2006)). For example, FA-based imaging can be used for detection of change in FA for a cascade of protein complexation events during a signaling cascade or regulation of gene expression.

In some embodiments, LUMP sensors can be used to quantify specific targets in living bacteria and, by extension, to investigate proteome-wide, high-throughput analyses of protein interactions. We note that it would not be possible to develop a related high-throughput approach using FRET, because each sensor would require separate optimization to generate an adequate change in FRET efficiency on binding to a specific target protein.

Example 1: Design of Genetically Encoded FA Sensors to Image Protein Complexes in Living Cells The present example studies developing flavoprotein[5]-based FA probes as hydrodynamic sensors for the activated form of Rac1, and its larger activated molecular complexes within motile cells. The studies can be initiated by creating a new fluorescent mutant of Lov2 (a fluorescent Lov2 derivative) developed that has a mass of 12 kD and fluorescence lifetime of 4.5 ns, >200% longer than GFP[6]. The FA value of free a fluorescent Lov2 derivative is <0.2, and can increase to the limiting anisotropy value on binding to a larger protein. Significantly, expression of a fluorescent Lov2 derivative fusion proteins in cells generates a strong and specific green fluorescence. An additional amino acid sequence (<5 kD) will be added to the C-terminus of the fluorescent Lov2 derivative to generate FA sensors that target the activated states of Rac1[7, 27]. This generates hydrodynamic sensors that bind to activated Rac1 with as large a difference in FA as possible, ideally from ~0.2 in the unbound state to ~0.35 in the activated Rac1 complex within a motile cell. The polarized (parallel and perpendicular) components of the emission of the FA probe will be recorded in real time by using an updated double-view FA imaging microscope[8]. This microscope will provide quasi real-time images of the absolute FA values of the fLov2-derived probe in the uncomplexed and in the GTP-bound Racicomplex[8], within a cell.

Finally, the design of genetically encoded FA probes will be extended to the blue-emitting lumazine binding protein (LUMP), which has the longest lifetime (14 ns) of any natural protein[9]. Analysis of the structure of LUMP[10] identifies a 10 kD domain (mLUMP) with blue fluorescence in transfected cells, and a strategy to reduce this class of FA probe to 3.2 kD (μLUMP). Importantly, the small mass and long lifetime of mLUMP allow for the design of FA probes fused to intact Rac1, (20 kD), or indeed any protein <35 kD. Design of Genetically-Encoded FA Based Sensors of Protein Hydrodynamics.

Figure 1A:
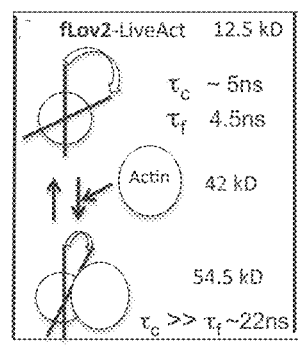
FIGS. 1A and 1B are a collection of schematic representations of the design of 3 genetically-encoded sensors for FA-based detection of proteins, using small GTPases as an example.
Figure 1B:
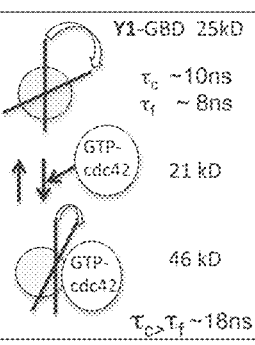
Figure 1C:
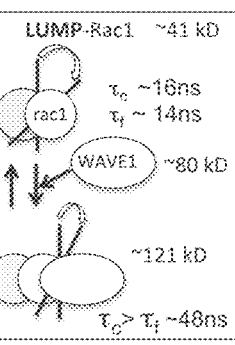
FIG. 1C depicts LUMP (20 kD) fused to 21 kD Rac1 as a FA sensor of Rac1-binding proteins such as WAVE1. The calculated $\tau_c$ will increase from ~16 ns to ~40 ns on binding to WAVE1 with concomitant increase in FA from ~0.2 to 0.35
Figure 1D:
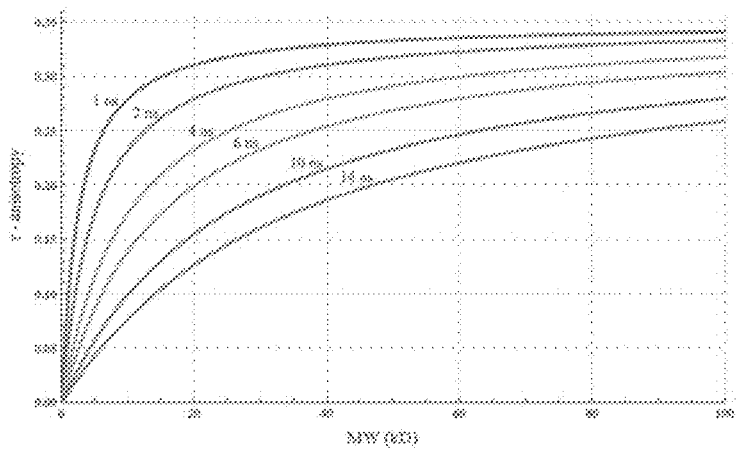
FIG. 1D, is a simulation of the Perrin-Weber equation showing how the anisotropy value scales with the molecular weight of a spherical protein assuming a spherical protein geometry: $r=1/r_0+\tau_f/(0.5\ MW)$, where the maximal anisotropy $r_0=0.35$, $\tau_f$ is the fluorescence lifetime, MW is the molecular weight, and 0.5 is a conversion factor that derives from the empirical relation that a 1 ns increase In the rotational correlation time $\tau_c$ results in an increase in molecular weight of 2.5 kD.

Gregorio Weber[1,2] showed that the FA value of a fluorescently labeled protein can be used to measure its hydrodynamic volume. If the protein associates with another molecule to form a larger complex, then the increase in hydrodynamic volume will correspondingly increase the FA value. The Perrin-Weber relationship between the FA value and the hyrodynamic properties of the protein are given by, $$r_o/r = (1+\tau_f/\tau_c) \text{ where } \tau_c = hV/RT$$

where $\tau_c$ is the rotational correlation time (time to rotate through 1 radian), $r_o$ is the limiting FA with maximum of 0.4, ie the value measured for completely fixed probe molecules, $\tau_f$ is the excited state fluorescence lifetime of the probe, h is the solvent viscosity and V is the volume of the protein. As a rule of thumb, for a sphere, $\tau_c$ will increase by 1 ns for every increase in mass of 2.5 kD. For a probe to exhibit sensitivity to changes in the hydrodynamics of its attached protein, $\tau_f$ should be similar to $\tau_c$. GFP is not useful as a probe of protein hydrodynamics as $\tau_f$ is ~2.5 ns, whereas the calculated $\tau_c$ is ~12 ns—correspondingly the FA value of GFP in aqueous solution at 20° C. is 0.325 with even higher values being found in GFP-fusion proteins that approach the 0.4 limit[6]. An ideal probe for sensing changes in the hydrodynamic properties, a labeled protein should exhibit a low FA in the unbound state, typified by a fluorescent protein with small mass and long fluorescence lifetime, while the FA value in the complex should be close to the limiting FA value. These principles are summarized for the interaction of an fLov2-LiveAct fusion protein with actin—in FIG. 1A, and for a Y1 fusion with the GBD in complex GTP-cdc42 in FIG. 1B and for a LUMP fusion with full length Rac1 in its complex with WAVE1 as shown in FIG. 1C. The general relationship between molecular weight and the anisotropy value of the probe is shown in a series of numerical simulations in FIG. 1D Optimizing Flavoproteins as Genetically Encoded Fluorescent Probes:

Flavoproteins have been used as genetically-encoded fluorescence probes[20] although their quantum yield ($\Phi_f$) and $\tau_f$ are generally low, while their mass is only modestly smaller than GFP. A new flavoprotein probe will be developed whose alloxazine group takes the form of flavin mononucleotide (FMN, riboflavin) or flavin adenine dinucleotide (FAD) and. A related fluorescent cofactor is ribityllumazine, an intermediate in the biosynthesis of the flavin group, which has one of the longest measured fluorescence lifetimes of any cofactor[21].

(a) fLov2: A Fluorescent LOV2 Derivative:

A fluorescent mutant of LOV2 is engineered as a genetically-engineered probe for FA detection and imaging of protein complexes in vitro and in living cells by increasing the fluorescence lifetime of the fluorescent sensor and by reducing the mass of the protein. A 21 kD non-switchable mutant of oat LOV2 (C450A), shown in FIG. 2A with a more detailed view of the riboflavin contact residues shown in FIG. 2B, was produced that emits a green fluorescence with a quantum yield ($\Phi_f$) of ~0.15. The quantum yield increases further by mutating T418C and replacing the J-α helix with a shorter 12 kD sequence to form "fLov2" a highly fluorescent LOV2 derivative).

Figure 2A:
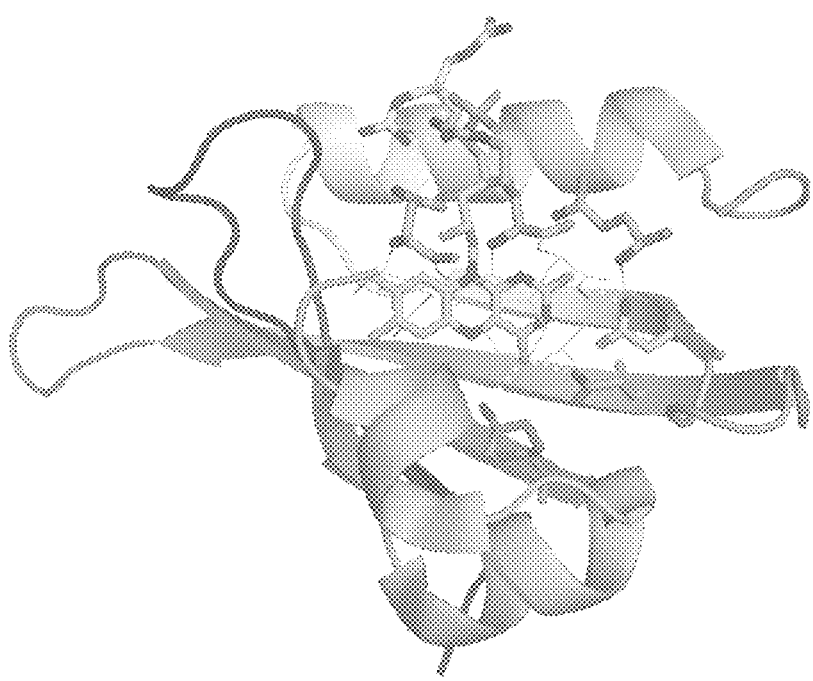
FIG. 2A depicts the atomic structure of a 12 kD fLov2 domain of LOV2.
Figure 2B:
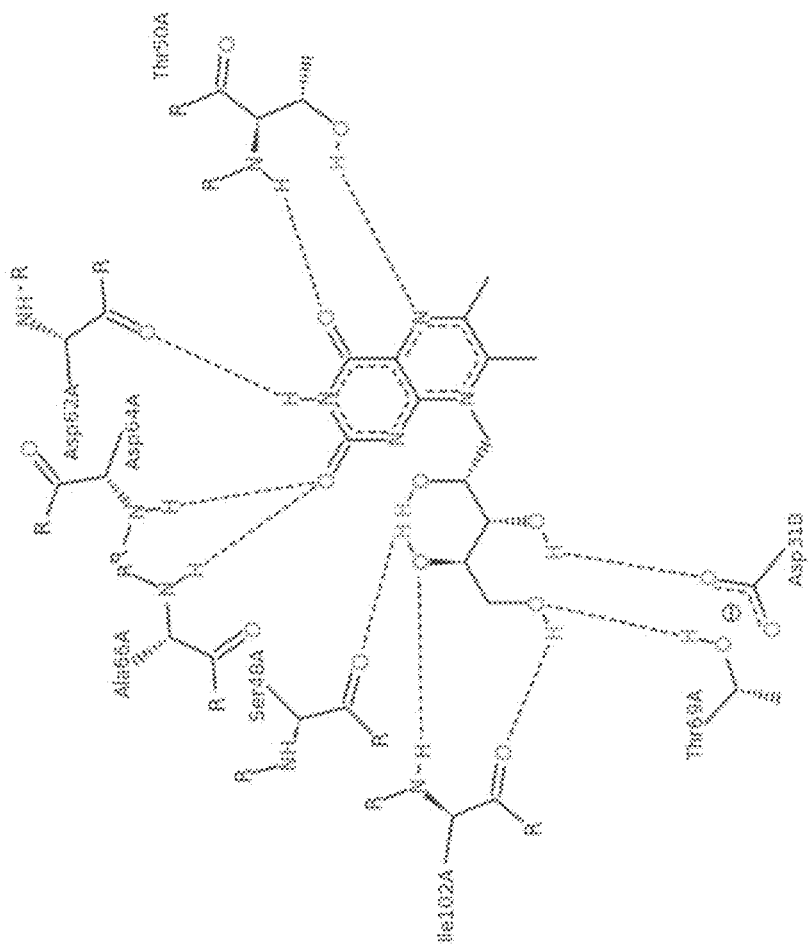
FIG. 2B, FMN contact residues in LOV2.
Figure 2C:
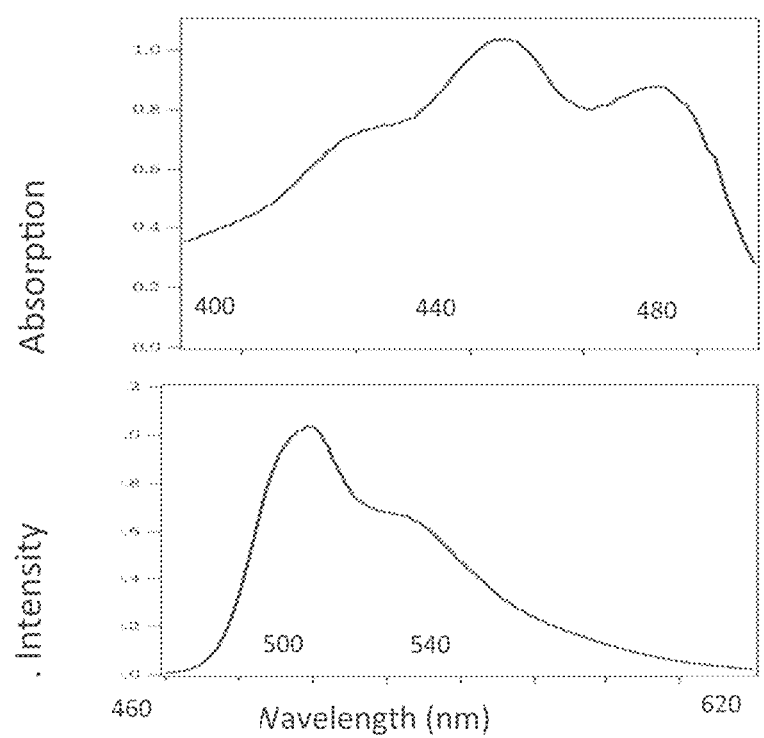
FIG. 2C, Absorption and emission spectra of a fluorescent Lov2 derivative in buffer at 20° C.
Figure 2D:
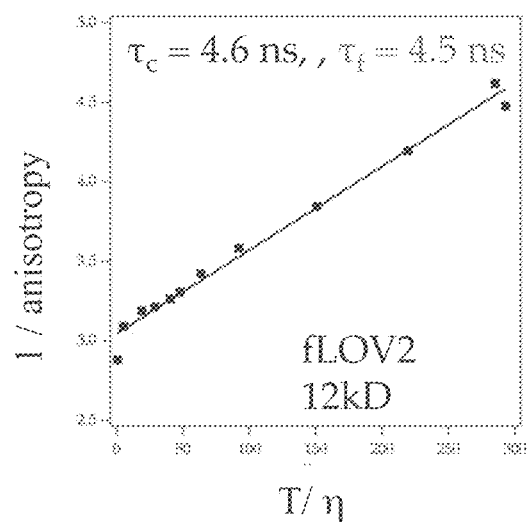
FIG. 2D, Weber-Perrin plot showing the hydrodynamic properties of a 10 kD fluorescent fLov2 derivative. The slope of the line has an exponent of ~1, strongly indicates the FA sensor is spherical.
Figure 2E:
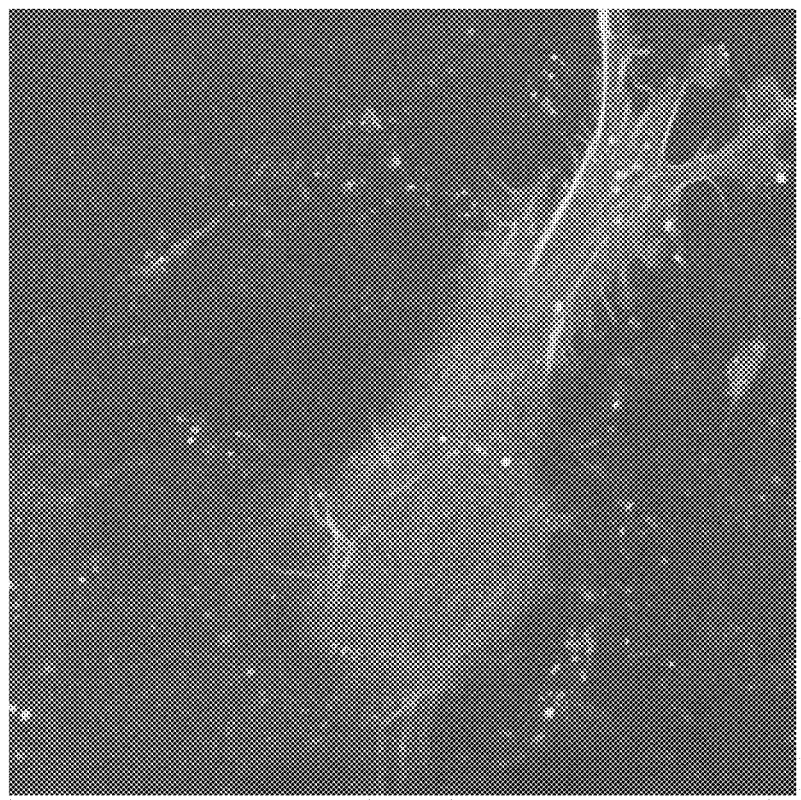
FIG. 2E shows the use of fLov2 as a small (12 kD) genetically encoded GFP-like probe. In the image fLov2 that is tagged to the F-actin binding peptide LifeAct and is shown to stain actin stress fibers in live cells.

In Vitro and In Vivo Fluorescence Properties of FA Sensors in Living Cells:

An extensive study of fluorescence and photophysical properties of an improved fluorescent Lov2 derivative called fLov2 was conducted and the properties were compared to CFP and GFP, the latter serving as a benchmark for the optimization of Lov2 for live cell imaging. The fLov2 detailed above functions as a genetically-encoded fluorescent probe, as can be seen in the absorption and emission spectra of the purified protein isolated from E coli (FIG. 2C). The Perrin-Weber plot for fLov2, where the reciprocal of the FA is plotted against the log of viscosity/Temperature (K) (FIG. 2D lower) shows that the probe has an exponent of ~1, indicating the protein is spherical. The fluorescence lifetime of fLov2 as determined from the Perrin-Weber plot is calculated at 4.5 ns while the intercept value of this plot shows that the longest wavelength absorption band has a limiting FA value of 0.35. Finally fLov2 is expressed in mammalian cells as shown in a fusion with the LiveAct peptide in FIG. 2E. These results suggest that intracellular fLov2 has a sufficiently high quantum yield to generate high contrast images of specific tagged proteins within living cells (FIG. 2E). The images shown in FIG. 2E are qualitatively comparable to those carried out using a GFP fusion protein with LiveAct.

Another significant finding of the fluorescence imaging study shown in FIG. 2E is that the fluorescence emission of the fusion protein shows little evidence of photo-bleaching under the illumination conditions (Zeiss 700 confocal microscope using the CFP excitation and GFP emission filters). This latter property will be further investigated to determine if the resistance results from exchange of riboflavin molecules in fLov2. If so, this property could prove very useful in the design of robust genetically encoded fluorescent proteins for in vivo imaging of targeted proteins. These in vitro and in vivo studies would also suggest that the quantum yield and lifetime of FMN in fLOV2 is higher than for free riboflavin[22].

Example 2: Optimization of the Physical and Photophysical Properties of LOV2-Derived FA Probes Fluorescent LOV2 mutants can be further optimized for FA imaging of Rac1-activation in cells by decreasing the mass or molecular volume of the fluorescent protein. A structure-guided strategy is used to achieve this goal that involves further truncation of the N- and C-termini of the 21 kD fLov2 to as low as 10 kD without overly compromising the binding and fluorescence emission and lifetime properties of riboflavin.

Example 3: Optimization of the Physical and Photophysical Properties of LUMP-Derived FA Probes LUMP is a 20 kD protein that binds tightly to ribityllumazine, a blue-emitting fluorescent cofactor and precursor of FMN that is distinct in having one of the longest excited state lifetime of any cofactors ($\tau_f$=15 ns)[21]. Lumazine is not present in mammalian cells[20], although preliminary results show cells transfected with LUMP and treated with a solution of pure ribityllumazine emit a blue fluorescence on exposure to 405 nm light. The calculated rotational correlation time of 20 kD LUMP at 8 ns is far shorter than the fluorescence lifetime (14-15 ns), and consequently the intact protein has a low FA value of <0.2. By reducing the mass of the LUMP protein even further, to as low as 10 kD, we will generate a new class of FA sensors that exhibit a very large change in FA values between their uncomplexed and complexed states (FIG. 1C). FA based imaging of Rac1 activation can be achieved using the favorable FA and in vivo imaging properties of LUMP and its truncated forms in vitro and in vivo (FIGS. 5, 6, 7, and 8 respectively).

Figure 3A:
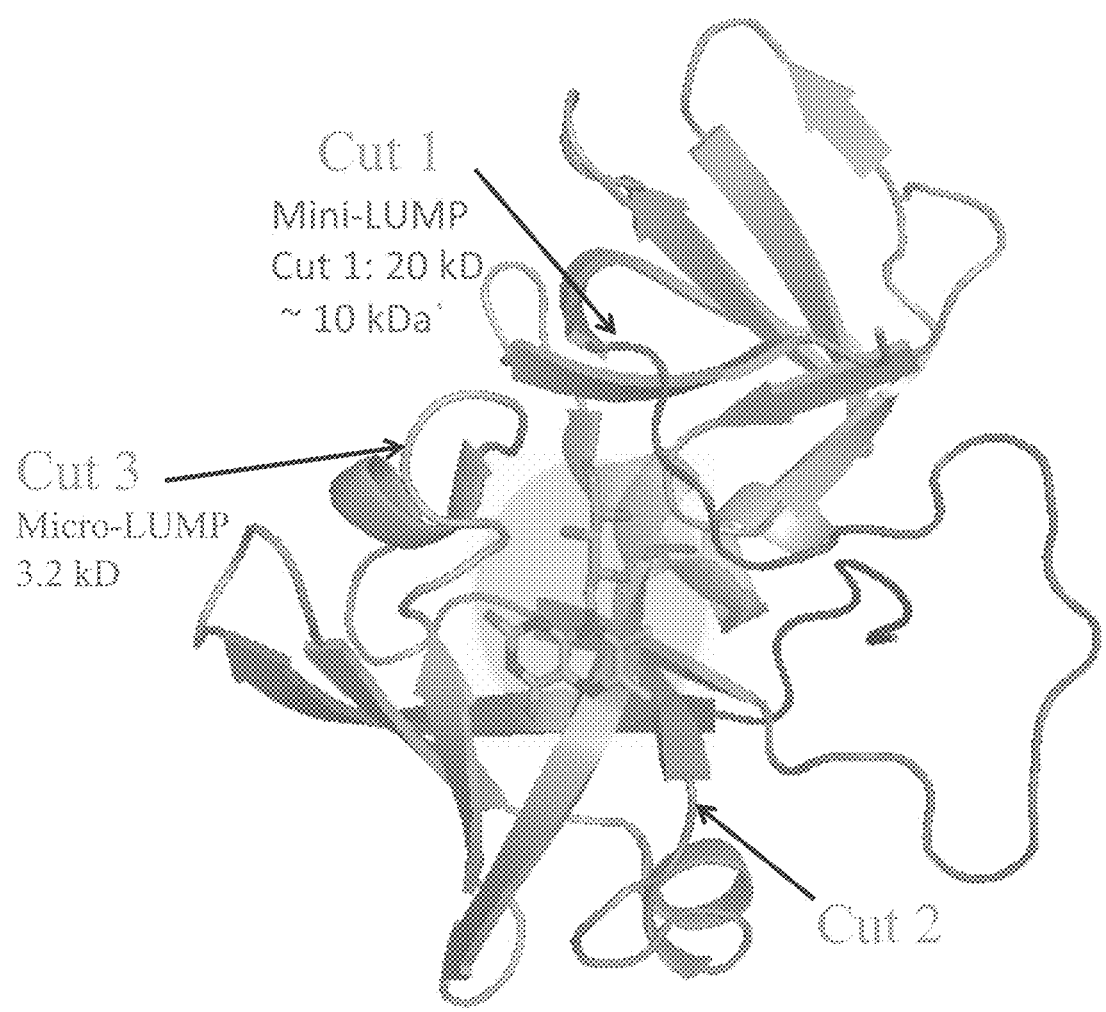
FIG. 3A, High-resolution structure of the 20 kD LUMP from P. leioghnati[10] showing the strategy to generate a 10 kD LUMP (mLUMP) and a 3.2 kD LUMP (μLUMP)

The structure of full length, 20 kD LUMP, (FIG. 3A), shows that the cofactor binds to an exposed pocket at the N-terminus of the protein with a $k_d$ of <16 nM[10]. Modeling studies of LUMP also suggests that the ribityllumazine binding site is completely contained within a 10 kD N-terminal domain of LUMP, which is referred to as mLUMP. mLUMP can be formed by truncating LUMP at the CUT1 site as indicated in FIG. 3A. The rotational correlation time for mLUMP fused to a 5 kD Rac1 binding sequence (Hr1b)

would still far lower, at 6 ns, and well below the 15 ns fluorescence decay time in its complex with GTP-bound rac1—thus the FA value for the uncomplexed probe will be <0.16 and should increase to ~0.25 in the complex with activated Rac1, and with an error in FA measurements of 0.001 the percentage of bound Rac1 can be easily and accurately determined. Moreover, it is possible to generate a 3.2 kD domain by further truncation at sites CUT2 and CUT3 (µLUMP, FIG. 3A) without removing any lumazine contact residues. The latter FA sensor would require ligating the ends formed by CUT1 and CUT3, (indicted in FIG. 3B), for which we will use systems proven to work for circular permutation of GFP[24]. The absorption, emission, quantum yield and lifetime of bound ribityllumazine in LUMP and its truncates will be monitored—we will carry out additional mutagenesis of residues bordering the lumazine group, shown in FIG. 3B, to maintain the binding and the long lifetime and high quantum yield of ribityllumazine emission.

The FA value for the uncomplexed µLUMP Rac1 sensor will less than 0.1, while the ~7-fold increase in mass on binding to full length Rac1 (21 kD) will increase the FA in the complex to ~0.2, and this should rise to 0.35 if the activated-rac1 sensor complex associates with larger signaling complexes. Finally the small size and long lifetime of the µLUMP FA sensor provides an opportunity to tag intact and full length Rac1 protein onto the FA probe, and as high quality sensor of Rac1 activation (FIG. 1C). Thus the ~25 kD µLUMP-Rac1 sensor has a calculated correlation time of ~10 ns ie much lower than the fluorescence lifetime of bound ribityllumazine such that the FA value of the free probe will be less than 0.2. The binding of the GTP-activated form of Rac1 to an effector protein such as WAVE1 will result in a further increase in the volume of the probe to the limiting value of 0.35.

These optimization of truncated LUMP probes as hydrodynamic sensors for target proteins such as Rac1, will be carried out as detailed for the fLov2. Encouragingly, HeLa cells transfected with a gene encoding mLUMP generates a cyan fluorescent protein as shown in FIG. 3C. Preliminary studies also show that mammalian cells transfected with LUMP and treated with pure ribityllumazine emit the same color emission. The absorption spectrum of LUMP extends to about 480 nm and has a broad emission that peaks at 460 nm and extends to 560 nm[9] as seen in FIG. 3C (Right). The possibility of shifting the absorption and emission bands of LUMP bound ribityllumazine to longer wavelengths will be explored as part of the mutational studies of the lumazine contact residues (FIG. 3B) as detailed above for fLov2. Whether synthetic ribityllumazine or lumazine derivatives added to cells can bind to LUMP and shift the fluorescence emission to longer wavelength can also be confirmed. Cells will be transfected with genes encoding the new FA probes and used with the FA-microscope (See Examples above) to image the distribution of the larger (higher FA value) GTP-bound Rac1 during a PDGF triggered motile response. Absolute values of FA for the free and Rac1 complexed states of the probes will be recorded by correcting for the high NA effect as described by Yan and Marriott (2003)

Example 4: Using Lov2 and LUMP Probes for Dynamic FA-Imaging of Activated Rac1 and its Complexes in Living Cell The molecular biology and cell biology techniques required for the manipulation of the hydrodynamic sensors and for fluorescence imaging of genetically encoded proteins and probes in living cells are described by Mao, S., Benninger, R K W., Piston, D., Jackson, Easley, C., D. Yan, Y. & Marriott, G. (2008). Optical lock-in detection of FRET using genetically encoded optical switches: High contrast FRET imaging of protein interactions in living cells. *Biophysical J.* 94, 4515-4524, hereby incorporated by reference in its entirety, with some being detailed in Example 1. Cell-based applications of these hydrodynamic sensors are designed to demonstrate proof of principle, and to show how localized activation of Rac1 correlates with the polymerization of actin and protrusion of the leading edge of motile cells. Correlative imaging of actin polymerization in transfected cells will be realized using a cell permeable TMR derivative of kabiramide C[14], which highlights barbed ends at sites of actin polymerization.

Integration of Targeting Groups for FA-Based Imaging of Activated Rac1.

The optimized genetically-encoded FA based sensors detailed herein will be targeted to image activated Rac1 during a motile response. The strategy detailed above however, is quite general and should be applicable to any protein interacting system where a target protein competes with a specific peptide appended on the FA probe can compete with the target protein. The best-studied example of this approach is employed in the imaging of activated Rac1, which binds tightly to a HR1b domain on the sensor[26]. In the current FA-based approach, the Rac1-binding sequence will be introduced through gene fusion to the C-terminus of the FA probe. Details for the design of the Rac1-targeting sequences appended to fluorescent Lov2 derivatives, LUMP, mLUMP and µLUMP were presented above and herein, and are also summarized in FIG. 1. In brief, a design criterion will be to maximize the difference in FA value of the probe between the unbound and activated Rac1. Thus, the targeting peptide should contribute less than 5 kD to the mass of the fluorescent Lo2 derivative and LUMP and mLUMP and still bind tightly to activated Rac1. Previous studies have identified rac1 targeting domains that fulfill both requirements[7,25]. With the 5 kD domain being more specific for Rac1, at least when integrated into FRET sensors, one can, as far as is possible, introduce these peptides/domains into our FA probes. If necessary slight modifications will be made in the linker and length of these peptides in order to maximize the change in FA value on binding to activated Rac1.

FA Sensors Fused to Intact Rac1:

As discussed herein, the remarkably long lifetime and small volume of mLUMP makes it possible to fuse proteins as large as 35 kD to the fluorophore and still generate a large change in the FA value on binding to the target protein. A demonstration of this property is significant for live cell imaging of Rac1 activation, as it allows the user to image the distribution of Rac1-complexes in the cell rather than imaging the distribution of activated Rac1 via competitive binding. Moreover, this technique provides an opportunity to extend the approach to image the distribution of the free and bound forms of any protein fused to mLUMP that has a mass less than 35 kD. Single fluorophore based FA probes of this type would extend the usefulness of CFP or GFP fusions of <35 kD by providing both a sensitive signal to image the distribution of both free and bound sensor and the means to resolve the free and bound states of the protein of interest.

Optimizing a Fluorescence Microscope for Real-Time, Recording of Absolute Values of FA.

The fluorescence microscope that will be used to record quasi-real-time images of the absolute value of FA for our probes in living cells is schematized in FIG. 10A. The original microscope and software for image registration, and calculation of absolute values of FA values on a pixel by pixel basis that are corrected for the high NA effect have already been developed by the Marriott group[8,15]. The dependence of the measured anisotropy value on the numerical aperture of the objective lens is shown in FIG. 10B.

One can update the double-view polarization microscope for simultaneous recording of the polarized components of the emission, and introduce an automated image registration function for the calculation of the raw and high NA (numerical aperture) corrected FA values from the two images and to calculate the corresponding state of the hydrodynamic sensor in the cell, i.e. unbound or target protein bound on a pixel by pixel basis. Correcting for the high NA effect is useful, as FA measurements carried out on a sample at low numerical aperture (NA) are higher than those measured with high NA objectives[13,8].

A calibration procedure can be implemented to correct for the high NA effect that measures the FA value in dilute solutions of TMR as a function of NA and viscosity[8] to calibrate high NA objectives for the high NA effect[8]. The high NA effect is objective dependent although the measured FA for a 1.4NA objective is typically lowered by about 12% compared to a low NA objective[8] as seen in FIG. 10B. This calibration procedure is easy to carry out and the correction can be integrated into software to generate absolute values of FA.

Example 5: Attaching Peptide Tags to fLov2 to Target Cellular Compartments

Peptide sequences, such as RGD, GGG and the myosin light chain kinase binding motif are attached to the fluorescent Lov2 protein to target it to various cellular compartments or protein targets.

For example, a 17 amino acid peptide (commercially called LifeAct™ available from Ibidi, LLC, Verona, Wis.) is linked to fLov2, Y1 or LUMP, which when expressed in living cells will bind to actin filaments, increasing their FA value and allowing one to generate high contrast images of these filaments in the cell.

Example 6: Using fLov2 Fusion Peptides to Bind and Capture a Diagnostic Target

An example of a simple FA-based assay would involve: first, purifying LUMP, Y1 or fLov2 or their truncated forms fused to an additional sequence that binds to a specific target protein with high affinity. Second, the FA value of this fusion protein is measured and, owing to its small volume and long lifetime, the FA value will be on the order of 0.2 or less. Third, the FA value is measured after adding an aliquot of the test sample, e.g. serum. If the serum contains the same target protein then it will bind to the FA-sensor, increasing the molecular volume and thereby increasing the FA value. The actual increase in the FA value is directly related to the amount of the target protein in the sample. Importantly these measurements can be made under no-wash conditions, which facilitates rapid and quantitative analysis of target proteins directly in serum, tears, sweat or other biological or environmental sample.

One can append (genetically) any peptide or full protein sequence to any of the fLov2, Y1, LUMP, or other probe disclosed herein. This additional sequence is used to capture the target protein in the sample. For example, one can make a fusion protein of LUMP with a sequence that binds to the alpha-fetoprotein, which can serve as a FA-based pregnancy test. These assays can also be conducting by supplying the user with a stoichiometric complex of the FA sensor and an antibody that binds to the targeting sequence where the FA value of this complex is close to the limiting value. If the authentic target is present in the sample then it will bind (more tightly) to the antibody and form the free FA sensor, which owing to its smaller mass will have a reduced FA value. In some embodiments, the antibody is a full length antibody. In some embodiments, the antibody is an antigen binding fragment, and need only include sufficient parts of the antibody (for example, 6 CDRs, or a heavy and light chain variable region domain) to bind to a target. In some embodiments, any of the cdc42 examples provided herein can be modified by replacement of the cdc42 molecule with an alternative binding fragment that can instead bind to a desired target. In some embodiments, the cdc42 molecule (or section thereof) can be replaced by an antibody or binding fragment thereof.

In a related FRET based assay format, a stoichiometric complex would be formed between any of the LUMP, Y1 or fLov2 fusion protein and a purified target peptide conjugated with a suitable FRET acceptor probe, such as fluorescein or eosin). The close proximity of the donor and acceptor probes will result in FRET and cause significant quenching of the fluorescence of the genetically encoded probe. If the authentic target protein in present in the sample, then it will displace by the labeled target and thereby reduce FRET efficiency, the latter serving as a sensitive measure of the target protein in a sample.

These FA and FRET based assays can be carried out using existing multiwall fluorescence plate-readers, or within the Abbott TdX polarization assay system.

Figure 10:
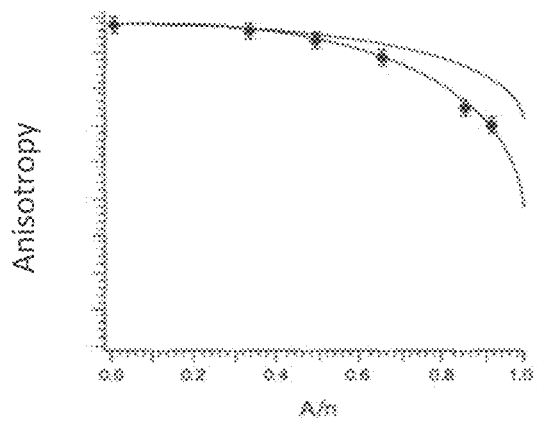

Example 7: Design of Genetically Encoded FA Sensors to Image Protein Complexes in Living Cells Flavoprotein[5]-based FA probes will be developed as hydrodynamic sensors for the activated form of rac1, and its larger activated molecular complexes within motile cells. These studies will be initiated by manipulating a new fluorescent mutant of Lov2 (fLov2) developed in the laboratory that has a mass of 12 kD and fluorescence lifetime of 4.5 ns, >200% longer than GFP[6]. The FA value of free fLov2 is <0.2, and can increase to a limit of 0.35 upon binding to a larger protein. Significantly, expression of fLov2 fusion proteins in cells generates a strong and specific green fluorescence. One can add an additional amino acid sequence (<5 kD) to the C-terminus of fLov2 to generate FA sensors that target the activated states of Rac1[7, 27]. Hydrodynamic sensors that bind to activated Rac1 are designed to exhibit as large a difference in FA as possible, ideally from <0.2 in the unbound state to ~0.35 in the activated rac1 complex with an error of +/−0.001 or ~025%). The polarized (parallel and perpendicular) components of the emission of the FA probe are be recorded in real time by using fluorescence spectrometer, microtiter plate, cell phone or microfluidic chip that is set up to record the polarized components of the emission of a sample. These measurements can also be made in a microscope equipped with double-view beam splitter[8] (FIG. 10) or a confocal microscope that can record polarization images either serially or simultaneously. This microscope shown in FIG. 10 generates quasi real-time images of the absolute FA values of a fLov2-derived probe in the uncomplexed and in the GTP-bound Rac1 complex[8], within a cell. Similarly one can extend the design of genetically encoded FA probes to the cyan-emitting LUMP, which has the longest lifetime (14 ns) of any natural protein[9]. Analysis of the structure of LUMP[10] identifies a 10 kD domain (mLUMP) with blue fluorescence in transfected cells, and a strategy to reduce this class of FA probe to 3.2 kD (µLUMP). Importantly, the small mass and long lifetime of full-length LUMP (20 kD) allow for the design of FA probes fused to intact rac1, (20 kD), or indeed any protein <20 kD and larger still for the truncated forms of LUMP.

Fluorescence Studies.

The fluorescence properties of purified LUMP and its fusion proteins were characterized by using an SLM-AB2 fluorometer as detailed in our earlier study (Marriott et al, 1988). The excitation anisotropy spectrum was recorded in buffer at 20 C. The emission wavelength was set at 470 nm and the excitation scanned from 380 to 450 nm according to Heidecker et al (1995). FA measurements were recorded on dilute and clarified protein solutions at 20 C in buffer at the indicated excitation and emission wavelengths (Marriott et al, 1988). The error in the determination of FA is 0.001 or a precision of 0.25%. The Perrin-Weber plot was carried out according to a standard method used in the Marriott lab. The viscosity of the sample was varied by adding defined volumes of sucrose from a stock solution. Viscosity values were taken from the handbook of Chemistry and Physics (94th Ed). The fluorescence lifetime of LUMP was calculated from the slope of the Perrin-Weber plot assuming a spherically shaped protein. The limiting FA value for LUMP is calculated from the reciprocal of the y-intercept. $\Phi_\square$ the fluorescence quantum yield of each fluorescent protein was determined according to the method detailed by Petchprayoon et al (2011). Specifically, the integrated emission intensity of an exact optical density of the flavoprotein was recorded and compared to an identical scan of the same optical density of fluorescein in 0.1 N NaOH.

Design of Genetically-Encoded FA Based Sensors of Protein Hydrodynamics.

The Perrin-Weber relationship between the FA value and the hydrodynamic properties of the protein are given by, $$r_o/r = (1+\tau_f/\tau_c) \text{ where } \tau_c = \eta V/RT$$

where $\tau_c$ is the rotational correlation time (time to rotate through 1 radian), $r_o$ is the limiting FA of 0.35 (for Flavin and lumazine), i.e., the value measured for completely fixed probe molecules, $\tau_f$ is the excited state fluorescence lifetime of the probe, $\tau$ is the solvent viscosity and V is the volume of the protein. As a rule of thumb, for a sphere, $\tau_c$ will increase by 1 ns for every increase in mass of 2.5 kD. For a probe to exhibit sensitivity to changes in the hydrodynamics of its attached protein, $\tau_f$ should be similar to $\tau_c$. GFP is not useful as a probe of protein hydrodynamics as $\tau_f$ is ~2.5 ns, whereas the calculated $\tau_c$ is ~11 ns—correspondingly the FA value of GFP in aqueous solution at 20° C. is 0.325 with even higher values being found in GFP-fusion proteins that approach the 0.4 limit for GFP[6] (FIG. 1B) An ideal probe for sensing changes in the hydrodynamic properties, a labeled protein should exhibit a low FA in the unbound state, typified by a fluorescent protein with small mass and long fluorescence lifetime, while the FA value in the complex should be ~0.4 (or 0.35 in the case of the flavoproteins). These principles are summarized for the interaction of an FA sensor e.g. fLov2 for the GTP-bound form of activated form of Rac1 shown in FIG. 4.

Optimizing Flavoproteins as Genetically Encoded Fluorescent Probes:

Flavoproteins have been employed as genetically-encoded fluorescence probes[20] although the quantum yield ($\Phi_f$) and $\tau_f$ of these probes are generally low, while their mass is only modestly smaller than GFP. The present example manipulates fluorescent flavoproteins that harbor alloxazine or lumazime cofactors that are produced entirely within the living cell after transfection with an appropriate expression vector. The new flavoproteins exhibit greatly improved fluorescence properties for FRET and fluorescence anisotropy based analyses of their distribution and interactions compared to their wild type form and other fluorescent proteins such as CFP. Lumazine for example, an intermediate in the biosynthesis of the flavin group, is distinct in having the longest measured fluorescence lifetimes of any cofactor (14-15 ns)[21], whereas fLov2 and Y1 have fluorescence lifetimes are at least twice that of GFP.

A fluorescent mutant of Lov2 (fLov2) is engineered as a probe for FA imaging of protein and other biomolecular complexes in living cells by increasing the fluorescence lifetime and by reducing the mass of the parent protein. In particular, initial efforts focused on a 21 kD non-switchable mutant of oat Lov2 (C450A), which emits a weak green fluorescence with a quantum yield ($\Phi_f$) of ~0.15. Truncation of the large C-terminal helix coupled with additional mutations identified in the DNA sequence for fLov2 (FIGS. 2A,B) increase the quantum yield of fLov2 to ~0.5. While purely exploratory in scope, the fact that our initial foray into the mutagenesis of oat Lov2 generates a flavoprotein with strong fluorescence is very encouraging, and suggests to us that increasing the lifetime and decreasing the mass of flavoproteins is not only feasible, but may result in <10 kD proteins with high quantum yield and fluorescence lifetime that exceeds 10 ns ie matching the fluorescence lifetime of the flavin in lactate oxidase (15 ns)[22].

In Vitro and In Vivo Fluorescence Properties of FA Sensors in Living Cells:

An extensive fluorescence and photophysical analysis of fLov2 was carried out and the results compared to CFP and GFP. fLov2 represents a new class of genetically-encoded fluorescent protein that is produced in high yield from E coli. The absorption (FIG. 2C top) and emission (FIG. 2C bottom) spectra of purified fLov2 show that the protein exhibits a broad absorption band compared to GFP and an emission that also extends further to the red compared to GFP. The Perrin plot (FIG. 2D) for fLov2, where the reciprocal of the FA is plotted against the log of viscosity ($\eta$)/Temperature (K) shows that fLov2 has as a spherical shape with an exponent of ~1, and has a calculated fluorescence lifetime of ~4.5 ns. The y-intercept value reveals a limiting FA value of 0.35. fLov2 and its fusion proteins are readily expressed in mammalian cells where they bind to free riboflavin and serve as genetically indicators of the C-terminal tagged sequence. fLov2 (10 kD) was appended with a 17 amino acid peptide that binds to F-actin (fLov2-LiveAct). These preliminary results suggest that intracellular fLOV2 fusion proteins emits with a sufficiently high quantum yield to generate high contrast images of the target protein in living cells (FIG. 2E). The image shown in FIG. 2E are qualitatively comparable to those carried out using a GFP fusion protein.

Another significant finding of the fluorescence imaging study shown in FIG. 2E is that the fluorescence emission from the fLov2 fusion protein shows little evidence of photo-bleaching under the standard confocal microscope illumination condition (Zeiss 700 using the CFP excitation and GFP emission filter set). This property is likely to result from the exchange of riboflavin molecules at the flavin-binding site of fLov2. This property would prove very useful in the design of robust genetically encoded fluorescent proteins, and is significantly different from that shown by GFP and related proteins that suffer from an irreversible photobleaching. Finally the high resolution and high contrast images of fLov2 fusion proteins obtained in living cells would suggest that the quantum yield and lifetime of riboflavin fluorescence bound to fLov2 is higher than measured for free riboflavin[22].

Example 8: Optimization of the Physical and Photophysical Properties of Lov2-Derived FA Probes A second design feature in our strategy to optimize Lov2 mutants for FA imaging of rac1-activation in cells, is to decrease the volume of the protein. Further truncation of the N- and C-termini of the 21 kD fluorescent Lov2 can be used without compromising the binding and fluorescence emission and lifetime properties of riboflavin. The feasibility of meeting this goal has recently been demonstrated by removing both the N-terminal residues 404-411 and residues 516-546, encompassing the C-terminal J-α-helix (FIG. 2A) produces a protein of 10 kD (fLov2) that exhibits strong fluorescence with $\tau_f$ of 4.5 ns. The Perrin plot shown for fLov2 (FIG. 2D) shows the protein is roughly spherical with the calculated $\tau_c$ of 4.5 ns closely matching the calculated value of 4 ns—moreover, the fluorescence lifetime of fLov2 is well-matched to the correlation time of fLov2 at 20 C at 1 cPoise. The FA properties of fLov2 will be further optimized by reducing its mass to 8 kD. This goal will be realized by excising loop regions in fLov2 (FIG. 2A). Compensatory mutations at the riboflavin binding site (FIG. 2B) will be introduced should the fluorescence lifetime decrease by an amount that compromises the FA measurement. fLov2 and its smaller variants should prove ideal sensors to quantify changes in the hydrodynamic properties of a fLov2 fusion proteins that bind to target proteins such as rac1 (FIGS. 1A,B). A genetically encoded FA sensor for Rac1 would compromise of the fLov2 core (10 kD) with an appended cdc42-targeting sequence of up to 5 kD, for example the GTPase binding protein (GBP). Using the Perrin-Weber equation we can show the fLov2-GBD sensor is ideal to quantify the presence of activated Rac1. For example, unbound fLov2-GBD is spherical (FIG. 4), and has a small molecular volume ($\tau_c$ of 6 ns) and long lifetime (4.5 ns) with a calculated steady state FA value of ~0.23, whereas its 35 kD complex with Rac1 would result in a $\tau_c$ of 14 ns and an FA value close to its limiting value. A larger dynamic range of FA could be realized for the same RAC1 target protein by using the 8 kD form of fLov2 and/or by increasing the fluorescence lifetime through specific mutations around the riboflavin binding site.

Fluorescence Lifetime of Riboflavin in fLov2:

fLov2 has one of the longest lived excited states of any genetically encoded fluorescent probe, and is more than 200% longer than CFP (2.4 ns)[6]. The longer fluorescence lifetime of fLov2 allows us to design FA probes for target proteins by appending specific amino acid sequences to the N- or C-termini of up to ~5 kD. This additional sequence will increase the FA value of fusion protein to ~0.23, compared to <0.2 for the core fLov2 (10 kD). The full dynamic range in FA values between the free and bound states of a fusion protein harboring a 5 kD tag is >0.15 FA units, which is sufficiently large to allow us to use FA values to titrate the binding of the sensor to its target protein in vitro and in vivo, as will be shown for LUMP-GBD binding to Rac1 (FIG. 4). The amino acid sequence of an embodiment of the LUMP-GBD fusion is shown in FIG. 23 (SEQ ID NO: 15). We will increase the dynamic range of FA based sensing of target proteins using fLov2 fusion proteins by identifying mutations that fall within 0.5 nm of the riboflavin binding site of fLov2 as depicted in FIG. 2B—we envisage extending the lifetime of riboflavin in fLov2 to 8 ns.[22]

Example 9: Optimization of the Physical and Photophysical Properties of LUMP-Derived FA Probes Methods of Protein Expression and Purification:

The gene of cdc42 was synthesized by Genewiz and cloned into the pSKB3 vector with a His-tag and TEV cleavage site. Site-directed mutagenesis (KAPA-HiFi Hotstart ReadyMix from KAPA Biosystems) was performed on the LUMP gene synthesized by Genewiz. Gene fusions of LUMP with GBD and Cdc42 were carried out by PCR amplification of gene inserts. Gene inserts GBD and Cdc42 were added using standard restriction and ligation enzyme techniques (New England Biolabs). The sequence of LUMP genes and its corresponding fusions were verified by sequencing.

Plasmids were transformed into *E. coli* BL21(DE3). Starter cultures (LB, 50 uM kanamycin) were inoculated from single colonies, grown at 37 C and used for 1:50 inoculation of 1 l cultures (TB, 50 uM kanamycin). Cultures were grown to OD of around 0.5, then cooled for 20 min at 16 C, induced with 0.5 mM IPTG, and grown overnight at 16 C. Cells were harvested by centrifugation for 15 min at 4,000 g at 4 C, and either washed with PBS and stored as a pellet at −80 C, or directly re-suspended in 20 ml lysis buffer (20 mM Tris, pH=8.0, 300 mM NaCl, 10 mM imidazole, half a tablet of "Complete Protease Inhibitor" (Roche), and 1 mM PMSF, and 2 mg lysozyme). After incubation for 20 min, the cells were lysed with an Avestin C3 homogenizer followed by 20 min centrifugation at 24,000 g. The supernatant was filtered through a 40 um Steriflip filter (Millipore) and loaded onto a 5 ml NiNTA column (Protino, Machery Nagel) after washing it with buffer A (20 mM Tris, pH=8, 300 mM NaCl). The column was washed with 30 ml washing buffer (20 mM Tris, pH=8, 300 mM NaCl, 25 mM imidazole) and eluted with elution buffer (20 mM Tris, pH=8, 300 mM NaCl, 250 mM imidazole). Imidazole was removed by exchanging against buffer A with a 10DG desalting column (BioRad) followed by overnight incubation at 4 C with 1/50 molar equivalents TEV protease to remove the N-terminal His-tag. The sample was incubated with 0.5 ml NiNTA agarose for 2 hours and the cleaved protein was eluted with 10 mM imidazole containing buffer A. After concentrating the protein with a centrifugal spin concentrator (Millipore) with a 30,000 D size exclusion limit, a final size exclusion chromatography run (Superdex 75 10/300 GL, GE Healthcare) with an Akta purifier against buffer B (20 mM Tris, 50 mM NaCl, pH=8) yielded proteins in typically >95% purity as characterized by SDS-PAGE and ESIMS. Purified proteins were stored on ice for up to 1 day or frozen in liquid nitrogen in small aliquots and stored at −80 C. Spectroscopic studies showed no change in the absorption or fluorescence properties of thawed proteins.

Figure 3B:
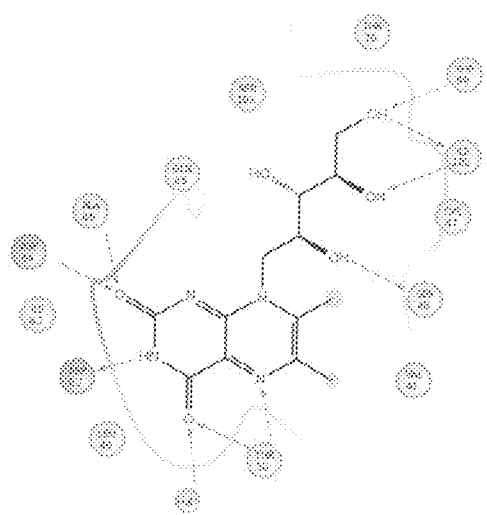
FIG. 3B, contact residues in full length LUMP (20 kD) that result in tight binding of ribityllumazine.
Figure 3C:
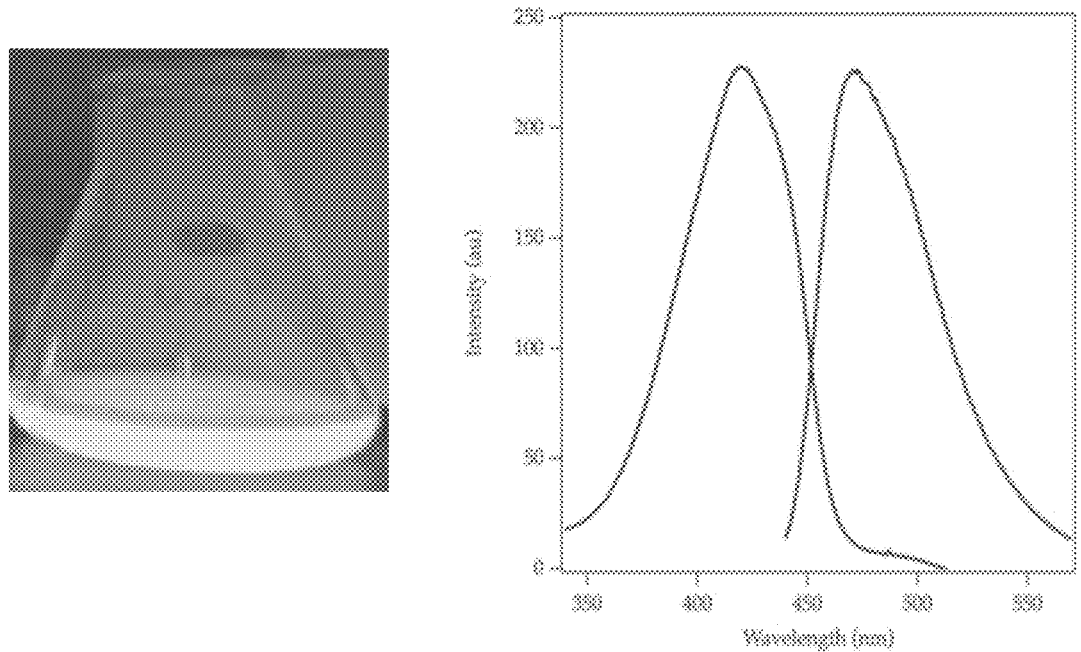
FIG. 3C Left panel shows an photograph of a 365 nm excited culture of E coli expression the gene encoding 20 kD LUMP. The right panel depicts the absorption and emmision spectrum of 20 kD LUMP in buffer at 20 degrees Centigrade, absorbance max. at 417 nm and emission maximum at 470 nm ($I_{ex}$=417 nm, measured in aqueous buffer solution (20 mM Tris, pH=8, 50 mM NaCl, peak-normalized).
Figure 3D:
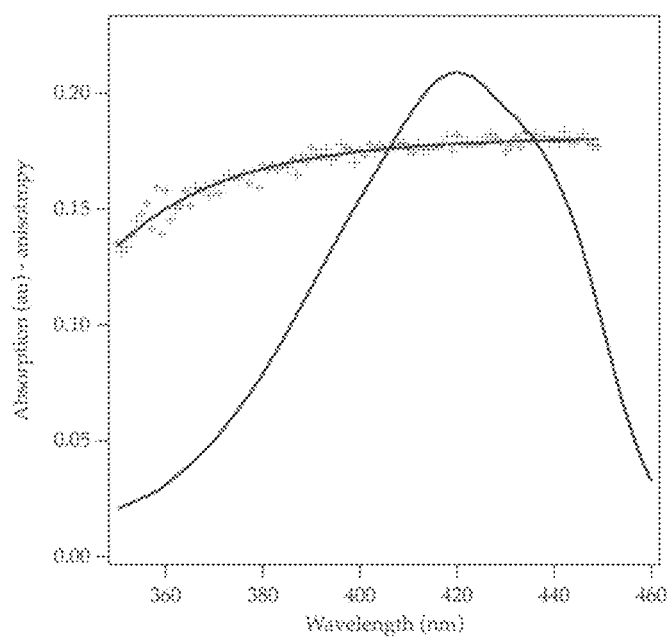
FIG. 3D depicts an absorption spectrum of LUMP (with fluorescence emission at 470 nm) and overlayed excitation anisotropy spectrum of 20 kD LUMP in buffer at 20 c (peak-normalized, measured in aqueous buffer solution, 20 mM Tris, pH=8, 50 mM NaCl).

LUMP is a 20 kD protein that binds tightly to ribityl-lumazine, a blue-emitting fluorescent cofactor and precursor of FMN (FIGS. 3A, 3B). LUMP has two structurally homologous domains (α and β) with the α-subunit noncovalently bound to lumazine with a dissociation constant (Kd) of 16 nM, constituting a roughly spherical hydrodynamic volume. Notably, lumazine is situated at the surface of the protein with the major proportion of the binding free energy deriving from hydrogen bonding interactions (FIG. 3B). The excitation and emission spectra of LUMP are similar to those of CFP as shown in FIG. 3C (Left and Right). LUMP is distinct from all other fluorescent proteins in having an exceedingly long excited state lifetime ($\tau_f$=15 ns)[21]. The calculated rotational correlation time of purified LUMP is 8 ns, which is far shorter than the 14-15 ns fluorescence lifetime, as shown in the excitation anisotropy spectrum (FIG. 3D) and the Perrin plot of FIG. 3E. The FA value of LUMP-GBD at 20 c in buffer is ~0.17 with a limiting FA value of 0.35 (FIGS. 3D,E). Thus LUMP exhibits a large dynamic range of FA value between the free and target protein bound forms.

The GTPase binding domain (GBD) from kinase ACK1 (residues 448-489) has previously been identified as a pseudo-CRIB domain that specifically binds to cdc42. The pseudo-CRIB domain of ACK1 is unique in that it binds selectively to cdc42 (Kd=15 nM) and not to rac1, which is the case for other related CRIB domain containing proteins. Adding the 43 amino acid peptide to the N-terminus of LUMP with a flexible 5 amino acid linker (SGSAS (SEQ ID NO: 30)) allows the newly designed GBD-LUMP to specifically target cdc42 in vitro as well as in E, coli (FIG. 3C). LUMP-Cdc42 is a fusion of protein of LUMP with the constitutively active GTPase Cdc42 (Q61L) connected at the C-terminal by a ten amino acid flexible linker (GSGKIISAGS (SEQ ID NO: 31)). In FIG. 5 it is shown that LUMP-Cdc42 displays an anisotropy of 0.19 that increases by 14% to 0.22 upon addition and binding to GST-tagged PAK1-PBD protein (Cytoskeleton Inc.). The Rac/Cdc42 (p21) binding domain (PBD) of the human p21 activated kinase 1 protein (PAK: residues 67-150) binds specifically to GTP-bound Rac and Cdc42 proteins with high affinity.

A purified LUMP-GBD fusion protein of 25 kD mass is used to titrate the activated form of cdc42 is shown in FIG. 11B. The binding of an additional 21 kD (cdc42) to LUMP-GBD (25 kD) increases the FA value from 0.17 to 0.21 for the free and cdc42 complexed forms of the sensor. Titration of cdc42 allowed the construction of a binding curve showing a high-level of binding as evidenced by quantitative binding and near saturation after addition of one equivalent of cdc42 relative to GBD-LUMP (FIG. 4). Live bacteria expressing LUMP display a strong cyan fluorescence emission when excited at 405 nm (FIG. 3C). The polarized components, parallel (FIG. 6A) and perpendicular (FIG. 6B), of LUMP-GBD emission are imaged within bacteria and in other bacteria co-expressing GBD as shown in FIGS. 6A and 6B. A pixel by pixel calculation of the FA value from these images is used to compute images of the FA values of LUMP-GBD and LUMP-GBD in complex with cdc42 within live E. coli as shown in FIG. 6C. The value of free LUMP-GBD at 0.22 is slightly higher than that measured for purified LUMP in solution (~0.17) and reflects the somewhat higher viscosity in the bacterium. Correspondingly the FA value increases in bacteria co-expressing LUMP-GBD and cdc42 (~0.25) as determined from FIG. 6C. LUMP can be optimized even further as a FA probe by carrying out a similar protein engineering strategy to that described for fLov2.

For example, LUMP can be reduced to 10 kD and even as low as 3.2 kD using the truncation strategies indicated below. We will carry out compensatory mutations in LUMP (FIG. 3B) to maintain the long fluorescence lifetime in these low molecular weight forms of LUMP. These truncated LUMP probes will exhibit a very large change in FA values between the un-complexed and target-complexed states of the fusion protein that are calculated to be 0.07 to 0.35 for the 10 kD LUMP probe.

The structure of full length, 20 kD LUMP from Phosphobacterium leioghnati (FIG. 12) shows that the cofactor binds to an exposed pocket at the N-terminus of the protein with a $k_d$ of 16 nM[10]. The studies suggest that the ribityl-lumazine binding site is confined to the 10 kD N-terminal domain of LUMP, (mLUMP). The calculated rotational correlation time for mLUMP fused to a 5 kD GBD binding sequence is still far lower, at 6 ns compared to the 15 ns fluorescence decay time—thus the FA values will increase from <0.10 to ~0.35 in cdc42 ternary complexes of >100 kD (FIG. 1C). Moreover, it is possible to generate a 3.2 kD domain (μLUMP, FIG. 3A) by excising mLUMP at the Cut 2 and 3 sites shown in FIG. 3A without eliminating lumazine contact residues. This truncation approach will also require ligating the ends formed by cut1 and cut3, (indicted in FIG. 3A), for which we will use systems proven to work for circular permutation of GFP[24]. The absorption, emission, quantum yield and lifetime of bound ribityllumazine can be monitored during the optimization of LUMP and carry out additional mutagenesis of residues bordering the lumazine group, shown in FIG. 3A, to maintain the binding and the long lifetime and high quantum yield of ribityllumazine emission. Finally the small size and long lifetime of the μLUMP FA sensor will provide an even larger dynamic range in FA compared to that shown for full length LUMP tag with full length Rac1 or cdc42, allowing it to serve as a high quality sensor for GTPase binding proteins such as WASP or WAVE (FIG. 1C). The ~25 kD FA sensor μLUMP-Rac1 has a calculated correlation time of ~10 ns ie well below the fluorescence lifetime of lumazine (15 ns) and so a large change in FA is expected between the free and bound forms of the Rac1 sensor.

The studies involved optimizing the fluorescence and protein targeting properties of LUMP, mLUMP as hydrodynamic sensors for target proteins, as detailed for LUMP-GBD. Encouragingly, HeLa cells transfected with a gene encoding LUMP in a medium of purified ribityl lumazine exhibit a blue fluorescence using 405 nm excitation. The absorption spectrum of LUMP displays a maximum absorbance at 417 nm with the red-edge extending to 460 nm. The absorbance spectrum extends to about 480 nm and has a broad emission that peaks at 460 nm and extends to 560 nm (FIG. 3C)[9]. The fluorescence anisotropy excitation spectrum of purified LUMP (20 kD) (FIG. 3D) shows the $S_0$-$S_1$ transition extending throughout the visible absorption band of the protein from 380-480 nm with a maximum FA value of 0.35. The limiting FA value does not reach the theoretical maximum, which indicates non-identical directions for the absorption and emission vectors in the molecule, a common occurrence for alloxaxine and lumazine fluorophores. The highest anisotropy value of 0.16 is recorded at greater than 400 nm.

The possibility of shifting the absorption and emission bands of lumazine to longer wavelengths will be examined as part of the mutational studies detailed above. Whether synthetic ribityllumazine or lumazine derivatives added to cells can bind to LUMP and shift the fluorescence emission to longer wavelength will be examined. Cells will be transfected with genes encoding the new FA probes and used with the FA-microscope (See Examples above) to image the distribution of the larger (higher FA value) GTP-bound rac1 during a PDGF triggered motile response. Absolute values of FA for the free and Rac1 complexed states of these probes will be recorded by correcting for the high NA effect.

The Y1 protein from Vibrio fisherei strain Y1 will be engineered as a red shifted genetically encoded probe for FA based detection of target proteins: Y1 shares sequence homology to riboflavin synthase, the high resolution structure[25] of which suggests that most of the C-terminal half of Y1 does not participate in the binding of riboflavin. We will be begin the modification of Y1 as an FA sensor by determining how much of the C-terminus can be removed without affecting the unusually long-lived and red-shifted riboflavin fluorescence. If necessary riboflavin-contact residues will be mutated within the ~10 kD truncated Y1 to compensate for loss of fluorescence or binding affinity. These studies will also allow one to further shift the excitation and emission spectra of Y1 and to extend $\tau_f$ beyond 8 ns. There is a reasonable chance of extending the lifetime.[6] The end-point for these studies is to generate an optimized Y1 core (10 kD with calculated $\tau_c$ of ~4 ns) with a $\tau_f$ of >8 ns—the calculated FA value of Y1 (10 kD) is 0.12, allowing us to append peptides and small proteins up to 12 kD to target specific proteins with the FA changing from 0.2 (free) to ~0.35 (bound) as schematized in FIG. 1B (FIG. 11A shows an embodiment of the amino acid sequence (SEQ ID NO: 12) and an embodiment of the nucleic acid sequences (SEQ ID NO: 13).

N-terminal Riboflavin synthase (N-RFS) is a dimeric protein that binds to one molecule of riboflavin and is schematized in FIG. 9. A novel monomeric form of N-RFS has been engineered by introducing two mutations (N72D/N83A) that disrupt inter-protomer contacts. The binding of riboflavin to the 8.8 kD mass of the N-RFS monomer will allow us to design add targeting sequences as large as 40 kD for FA based analysis of target proteins. The sequences of the native RFS (SEQ ID NO: 10) and variants (SEQ ID NO: 11) are provided in FIG. 11B.

Example 10: Using fLov2 and LUMP Probes for Dynamic FA-Imaging of Activated Rac1 and its Complexes in Living Cell Cell-based applications of these hydrodynamic sensors such as the LUMP-GBD are shown in FIGS. 6A-C and are designed to demonstrate proof of principle, and to show how measurements of FA can be used to quantify in vivo interactions between the FA sensor and its target protein. These in vivo microscope based FA imaging studies can be extended to FA sensing of target proteins using the fLov2 and Y1 probes and used accordingly.

Integration of Targeting Groups for FA-Based Imaging of Activated Rac1 and Cdc42.

The optimized genetically-encoded FA based sensors detailed herein will be targeted to image activated Rac1 and cdc42 in motile cells. The strategy detailed above however, is quite general and can be applicable to any protein interacting system where a target protein competes with a specific peptide appended on the FA probe can compete with the target protein. The best-studied example of this approach is employed in the imaging of activated cdc42, which binds tightly to the GBD domain appended to the N- or C-terminus of the sensor[26]. In the current FA-based approach, the sequence for the GBD is introduced through gene fusion to the C-terminus of LUMP (20 kD). Details for the design of other targeting sequences to fLov2, LUMP and Y1 were presented above.

In brief, the overriding design criterion will be to increase the difference in FA value of the probe between the unbound and bound form of the target protein. Thus, the targeting peptide should contribute less than 5 kD to the mass of fLov2 and Y1 or up to 20 kD to LUMP and its truncated forms and still bind tightly to target protein eg the activated Rac1 or cdc42. Previous studies have identified GBD as a capture group for cdc42 that fulfill both requirements[7,25]. With the 5 kD domain being more specific for cdc42, these peptides/domains will be introduced into the FA probes. If necessary slight modifications will be made to the linker and the length of these peptides in order to maximize the change in FA value on binding to activated GTPase.

Placing cdc42 at the N-terminus with the flexible nine amino acid linker (GSGKIISAGS (SEQ ID NO: 31)) provides an adequate spacer for native binding of cdc42 to PAK-PBD. Alternative fusion partners may require additional amino acids such as glycine and serine.

FA Sensors Fused to Intact Rac1:

As discussed herein, the remarkably long lifetime and small volume of LUMP and its truncated forms makes it possible to fuse proteins as large as 30 kD to the fluorophore and still generate a large change in the FA value on binding to the target protein. A demonstration of this property is significant for live cell imaging of effector proteins that bind to activated Rac1. The LUMP-Rac1 would allow the user to directly image the distribution of rac1 effector proteins in a cell. Moreover, this technique provides an opportunity to extend the approach to image the distribution of the free and bound forms of any targeted protein, DNA or biomolecule using a capture peptide or domain with mass of ~30 kD. These FA probes are also advantageous over CFP, YFP and GFP or their FRET fusions as the FA sensors are detected using a single probe whose FA value provides a quantitative measure of the free and bound states of the target protein in a sample or cell.

FRET Based Sensors:

The long fluorescence lifetime and small mass of LUMP, fLov2 and Y1 and their truncated forms make them powerful donor probes in FRET with a suitable acceptor probe and superior to those based on CFP-YFP. In particular, the longer lifetime, smaller mass and surface associated donor probe of fLov2, LUMP and Y1 allow the user to design FRET probes that exhibit a larger change in FRET efficiency owing to the closer proximity of the donor to the acceptor in one of the two states of the sensor (free or complexed) with a shorter distance that the $R_o$ (5 nm). This is a useful design feature as it is presently impossible to create CFP-YFP based FRET probes where the distance between the donor and acceptor is anything less than the $R_o$ value (5 nm) and most often the difference in FRET efficiency is only a few percent, especially for FRET based GTPase sensors. An example of this new class of FRET sensor is shown for LUMP-M13-Venus, whose FRET efficiency measured either by the change in the donor lifetime or quantum yield or the ratio of the LUMP: YFP sensitized emission is shown in FIG. 7. This particular probe was not optimized in any way that would further increase FRET efficiency for example by positioning the lumazine moiety closer to the venus acceptor, which would bring the two probes to even closer proximity in the calcium bound state. Truncated forms of LUMP would result in an even larger change in FRET efficiency to the YFP acceptor. fLov2 and Y1 could be used as donor probes to mcherry or mRuby further red shifted acceptor probes. Moreover even higher precision measurements of molecular proximity in these FRET sensors could be realized by combining the FRET based decrease in the donor signal with a concomitant increase in the FA value of the door—this method was first described by Heidecker et al, 1995.

In the example shown venus in the "cameleon" calcium ion sensor has been replaced with LUMP. This new FRET sensor shows a clear dependence on its donor signal (LUMP) and sensitized emission (from venus) as shown in FIG. 8 top graph. The ratio of the fluorescence signal of venus/LUMP is plotted against the free calcium concentration as shown in FIG. 8 bottom graph. Interestingly even without any optimization of the fusion protein, a FRET efficiency from the decrease of LUMP emission of almost 20% was measured. This improved FRET efficiency most likely results from the smaller size of LUMP (20 kD) versus CFP (28 kD), and exposure of the LUMP fluorophore to the surface of the protein, whereas in the case of CFP the fluorophore is buried in the middle of the protein and is further away from the acceptor.

Optimizing a Fluorescence Microscope for Real-Time, Recording of Absolute Values of FA:

The fluorescence microscope that will be used to record quasi-real-time images of the absolute value of FA for the probes in living cells can be that outlined above.

A second approach to FA imaging uses a laser scanning confocal microscope (Zeiss LSM 700) with a 20× low numerical aperture (NA) objective (Plan Apo) equipped with a pair of polarizers in the emission channel that are used to separately record images of the parallel and perpendicular components of the fluorescence emission. This system was used to record polarization images of LUMP shown in FIGS. 6A and 6B. The emission light was split into equally integrated parts by setting the variable beam splitter at λ=513-515 nm, each of which was directed through respective thin film polarizers in the emission filter wheel. Images S1 (S-polarized light, parallel) and S2 (P-polarized light, perpendicular) were recorded at two PMT detectors simultaneously and were used to construct the anisotropy image on a pixel-per-pixel basis according to the following equation: r=(S1−G×S2)/(S1+2×G×S2). Using standardized samples of fluorescein in varying amounts of water and sucrose, the G-factor, G, was determined to be 0.89.

In some embodiments, the small mass, long lifetime and surface location of the lumazine donor probe on LUMP is used to improve measurements of Foerster resonance energy transfer (FRET) efficiency using YFP as an acceptor probe compared to CFP. In particular, the smaller mass and the surface-exposed donor probe in LUMP can be used to improve FRET efficiency in LUMP fusions with YFP and to improve the dynamic range of FRET efficiency. Thus, in some embodiments, any one or more of the above noted LUMP options can be combined and/or paired with a YFP option for a probe pair for FRET and/or a method of performing FRET, involving LUMP as the donor and YFP as the acceptor. In some embodiments, the very long fluorescence lifetime (~15 ns) of LUMP coupled with its surface located donor and smaller volume compared to CFP make it a powerful acceptor probe in FRET with YFP.

The following outlines the methods and conditions for the following Examples. Q06877 of the Universal Protein Resource UniProt) was synthesized by Genewiz, Inc., with Nhe1 and Not1 restriction sites at the 5' and 3' ends and was subcloned into our pSKB3 vector that is based on Novagen's pET-28a vector but where the thrombin site is replaced by a tobacco etch virus (TEV) cleavage site. The gene insert GBD(ACK) was synthesized by Genewiz, Inc., with Nde1 and Nhe1 restriction sites at the 5' and 3' ends and was subcloned into a pSKB3 vector with a downstream Not1 restriction site. LUMP with Nhe1 and Not1 restriction sites at the 5' and 3' ends was PCR-amplified using forward and reverse primers (forward: 5'-AGC GCA GCT AGC TTT AGA GGT ATT GTT CAA GGT-3' (SEQ ID NO: 18) and reverse: 5'-GAG TGC GGC CGC CTA CCA TTC ATT TAA-3' (SEQ ID NO: 19)) and cloned into the GBD(ACK)-containing vector to make the GBDLUMP construct. All sequences were verified by primer-guided sequencing. GBD-LUMP was subcloned into the multiple cloning site 1 (MCS1) of the petDuet-1 vector (Novagen) with restriction sites Nco1 and HindIII using forward and reverse primers (forward: 5'-ATA TAT CC ATG GGC CTG AGC GCA CAG GAC-3' (SEQ ID NO: 20) and reverse: 5'-TAT TAT AAG CTT GAG TGC GGC CGC CTA CCA TTC-3' (SEQ ID NO: 21)). The gene of WT Cdc42 (*Homo sapiens*) was obtained from Addgene (plasmid 12201: pGEX-Cdc42) and PCR-amplified with NdeI and XhoI restriction sites using forward and reverse primers (forward: 5'-GCG CAT ATG CAG ACA ATT AAG TGT GTT GTT GTG GGC-3' (SEQ ID NO: 22) and reverse: 5'-TAT TAT CTC GAG TCA TAG CAG CAC ACA CCT-3' (SEQ ID NO: 23)) and subcloned into the pet-Duet-1 vector at MCS2. Finally, Cdc42 was mutated to its constitutively active form (Q61L) by site-directed mutagenesis using the KAPA HiFi HotStart ReadyMix PCR Kit (KAPA BioSystems) (forward primer: 5'-GAC TTT TTG GTA CTG CAG GGC TAG AGG ATT ATG ATA GAT TAC-3' (SEQ ID NO: 24) and reverse primer: 5'-GTA ATC TAT CAT AAT CCT CTA GCC CTG CAG TAC CAA AAA GTC-3' (SEQ ID NO: 25)). Protein Expression and Purification. Plasmids were transformed into *E. coli* BL21 (DE3). Starter cultures (lysogeny broth, 50 mg/L kanamycin) were inoculated from single colonies, grown at 37° C. and used for 1:50 inoculation of 1-L cultures (terrific broth, 50 mg/L kanamycin). Cultures were grown to an OD of around 0.5, cooled for 20 min at 16° C., induced with 0.5 mM isopropyl-β-D-thiogalactopyranoside, and grown overnight at 16° C. Cells were harvested by centrifugation for 15 min at 4,000×g at 4° C. and either washed with PBS and stored as a pellet at −80° C. or directly resuspended in 20 mL of lysis buffer [20 mM Hepes (pH 7.9); 300 mM NaCl; 10 mM imidazole; half of a tablet of Pierce Protease Inhibitor Tablet, EDTA-free (ThermoScientific); 1 mM PMSF; 2 mg of lysozyme]. After incubation for 20 min at 4° C., the cells were lysed with an Avestin C3 homogenizer, followed by 20 min of centrifugation at 24,000×g. The supernatant was filtered through a 40-μm Steriflip filter (Millipore), loaded onto a 5-mL Ni-NTA column (Protino; Machery Nagel), and washed with buffer A [20 mMHepes (pH 7.9), 300 mMNaCl]. The column was washed with 30 mL of washing buffer [20 mM Hepes (pH 7.9), 300 mM NaCl, 25 mM imidazole] and eluted with elution buffer [20 mM Hepes (pH 7.9), 300 mM NaCl, 250 mM imidazole]. Imidazole was removed by exchanging against buffer A with a 10DG desalting column (BioRad), followed by overnight incubation at 4° C. with 1:50 molar equivalents of TEV protease to remove the N-terminal His-tag. The sample was incubated with 0.5 mL of Ni-NTA agarose for 2 h, and the cleaved protein was eluted with 10 mM imidazole containing buffer A. After concentrating the protein with a centrifugal spin concentrator (Millipore), a final size exclusion chromatography run (Superdex 75 10/300 GL; GE Healthcare) with an Akta purifier against buffer B [20 mM Hepes, 150 mM NaCl, (pH 7.9)] yielded proteins of typically >95% purity, as characterized by SDS/PAGE and electrospray ionization (ESI) MS to validate the mass of all proteins, as well as the mass of the corresponding cofactor (ribityl-lumazine). MS measurements of proteins and cofactors were performed using a Thermo LTQ-Orbitrap-XL mass spectrometer equipped with an ESI source. Purified proteins were stored on ice for up to 1 d or frozen in liquid nitrogen in small aliquots and stored at −80° C. Spectroscopic studies showed no change in the absorption or fluorescence properties of thawed proteins.

Fluorescence Studies:

The fluorescence properties of purified LUMP and its fusion proteins were characterized by using an SLM-AB2 fluorometer (Aminco). The excitation anisotropy spectrum was recorded in buffer at 20° C. The emission wavelength was set at 470 nm, and the excitation was scanned from 380 to 450 nm. FA measurements were recorded on dilute and clarified protein solutions at 20° C. in buffer at the indicated excitation and emission wavelengths. The Perrin-Weber plot was carried out by recording anisotropies at varying sucrose concentrations with viscosity values taken from the CRC Handbook of Chemistry and Physics (94th Ed) (27). The fluorescence lifetime of LUMP was calculated from the slope of the Perrin-Weber plot assuming a spherically shaped protein. The limiting FA value for LUMP is calculated from the reciprocal of the y-intercept.

FA Imaging:

Zeiss LSM710. Images were recorded with a laser scanning confocal microscope (Zeiss LSM 710, inverse AxioObserver) with a plan-apochromat M27 with a magnification of 20× (N.A.=0.8) at room temperature. An anisotropy map was created on a pixel-by-pixel basis according to: r=(S1−G×S2)=(S1+2G×S2), where S1 and S2 are the P- and S-polarized images, respectively, and G is the G-factor that is determined by referencing the image anisotropy of LUMP to its known anisotropy (r=0.166) as measured on the SLM-AB2 fluorometer. The LSM710 confocal microscope is equipped with polarization accessories (Carl Zeiss Micro-Imaging GmbH).

Image Analysis:

Anisotropy images were calculated in Igor Pro (version 6.35, Wavemetrics) using a customized procedure that computes the anisotropy image (*_ani) from the S-image (*_S1) and P-image (*_S2) using a user-defined G-factor according to:

image_ani=(image_S1−G×image_S2)=(image_S1+2G× image_S2).

The procedure converts the bit image into a floating point image and does not set negative intensity values to zero. The following code can be copied into an Igor procedure file, compiled, and run from the command line with aniscalc= (name="image") while omitting "_S1" and "_S2" of the original file names, in which the output anisotropy image is appended with the ending "_ani":

pragma rtGlobals=3
include <Waves Average>
Function aniscalc([name])
string name
wave import_S1=$(name+"_S1")
wave import_S2=$(name+"_S2")
wavestats/Q import_S1
variable row=dimsize(import_S1, 0)
variable column=dimsize(import_S1, 1)
make/O/N=(row, column) $(name+"_ani")
wave ani=$(name+"_ani")
ani=(import_S1−0.78*import_S2)/(import_S1+0.78*2*import_S2)
End Anisotropy Simulation:

Anisotropy has been plotted as a function of molecular size with (i) τf, (ii) limiting anisotropy (r0), and (iii) a τc-to molecular weight (MW) conversion factor as parameters that can be varied interactively in the simulation. This calculation was performed in Mathematica (28) with the "Manipulate" function (Mathematica version 10.1, Wolfram Research). "Factor MW-to-τc" is the conversion factor that converts τc to MW based on a spherical tumbler by the relation: τc=factor×MW. The Mathematica code is shown below:

Manipulate[
Plot[(1/r0*(1+tf/(f*MW)))^−1, {MW, 0, 100},
Axes→{True, True},
AxesLabel→{MW−(kDa), r−Anisotropy},
LabelStyle→Directive[Black, Bold], GridLines→Automatic,
PlotStyle→Thickness[0.005], GridLinesStyle→Directive [Orange, Dashed],
PlotRange→{{0, 100}, {0, 0.36}}], {{r0, 0.36, "limiting anisotropy"},
0.3, 0.66}, {{tf, 4.5, "fluorescence lifetime"}, 0.1, 40},
{{f, 0.4, "factor MW→tc"}, 0, 1}]

Time-Resolved Fluorescence Measurements

All time-resolved measurements were made on a Leica TC SP2 inverted confocalmicroscope. The samples were excited by a Delta Diode 375-nm picosecond-pulsed laser (Horiba) operated at 8 MHz, and fluorescence was collected by an HPM 100-40 hybrid detector (Becker & Hickl). Fluorescence from the donor was selected by using a 455/70 bandpass filter (Chroma). Time-correlated single-photon counting was performed with an SPC-150 card (Becker & Hickl). Solutions of fluorescent proteins were imaged in a 385-well plate. The laser was scanned through an objective with a magnification of 20× (N.A.=0.5) onto the samples for 60 s to reconstitute single decays. The time-resolved fluorescence decays were imported into Origin software for background subtraction, normalization, and fitting. Duplicate curves for lifetime analysis were identical and were averaged to constitute single curves for each sample. A small irregularity in the decays was visible before the peak. This irregularity may be caused by filter fluorescence or reflection in the setup. This small predecay was disregarded in analysis and assumed to have negligible effect because its intensity was less than 1% of the fluorescence emission peak. Analysis of the residuals for monoexponential and biexponential decay models led to the choice of a biexponential fit:

$$It = y_0 + A_1 e^{-k_1 \tau_1} + A_2 e^{-k_2 \tau_2}.$$

Average fluorescence lifetimes (τavg) are calculated according to:

$$\tau_{avg} = f_1 \tau_1 + f_2 \tau_2, \text{ where}$$

$$f_1 = A_1 \tau_1 / (A_1 \tau_1 + A_2 \tau_2), \text{ and}$$

$$f_2 = A_2 \tau_2 / (A_1 \tau_1 + A_2 \tau_2).$$

Example 11: FA Properties of LUMP

FIG. 12 depicts the crystal structure of LUMP with surface bound ribityl-lumazine (Chatwell et al., *J Mol Biol* 382(1):44-55 (2008)). The FA excitation spectrum of purified LUMP (20 kDa) in a viscous medium [75% (mass/vol) sucrose] shows the $S_0$-$S_1$ transition extending from 380 to 480 nm, and reaching a maximum FA value of 0.350 as shown by the anisotropy scan of FIG. 14 and Perrin-Weber plot of FIG. 3E. The rotation of polarized emission at high sucrose levels has negligible effects on FA because of the short effective path length (1.67 mm) of the semimicrocuvette. The limiting FA value of LUMP of 0.360 is measured at an even higher viscosity (Lee et al., *Biochemistry* 24(6): 1476-1483 (1985). The theoretical maximum FA value of 0.400 is not attained, presumably because the absorption and emission dipoles in the ribityl-lumazine molecule are not colinear (Chatwell et al., *J Mol Biol* 382(1):44-55 (2008)).

Figure 3E:
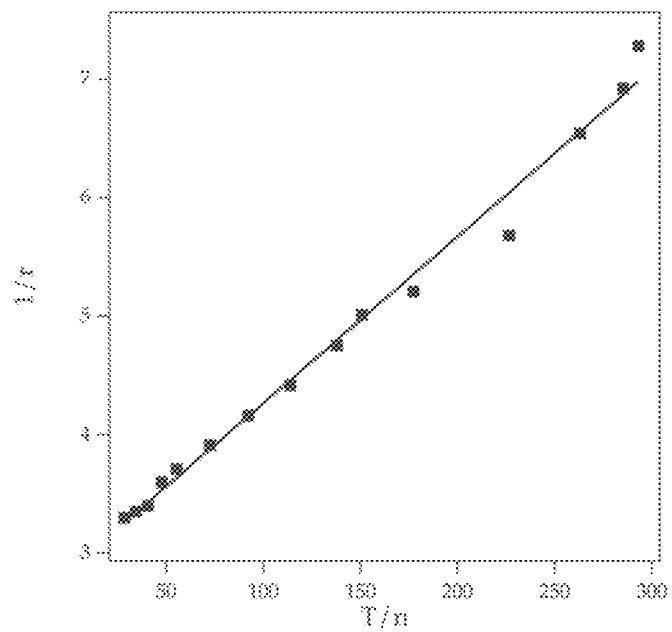
FIG. 3E shows the Perrin-Weber plot for purified 20 kD LUMP. Plot shows the inverse anisotropy (1/r) versus T/η where T=298 K and η is the viscosity in centiPoise (cP) in a water sucrose solution. The viscosities are obtained from the CRC Handbook of Chemistry and Physics. The curve depicts an unweighted least-squares fit to y=ax+b, where y=1/r and x=T/η. The fitting parameters are defined according to the Perrin-Weber equation.

The FA values of LUMP measured over a range of viscosities by adding incremental amounts of a concentrated sucrose solution are analyzed using the Perrin-Weber plot (FIG. 3E). A fluorescence lifetime for LUMP of 13.25 ns is calculated from the slope of the line (FIG. 3E), which is similar to the average lifetime of 13.6 ns measured by FLIM and shown by time-resolved fluorescence intensity decay of an embodiment of LUMP in FIG. 13 and TABLES 1 and 2. The expected FA value of a spherical 20-kDa LUMP molecule at 20° C. is computed as 0.133 [$\tau f$=13.6 ns, r0=0.360 (Lee et al., *Biochemistry* 24(6):1476-1483 (1985)], and assumes $\tau c$=8.0 ns, which is based on a 1-ns increase in $\tau c$ for every 2.5-kDa increase in mass. The experimentally determined FA value of LUMP is somewhat higher at 0.166±0.002 as determined from FIG. 14, which suggests that the protein is not strictly spherical.

Anisotropy Simulation:

Anisotropy was plotted as a function of molecular size with (i) $\tau f$, (ii) limiting anisotropy (r0), and (iii) a $\tau c$-to molecular weight (MW) conversion factor as parameters that can be varied interactively in the simulation. This calculation was performed in Mathematica (Wolfram Research (2015) Mathematica (Wolfram Research, Inc., Champaign, Ill.), Version 10.1.) with the "Manipulate" function (Mathematica version 10.1, Wolfram Research). "Factor MW-to-$\tau c$" is the conversion factor that converts $\tau c$ to MW based on a spherical tumbler by the relation: $\tau c$=factor× MW.

Time Resolved Fluorescence Measurements:

Time-resolved measurements were made on a Leica TC SP2 inverted confocal microscope. The samples were excited by a Delta Diode 375-ma picosecond-pulsed laser (Horiba) operated at 8 MHz, and fluorescence was collected by an HPM 100-40 hybrid detector (Becker & Hickl). Fluorescence from the donor was selected by using a 455/70 bandpass filter (Chroma). Time-correlated single-photon counting was performed with an SPC-150 card (Becker & Hickl). Solutions of fluorescent proteins were imaged in a 385-well plate. The laser was scanned through an objective with a magnification of 20× (N.A.=0.5) onto the samples for 60 s to reconstitute single decays. The time-resolved fluorescence decays were imported into Origin software for background subtraction, normalization, and fitting. Duplicate curves for lifetime analysis were identical and were averaged to constitute single curves for each sample. A small irregularity in the decays was visible before the peak. This irregularity may be caused by filter fluorescence or reflection in the setup. This small predecay was disregarded in analysis and assumed to have negligible effect because its intensity was less than 1% of the fluorescence emission peak. Analysis of the residuals for monoexponential and biexponential decay models led to the choice of a biexponential fit:

$$I_c = y_0 + A_1 e^{-k_1 \tau_1} + A_2 e^{-k_2 \tau_2}$$

Average fluorescence lifetimes ($\tau avg$) are calculated according to:

$\tau_{avg} = f_1 \tau_1 + f_2 \tau_2$, where $f_1 = A_1 \tau_1 / (A_1 \tau_1 + A_2 \tau_2)$, and $f_2 = A_2 \tau_2 / (A_1 \tau_1 + A_2 \tau_2)$.

TABLE 1

Fluorescence lifetime measurements-Pre-exponential factor A and fluorescence lifetime $\tau$ with standard errors are shown. The average fluorescence lifetimes were calculated from the two (parallel and perpendicular) fluorescent components.

| Protein | A1 | $\tau 1$ (ns) | A2 | $\tau 2$ (ns) |
|---|---|---|---|---|
| LUMP | 0.28 ± 0.011 | 6.3 ± 0.2 | 0.65 ± 0.01 | 14.91 ± 0.09 |
| LUMP-GBD | 0.37 ± 0.007 | 6.0 ± 0.1 | 0.55 ± 0.01 | 13.15 ± 0.06 |
| Venus-LUMP | 0.93 ± 0.002 | 4.17 ± 0.01 | 0.04 ± 0.002 | 12.9 ± 0.3 |

TABLE 2

Average fluorescence lifetimes ($\tau_{avg}$s)

| Protein | $\tau_{avg}$ (ns) |
|---|---|
| LUMP | 13.6 |
| LUMP-GBD | 11.5 |
| Venus-LUMP | 5.20 |
| Venus-thrombin-LUMP | 6.64 |

Example 12: FA-Based Protein Sensors of GTP-Bound Cdc42 Homolog—In Vitro FA Binding Study A LUMP FA sensor for GTP-bound cell division control protein 42 homolog (Cdc42) was generated by appending the 32-aa GTPase binding domain (GBD) from kinase human activated Cdc42 kinase 1 (ACK1; residues 448-489) (11) to the N terminus of LUMP via a flexible six-amino acid linker (GSGSAS (SEQ ID NO: 29)). An embodiment of LUMP and GBD-Cdc42 with the flexible six-amino acid linker GSGSAS (SEQ ID NO: 29) is shown in FIG. 15. LUMP-GBD (25 kDa) binds to Cdc42 specifically with a $K_d$ of 23 nM (Mott et al., *Nature* 399(6734):384-388 (1999)). This fusion protein was purified from *E. coli* and used for in vitro FA analysis of (GTP)-Cdc42 binding to GBD.

The FA value of unbound LUMP-GBD was 0.176±0.004, and increased to 0.207±0.002 ($\Delta$ of ~18%) when in a stoichiometric complex with GTP-bound Cdc42. These FA values were consistent with those FA values calculated using the Perrin-Weber equation for the free and Cdc42-bound states of LUMP-GBD. Thus, by using a $\tau f$ of 13.6 ns and a limiting FA of 0.360 for protein spheres of 25 kDa (cc of 10 ns) and 47 kDa (cc of 19 ns), the FA values were calculated as 0.155 and 0.212. These comparisons suggested that LUMP-GBD was not strictly spherical. The binding of a fixed concentration of LUMP-GBD to varying levels of GTP-bound Cdc42 was quantified by FA measurements, with saturation occurring at 1 equivalent of Cdc42 relative to GBD-LUMP (10 µM) as shown in FIG. 16. The increase in FA was shown to be GTP-dependent.

Example 13: Microscope-Based Imaging of the Polarized Fluorescence Emission of LUMP Microscope-based imaging of the polarized fluorescence emission of LUMP can be used to compute FA images that quantify the distribution of free and bound populations of the LUMP sensor in a sample.

A modified confocal fluorescence microscope was used to record real-time images of the steady-state polarized emission of His-tagged LUMP (23 kDa) bound to nitrilotriacetic acid (NTA)-functionalized agarose beads. The intensity image shows that most of the LUMP is localized to the outer surface of the bead, where, presumably, the bead has the highest level of NTA. FA images and distributions of FA values for LUMP in a sample containing 80 μm of NTA-agarose beads are shown in FIG. 17. Images were first registered, and the FA was calculated on a pixel-by-pixel basis by recording the polarized components of fluorescence emission of the probe in the free and the bound states. The FA values of His-tagged LUMP at the surface of the bead cluster around 0.310 (shown in FIG. 18 for the boxed region of FIG. 17), which is within 14% of the limiting FA value. This result suggests that LUMP molecules are almost completely immobilized when bound to NTA-agarose beads.

A corresponding FA image shown in FIG. 19A of His-tagged LUMP in solution with agarose beads lacking the NTA group is composed mostly of free LUMP with an FA value of 0.185. This value is similar to the value measured for His-tagged LUMP in buffer at 20° C. using a SLM-AB2 fluorometer (Aminco). This highlights an important benefit of using FA images to map the distributions of different molecular forms of the LUMP probe. In particular, because FA values are additive, the fraction of LUMP molecules that are free, or that interact transiently with the agarose bead in the FA image can be estimated. Thus, fractional contributions of each species to the total intensity can be calculated according to the relationship $r_{measured}=r_1 f_1 + r_2 f_2$, where r1 is the FA value of LUMP that is transiently immobilized of fractional intensity $f_1$, $r_2$ is the FA value of unbound LUMP within the bead of fractional intensity $f_2$, and $f_1+f_2=1$. This feature of FA imaging is useful because it can be used to quantify the fractions of two populations of the probe in a sample, whereas the intensity image would indicate the presence of a single and uniform population of LUMP molecules. FIG. 19B shows FA image obtained from P- and S-polarized images. In this particular study, the FA value of His-tagged LUMP outside the bead is 0.185 (box c in FIG. 19B), and inside the bead, the FA value is 0.215 (box d in FIG. 19B). The anisotropy distribution of box c is shown in FIG. 19C and the anisotropy distribution of box d in FIG. 19D. The latter value arises from a mixture of free LUMP (0.185) and LUMP molecules that bind transiently and nonspecifically to the bead (0.310), which represents an FA value that is obtained from a study of NTA-agarose beads. Using the relationships above, the percentages of free and transiently bound LUMP within agarose beads are calculated as 76% and 24%, respectively.

Example 14: FA-Based Protein Sensors of GTP-Bound Cdc42 Homolog—In Vivo FA Binding Study FA imaging of LUMP (20 kDa) was carried out in live bacteria. Confocal images of the polarized emission components (parallel and perpendicular as shown in FIGS. 20A and B, respectively) of LUMP fluorescence are used to calculate the FA value for every pixel in the image field. The images were obtained using a Zeiss LSM710 laser scanning confocal microscope adapted for real-time imaging of the polarized components of the emission (Methods). The images were acquired using a 20× (N.A.=0.8) objective so as to eliminate the high NA depolarization effect (Yan et al., *Methods Enzymol* 360:561-580 (2003)). The cerulean emission from untransfected bacteria is negligible compared with the cerulean emission from LUMP-transfected cells. Microscopy-derived values of FA are calibrated and validated by carrying out comparative measurements on the same solution of LUMP (20 kDa) with an SLM-AB2 fluorometer and the FA microscope. The FA value recorded for pure LUMP at 20° C. in a cuvette is 0.166±0.005, and in bacteria the FA was measured at 0.180±0.002.

Previous FA imaging and translational diffusion studies have shown that the microviscosity of the cytoplasm in living cells is approximately twofold to fivefold the microviscosity of water (Mastro et al., *Proc Natl Aced Sci USA* 81(11):3414-3418 (1984); Mao et al., *Biophys J* 94(11): 4515-4524 (2008)). The τc of LUMP will therefore increase by a small amount, resulting in a small increase in FA in cells as observed by *E. coli* FA imaging.

FA imaging was extended to quantify the hydrodynamic properties of LUMP-GBD (25 kDa) in living bacteria that coexpress constitutively active Cdc42 (Q61L; 20 kDa). Coexpression of GBD-LUMP and Cdc42 using the petDuet (EMD Millipore) double-expression vector results in equal amounts of the respective proteins in the cell, with concomitant formation of a 1:1 GBD-LUMP/Cdc42 complex. The FA value of LUMP-GBD in *E. coli* is 0.233±0.004, as determined from the anisotropy image in FIG. 20C and the anisotropy distribution in FIG. 20D, which is consistent with the formation of the 45-kDa heterodimeric (LUMP-GBD/Cdc42) complex. The FA value for the complex recorded in live bacteria was again slightly higher than in solution, indicating that the probe experiences a modestly higher viscosity compared with the viscosity measured at 1 cP in buffer at 20° C. (0.207±0.002).

Example 15: Kinetic Study of Venus-Thrombin-LUMP

The improvement in FRET efficiency in protein fusions of LUMP with Venus was exploited in the design of LUMP-derived FRET-based sensors that exhibited a large change in FRET between their intact and dissociated forms. In particular, a genetically encoded FRET-based thrombin sensor was introduced that was composed of LUMP, which was fused to Venus via an 11-residue linker that harbors a thrombin cleavage site (AS<u>LVPR</u>//GSRGS, where the proteolysis site is denoted by the symbol //, and the underlined residues represent the thrombin recognition sequence) (Takagi et al., Biochemistry 13(4):750-756 (1974). FIG. 21A shows a comparison of the FRET efficiency of minimum linker Venus-LUMP (top dot) and Venus-thrombin-LUMP (bottom dot) FRET probes relative to the $R_0$ of 5.2 nm. The amino acid sequence of an embodiment of Venus-thrombin-LUMP is shown in FIG. 25 (SEQ ID NO: 17).

The efficiency of FRET in this substrate of 51% was calculated from the ratio of the integrated fluorescence intensities of LUMP in the intact and cleaved substrates. The corresponding average distance between the donor and acceptor dipoles in the substrate was 5.2 nm. The change in the emission spectrum of the FRET substrate during proteolysis by thrombin was marked by a large increase in LUMP emission and a dramatic decrease in the sensitized emission of Venus, with the donor/acceptor ratio increasing ~4.7-fold as shown in FIG. 21C. The activity of thrombin activity may also be measured using the large change in FA values of LUMP in the intact and proteolyzed forms of the substrate as shown in FIG. 21D. Using a fluorescence lifetime of 13.6 ns for purified LUMP derived from the intensity decay (shown in FIG. 21B), and a ratio of LUMP emission in the no-FRET and FRET states of the thrombin substrate of 2.6, a calculated fluorescence lifetime for the intact substrate of 6.6 ns was determined, which is close to the 5.5-ns lifetime computed from the decay of the donor emission shown in FIG. 21B).

These lifetime data were used in the Perrin-Weber equation to calculate FA values for the 51-kDa LUMP-Venus substrate of 0.255±0.003, which assumes that the molecule is spherical with τc of 20 ns and decreases to 0.166±0.001 in the proteolyzed sensor as shown in FIG. 21D. Thus, as highlighted in an earlier study (Heidecker et al., *Biochemistry* 34(35):11017-11025 (1995)), the FA value of the donor probe can also be used to quantify the reaction.

Example 16: Kinetic Study of mRuby-Thrombin-fLov2

The improvement in the FRET efficiency for fLov2 fusions with mRuby was exploited in the design of fLov2-derived FRET-based sensors that exhibited a large change in FRET between their intact and dissociated forms. In particular, a genetically encoded FRET-based thrombin sensor was introduced that was composed of fLov2, which was fused to mRuby via an 11-residue linker that harbors a thrombin cleavage site (ASLVPR//GSRGS, where the proteolysis site is denoted by the symbol // (Takagi et al., Biochemistry 13(4):750-756 (1974).

The efficiency of FRET in this substrate of ~43% was calculated from the ratio of the integrated fluorescence intensities of fLov2 in the intact and cleaved substrates. The change in the emission spectrum of the FRET substrate during proteolysis by thrombin was marked by a large increase in fLov2 emission and a dramatic decrease in the sensitized emission of mRuby, which is shown in FIG. 27A.

This result demonstrated the development of a high FRET efficiency genetically encoded substrate for thrombin using fLov2 as a donor probe and mRuby as the acceptor. The fusion protein was identical to that described in FIG. 25 with the exception that fLov2 replaces LUMP and mRuby replaces Venus. As shown in FIG. 27A, the emission spectra were recorded as a function of time after the addition of thrombin. The spectra showed the dramatic increase in fLov2 fluorescence and attenuation of the sensitized mRuby fluorescence as a result of the thrombin mediated cleavage and separation of the donor and acceptor probes.

The activity of thrombin activity was also measured using the large change in FA values of LUMP in the intact and proteolyzed forms of the substrate in the green (fLov2) and red (mRuby) region s of the emission spectrum, as shown in FIG. 27B. The FA value in the fLov2 region of the spectrum was higher in the intact substrate than the cleaved substrate because the lifetime is shorter owing to FRET to the mRuby and the larger volume of the fusion protein. In the cleavage substrate the fLov2 is now only 10 kD and because of the relief of FRET it has a longer lifetime (4.5 ns). The combination of smaller volume and longer mass of the cleaved substrate decreased the FA value in the fLov2 region of the spectrum. The FA value in the mRuby region of the spectrum was almost zero in the intact substrate and rises after cleavage. The former is characteristic of FRET and arises because the dipoles of the donor probe, which is directly excited with polarized light, and the acceptor probe which is excited due to FRET from the FMN probe are not co-linear and there is an increase in the geometrical distribution between the dipoles as a result of the flexible linker. These effects are removed in the proteolysed substrate—the FA value in the mRuby region now reflects that from the direct excitation of the relatively fixed dipole in mRuby probe. The full amino acid sequence of the thrombin substrate (including a His-tag) used in this example is shown in FIG. 27C. The amino acid sequence of the fragment bearing mRuby2 after cleavage with thrombin is shown in FIG. 27D. The amino acid sequence bearing fLov2 after cleavage with thrombin is shown in FIG. 27E.

Example 17

Measurements of FRET efficiency in a fusion protein composed of fLov2, the coil region of the spider protein and mRuby within living HEK293 cells are shown in FIGS. 28A and 28B. The FRET efficiency in the fusion protein is calculated by recording the fLov2 fluorescence signal averaged in a number of cells before (FIG. 28A) and after (FIG. 28B) the bleaching of the mRuby probe using 555 nm irradiation. The bleaching of the acceptor probe resulted in a loss of FRET efficiency which is reflected in the increase in the fLov2 signal in the same cells (FIG. 28B). The FRET efficiency between fLov2 and mRuby in the fusion proteins is measured at 44.7%. This value is considerably higher than that possible using CFP-YFP fusion proteins, and is a consequence of the small volume of fLov2 compared to CFP, the surface exposed FMN donor probe in fLov2 and the longer lifetime of FMN (4.5 ns) compared to 2.25 ns for CFP.

Image Analysis:

Anisotropy images were calculated in Igor Pro (version 6.35, Wavemetrics) using a customized procedure that computes the anisotropy image (*_ani) from the S-image (*_S1) and P-image (*_S2) using a user-defined G-factor according to:

image_ani=(image_S1−G×image_S2)/(image_S1+2G× image_S2)

The procedure converts the bit image into a floating point image and does not set negative intensity values to zero.

REFERENCES

1. Giepmans, B. N. G., Adams, S. R., Ellisman, M. H. and Tsien, R. Y. (2006). The fluorescent toolbox for assessing protein location and function. Science 312, 217-224
2. Yan, Y and Marriott, G. (2003). Analysis of Protein Interactions using Fluorescence Technologies. Curr. Opin. Chem. Biol. 7, 1-6.
3. Weber, G. (1952). Polarization of the fluorescence of macromolecules. II. Polarization of the fluorescence of labeled protein molecules. Biochem. J. 51, 155-164
4. Jameson, D M & Ross, J A (2010). Fluorescence Polarization/Anisotropy in Diagnostics and Imaging. Chem Rev. 110. 2685-2708.
5. Visser, A J W G & Muller F. (1980). Time resolved fluorescence of flavins and flavoperoteins 66. 373-385
6. Jares-Erijman, E A. Jovin, T M. Imaging molecular interactions in living cells by FRET microscopy. Curr Opin Chem Biol 10, 409
7. Nalbant, P., L. Hodgson, V. Kraynov, A. Toutchkine, K. M. Hahn. (2004). Activation of Endogenous Cdc42 Visualized in Living Cells. Science, 305: 1615-1619
8. Yan, Y. and Marriott, G. (2003). Determining proximity relationships on single protein complexes using fluorescence resonance energy transfer imaging microscopy and fluorescence polarization imaging microscopy. Meth. Enzymol: 36, 560-582

9. Lee, J., O'Kane, D. and Visser, A. (1985). Spectral properties and function of two lumazine proteins from *Photobacterium*. Biochemistry. 24, 1476-1483.
10. Sato, Y., Shimizu, S., Ohtaki, A., Noguchi, K., Miyatake, H., Dohmae, N., Sasaki, S., Odaka, M. and Yohda, M. (2009). Crystal structures of the Lumazine Protein from *Photobacterium kishitanii* in complexes with the authentic chromophore, 6,7-dimethyl-8-(1'-D-Ribityl) Lumazine, and its analogues, Riboflavin and Flavin Mononucleotide, at high resolution. J. Bacteriology. 192, 127-133.
11. Salomon, M. Christie, J M., Knieb, E., Lempert, U., Briggs, W R. (2000). Photochemical and mutational analysis of the FMN-binding domains of the plant blue light receptor, phototropin. Biochemistry 39, 9401.
12. Crosson, S., Moffat, K. (2001). Structure of a flavin-binding plant photoreceptor domain: insights into light-mediated signal transduction. Proc Natl Acad Sci USA 98, 2995
13. Axelrod, D. (1989) Methods in Cell Biology. Pages 333-352
14. Petchprayoon, C., Khanit, S. Tanaka, J., Yan, Y. and Marriott, G. (2005). Fluorescent Kabiramides: New Probes to Quantify Actin in vitro and in vivo. Bioconjugate Chem. 16, 1382-1389
15. Heidecker, M., Yan-Marriott, Y and Marriott, G. (1995). Fluorescence Resonance Energy Transfer Between Fluorescent Phalloidins on Single Actin Filaments. Biochemistry 34, 11017.
16. Marriott, G., Heidecker M., Diamandis, E. and Yan-Marriott, Y. (1994). Time-resolved Delayed Luminescence Image Microscopy Using Europium-Ion Chelates. Biophysical J. 67, 957
17. Roennov-Jessen L and Bissell M J (2009). Breast cancer by proxy: can the microenvironment be both the cause and consequence. Trends Mol Med. 15.513
18. Lam, A., St-Pierre, F., Gong, Y., Marshall, J., Cranfill, P., Baird, M., McKeown, M., Wiedemann, J., Davidson, M., Schnitzer, M., Tsien, R. and Lin, M. Improving FRET dynamic range with bright green and red fluorescent proteins. Nature Methods. 9, 1005-1012. (2012).
19. Mao, S., Benninger, R K W., Piston, D., Jackson, Easley, C., D. Yan, Y. & Marriott, G. (2008). Optical lock-in detection of FRET using genetically encoded optical switches: High contrast FRET imaging of protein interactions in living cells. Biophysical J. 94, 4515-4524
20. S. Chapman et al., (2008). The photoreversible fluorescent protein iLOV outperforms GFP as a reporter of plant virus infection. Proc Natl Acad Sci USA 105, 20038.
21. Visser A J, Ykema T, van Hoek A, O'Kane D J, Lee J. (1985). Determination of rotational correlation times from deconvoluted fluorescence anisotropy decay curves. Demonstration with 6,7-dimethyl-8-ribityllumazine and lumazine protein from *Photobacterium leiognathi* as fluorescent indicators. Biochemistry. 12:1489-96.
22. Visser, A J W G, Ghisla, S., Massey, V., Müller, F., Veeger, C (1979). Fluorescence Properties of Reduced Flavins and Flavoproteins. European Journal of Biochemistry 101. 13-21.
23. Vilardaga, J P, Bunemann, M., Krasel, C., Castro, M. Lohse, M J. (2003). Measurement of the millisecond activation switch of G protein-coupled receptors in living cells. Nat Biotechnol 21, 807
24. Baird, G. S.; Zacharias, D. A.; Tsien, R. Y. (1999). "Circular permutation and receptor insertion within green fluorescent proteins". PNAS (USA) 96. 11241-11246.
25. Wu, Y, Frey, D., Lungu, O. I., Jaehrig, A., Schlichting, I., Kuhlman, B. and Hahn, K. M. (2009). A genetically encoded photoactivatable Rac controls the motility of living cells. Nature, 461: 104-110
26. Owen, D, Lowe, P., Nietlispach, D., Brosnan, E., Chirgadze, D., Parker, P., Blundell, T. and Mott, H. (2003) Molecular dissection of the interaction between the small G Proteins Rac1 and RhoA and protein kinase C-related Kinase 1 (PRK1). J. Biol. Chem. 278: 50578-50587.
27. Heidecker M, Yan-Marriott Y, Marriott G (1995) Proximity relationships and structural dynamics of the phalloidin binding site of actin filaments in solution and on single actin filaments on heavy meromyosin. Biochemistry 34(35):11017-11025.
28. van der Krogt G N M, Ogink J, Ponsioen B, Jalink K (2008) A comparison of donoracceptor pairs for genetically encoded FRET sensors: Application to the Epac cAMP sensor as an example. PLoS One 3(4):e1916.
29. Yan Y, Marriott G (2003) Fluorescence resonance energy transfer imaging microscopy and fluorescence polarization imaging microscopy. Methods Enzymol 360:561-580.
30. Dix J A, Verkman A S (1990) Mapping of fluorescence anisotropy in living cells by ratio imaging. Application to cytoplasmic viscosity. Biophys J 57(2):231-240.
31. Mattheyses A L, Hoppe A D, Axelrod D (2004) Polarized fluorescence resonance energy transfer microscopy. Biophys J 87(4):2787-2797.
32. Cao Z, Huang C C, Tan W (2006) Nuclease resistance of telomere-like oligonucleotides monitored in live cells by fluorescence anisotropy imaging. Anal Chem 78(5):1478-1484.
33. Chatwell L, et al. (2008) Structure of lumazine protein, an optical transponder of luminescent bacteria. J Mol Biol 382(1):44-55.
34. Lee J, O'Kane D J, Visser A J W G (1985) Spectral properties and function of two lumazine proteins from *Photobacterium*. Biochemistry 24(6):1476-1483.
35. Wolfram Research (2015) Mathematica (Wolfram Research, Inc., Champaign, Ill.), Version 10.1.
36. Mott H R, et al. (1999) Structure of the small G protein Cdc42 bound to the GTPasebinding domain of ACK. Nature 399(6734):384-388.
37. Mao S, et al. (2008) Optical lock-in detection of FRET using synthetic and genetically encoded optical switches. Biophys J 94(11):4515-4524.
38. Mastro A M, Babich M A, Taylor W D, Keith A D (1984) Diffusion of a small molecule in the cytoplasm of mammalian cells. Proc Natl Acad Sci USA 81(11):3414-3418.
39. Takagi T, Doolittle R F (1974) Amino acid sequence studies on factor XIII and the peptide released during its activation by thrombin. Biochemistry 13(4):750-756.

All publicly available Accessions, database entries and records, and all publications, patents and other references noted herein are hereby incorporated by reference in their entireties.

What is claimed is:

1. A genetically encoded fluorescence protein fragment having a sequence that has a mass of less than 20 kDa, wherein the fragment has a sequence that is at least 95% identical to the sequence of SEQ ID NOS: 8 or 9 corresponding to the sequence of the genetically encoded fluorescence protein fragment, and having a fluorescent anisotropic lifetime that is >4.0 ns, wherein the genetically encoded fluorescence protein fragment further comprises an amino acid based targeting molecule, wherein the genetically encoded fluorescence protein fragment and the amino acid based targeting molecule are linked to each other by a linker, and wherein the genetically encoded fluorescence protein fragment is configured for fluorescent anisotropy-based measurement in a bound complex with a target protein.

2. An isolated fluorescent fragment of lumazine binding protein (LUMP), wherein the fragment is less than 20 kDa and is a fragment of a sequence having at least 95% identity to SEQ ID NO: 8 or 9, wherein the fragment has a fluorescent anisotropic lifetime that is greater than 4.0 ns, wherein the isolated fluorescent fragment further comprises an amino acid based targeting molecule, wherein the isolated fluorescent fragment and the amino acid based targeting molecule are linked to each other by a linker, and wherein the isolated fluorescent fragment is configured for fluorescent anisotropy-based measurement in a bound complex with a target protein.

3. The isolated fluorescent variant of LUMP of claim 2, wherein the lifetime is at least 10 ns.

4. The isolated fluorescent variant of LUMP of claim 2, wherein the lifetime is at least 14 ns.

5. A fluorescent anisotropy based sensor, the sensor comprising: an amino acid based targeting molecule; and
a fluorescent molecule that is covalently linked to the amino acid based targeting molecule, wherein the fluorescent molecule is a truncated variant, wherein the truncated variant is no greater in size than 10 KDa, wherein the fragment is a fragment of a sequence that has at least 95% identity to SEQ ID NO: 8 or 9, and wherein the truncated variant has an anisotropic lifetime of greater than 4 ns,
wherein the genetically encoded fluorescence molecule and the amino acid based targeting molecule are linked to each other by a linker, and
wherein the fluorescent anisotropy based sensor is configured for fluorescent anisotropy-based measurement in a bound complex with a target protein.

6. The fluorescent anisotropy based sensor of claim 5, wherein the amino acid based targeting molecule comprises a targeting peptide or protein domain that represent a human proteome.

7. The fluorescent anisotropy based sensor of claim 5, wherein the amino acid based targeting molecule comprises a g-protein binding domain.

8. The genetically encoded fluorescence protein fragment of claim 1 wherein the fragment wherein the fragment is a fragment of a sequence that has 100% identity to SEQ ID NO: 8 or 9.

9. The isolated fluorescent fragment of LUMP of claim 2, wherein the fragment is a fragment of a sequence that has 100% identity to SEQ ID NO: 8 or 9.

10. The fluorescent anisotropy based sensor of claim 5, wherein the fragment is a fragment of a sequence that has 100% identity to SEQ ID NO: 8 or 9.

11. The fluorescent anisotropy based sensor of claim 5, wherein the linker is a flexible linker.

12. The fluorescent anisotropy based sensor of claim 5, wherein the linker is a cleavable linker.

13. The fluorescent anisotropy based sensor of claim 1, wherein the fragment is SEQ ID NO: 8.

14. The fluorescent anisotropy based sensor of claim 2, wherein the fragment is SEQ ID NO: 8.

15. The fluorescent anisotropy based sensor of claim 5, wherein the fragment is SEQ ID NO: 8.

* * * * *